US007361503B2

(12) United States Patent
Dumonceaux et al.

(10) Patent No.: US 7,361,503 B2
(45) Date of Patent: Apr. 22, 2008

(54) SEQUENCES ENCODING HEPATITIS C VIRUS GLYCOPROTEINS

(75) Inventors: Julie Dumonceaux, Paris (FR); Emmanuel G. Cormier, Bronx, NY (US); Jason P. Gardner, Ardsley, NY (US); Tatjana Dragic, Scarsdale, NY (US)

(73) Assignees: Albert Einstein College of Medicine of Yeshiva University, Bronx, NY (US); Progenics Pharmaceuticals, Inc., Tarrytown, NY (US)

( * ) Notice: Subject to any disclaimer, the term of this patent is extended or adjusted under 35 U.S.C. 154(b) by 319 days.

(21) Appl. No.: 10/985,205

(22) Filed: Nov. 9, 2004

(65) Prior Publication Data

US 2005/0266400 A1 Dec. 1, 2005

Related U.S. Application Data

(60) Provisional application No. 60/519,536, filed on Nov. 12, 2003.

(51) Int. Cl.
*C12N 15/63* (2006.01)

(52) U.S. Cl. ................................ 435/320.1; 424/218.1

(58) Field of Classification Search ..................... None
See application file for complete search history.

(56) References Cited

U.S. PATENT DOCUMENTS

| | | | |
|---|---|---|---|
| 3,645,852 | A | 2/1972 | Axen et al. |
| 4,816,567 | A | 3/1989 | Cabilly et al. |
| 5,225,539 | A | 7/1993 | Winter |
| 5,545,806 | A | 8/1996 | Lonberg et al. |
| 5,545,807 | A | 8/1996 | Surani et al. |
| 5,585,089 | A | 12/1996 | Queen et al. |
| 5,591,669 | A | 1/1997 | Krimpenfort et al. |
| 5,598,369 | A | 1/1997 | Chen et al. |
| 5,693,761 | A | 12/1997 | Queen et al. |
| 5,882,852 | A | 3/1999 | Bukh et al. |
| 6,150,584 | A | 11/2000 | Kucherlapati et al. |
| 6,572,864 | B1 | 6/2003 | Bukh et al. |
| 2002/0141974 | A1 | 10/2002 | Jolly et al. |
| 2004/0029278 | A1 | 2/2004 | Dubensky, Jr. et al. |

FOREIGN PATENT DOCUMENTS

| | | | |
|---|---|---|---|
| EP | 1398371 | A1 | 9/2002 |
| WO | WO 90/07861 | | 7/1990 |
| WO | WO 01/21807 | A1 | 3/2001 |
| WO | WO 02/070651 | A2 | 9/2002 |
| WO | WO 02/074941 | A1 | 9/2002 |
| WO | WO 2004/024904 | A2 | 3/2004 |
| WO | WO 2005/010035 | A2 | 2/2005 |

OTHER PUBLICATIONS

Mustafa et al. J. of Virology, 2000, vol. 74, p. 9431-9440.*
Verma, Nature, 1997, vol. 389, p. 239-242.*
Orkin, 1995, p. 1-39.*
Alter, H.J., and Seeff, L.B. (1993) Transfusion-associated hepatitis. In "Viral Hepatitis" (Z.A. Thomas, ed.) Churchill Livingstone, Edinburgh.
ANONYMOUS (no author listed) (1999) Global surveillance and control of hepatitis C. Report of a WHO Consultation organized in collaboration with the Viral Hepatitis Prevention Board, Antwerp, Belgium. J. Viral Hepat. 6: 35-47.
Bartenschlager, R., and Lohmann, V. (2000) Replication of hepatitis C virus. J. Gen. Virol. 81: 1631-1648.
Bartosch, B., et al. (2003) Infectious hepatitis C virus pseudo-particles containing functional E1-E2 envelope protein complexes. J. Exp. Med. 197: 633-642.
Blanchard, E., et al. (2002) Hepatitis C virus-like particle morphogenesis. J. Virol. 76: 4073-4079.
Blight, K.J., et al. (2000) Efficient initiation of HCV RNA replication in cell culture. Science 290: 1272-1974.
Buonocore, L., et al. (2002) Characterization of vesicular stomatitis virus recombinants that express and incorporate high levels of hepatitis C virus glycoproteins. J. Virol. 76: 6865-6872.
Charloteaux, B., et al. (2002) Analysis of the C-terminal membrane anchor domains of hepatitis C virus glycoproteins E1 and E2: toward a topological model. J. Virol. 76: 1944-1958.
Cocquerel, L., et al. (1999) The transmembrane domain of hepatitis C virus glycoprotein E1 is a signal for static retention in the endoplasmic reticulum. J. Virol. 73: 2641-2649.
Cocquerel, L., et al. (2001) Coexpression of hepatitis C virus envelope proteins E1 and E2 in cis improves the stability of membrane insertion of E2. J. Gen. Virol. 82: 1629-1635.
Cocquerel, L., et al. (1998) A retention signal necessary and sufficient for endoplasmic reticulum localization maps to the transmembrane domain of hepatitis C virus glycoprotein E2. J. Virol. 72: 2183-2191.
Cocquerel, L. et al. (2002) Topological changes in the transmembrane domains of hepatitis C virus envelope glycoproteins. EMBO J. 21: 2893-2902.

(Continued)

*Primary Examiner*—Bruce R. Campell
*Assistant Examiner*—Agnieszka Boesen
(74) *Attorney, Agent, or Firm*—John P. White; Cooper & Dunham LLP

(57) ABSTRACT

The present invention concerns a modified nucleic acid molecule comprising a nucleotide sequence coding for a full length hepatitis C virus (HCV) glycoprotein selected from the group consisting of E1 glycoprotein and E1/E2 glycoprotein heterodimer, this molecule having at least one nucleotide alteration, wherein, due to this alteration, at least one RNA splice site selected from the group consisting of RNA splice acceptor and RNA splice donor sites is eliminated from the coding sequence. The invention is also directed to methods for expressing on the surface of a cell and a pseudovirion an HCV glycoprotein, wherein the majority of the glycoprotein is full length. The invention further provides a cell and a pseudovirion expressing such glycoprotein. The invention still further provides a method for determining whether an agent inhibits HCV fusion with and entry into a target cell. The invention also provides an agent that inhibits HCV fusion with and entry into a target cell. The invention further provides methods for treating a subject afflicted with an HCV-associated disorder, for preventing an HCV infection in a subject, and for inhibiting in a subject the onset of an HCV-associated disorder.

19 Claims, 19 Drawing Sheets

OTHER PUBLICATIONS

Cocquerel, L., et al. (2000) Charged residues in the transmembrane domains of hepatitis C virus glycoproteins play a major role in the processing, subcellular localization, and assembly of these envelope proteins. J. Virol. 74: 3623-3633.
Dash, S., et al. (1997) Transfection of HepG2 cells with infectious hepatitis C virus genome. Am. J. Pathol. 151: 363-373.
Deleersnyder, V., et al. (1997) Formation of native hepatitis C virus glycoprotein complexes. J. Virol. 71: 697-704.
Derse, D., et al. (1995) Virions released from cells transfected with a molecular clone of human T-cell leukemia virus type I give rise to primary and secondary infections of T cells. J. Virol. 69: 1907-1912.
Derse, D., et al. (2001) Examining human T-lymphotropic virus type 1 infection and replication by cell-free infection with recombinant virus vectors. J. Virol. 75: 8461-8468.
De Vos, R., et al. (2002) Ultrastructural visualization of hepatitis C virus components in human and primate liver biopsies. J. Hepatol. 37: 370-379.
Dubuisson, J., et al. (2000) Glycosylation of the hepatitis C virus envelope protein E1 is dependent on the presence of a downstream sequence on the viral polyprotein. J. Biol. Chem. 275: 30605-30609.
Dubuisson, J., et al. (1994) Formation and intracellular localization of hepatitis C virus envelope glycoprotein complexes expressed by recombinant vaccinia and sindbis viruses. J. Virol. 68: 6147-6160.
Dumonceaux, J., et al. (2003) Expression of unmodified hepatitis C virus envelope glycoprotein-coding sequences leads to cryptic intron excision and cell surface expression of E1/E2 heterodimers comprising full-length and partially deleted E1. J. Virol. 77: 13418-13424.
Duvet, S., et al. (1998) Hepatitis C virus glycoprotein complex localization in the endoplasmic reticulum involves a determinant for retention and not retrieval. J. Biol. Chem. 273: 32088-32095.
Earl, P.L., et al. (1998) Generation of recombinant vaccinia viruses. In "Current Protocols in Molecular Biology" (Ausubel, F.M. et al. Eds.), Greene Publishing Associates/Wiley Interscience, New York, pp. 16.17.1-16.17.19.
Egger, D., et al. (2002) Expression of hepatitis C virus proteins induces distinct membrane alterations including a candidate viral replication complex. J. Virol. 76: 5974-5984.
Flint, M., and Keating, J.M. (1999) The C-terminal region of the hepatitis C virus E1 glycoprotein confers localization within the endoplasmic reticulum. J. Gen. Virol. 80: 1943-1947.
Flint, M., et al. (1999) Functional analysis of cell surface-expressed hepatitis C virus E2 glycoprotein. J. Virol. 73: 6782-6790.
Fry, D.E., and Flint, L.M., Jr. (1997) Hepatitis: an overview of important issues. Bull. Am. Coll. Surg. 82: 8-13.
Gardner, J.P., et al. (2003) L-SIGN (CD 209L) is a liver-specific capture receptor for hepatitis C virus. Proc. Natl. Acad. Sci. USA 100: 4498-4503.
Goldberg, M., et al. (1999) Solid support synthesis of 14-membered macrocycles containing 4-hydroxyproline structural unit via $S_NAr$ methodology. Tetrahedron 55: 13887-13898.
Grakoui, A., et al. (1993) Expression and identification of hepatitis C virus polyprotein cleavage products. J. Virol. 67: 1385-1395.
Greive, S.J., et al. (2002) Expression of the hepatitis C virus structural proteins in mammalian cells induces morphology similar to that in natural infection. J. Viral Hepat. 9: 9-17.
Hsu, M., et al. (2003) Hepatitis C virus glycoproteins mediate pH-dependent cell entry of pseudotyped retroviral particles. Proc. Natl. Acad. Sci. USA 100: 7271-7276.
Iacovacci, S., et al. (1997) Molecular characterization and dynamics of hepatitis C virus replication in human fetal hepatocytes infected in vitro. Hepatology 26: 1328-1337.
Kiselyov, A.S., et al. (1998) Solid support synthesis of 14-membered macrocycles containing the thioether bridge via $S_NAr$ methodology. Tetrahedron 54: 10635-10640.
Kiselyov, A.S., et al. (1999a) Solid support synthesis of 14-membered macrocycles via $S_NAr$ methodology on acrylate resin. Tetrahedron Lett. 40: 2465-2468.
Kiselyov, A.S., et al. (1999b) Solid support synthesis of 14- and 17-membered macrocycles via the $S_NAr$ methodology. Tetrahedron 55: 14813-14822.
Kobayashi, N., et al. (2000) Prevention of acute liver failure in rats with reversibly immortalized human hepatocytes. Science 287: 1258-1262.
Kobayashi, N., et al. (2001) Cre/1oxP-based reversible immortalization of human hepatocytes. Cell Transplant. 10: 383-386.
Köhler, G., and Milstein, C. (1975) Continuous cultures of fused cells secreting antibody of predefined specificity. Nature 256: 495-497.
Kolykhalov, A.A., et al. (1997) Transmission of hepatitis C by intrahepatic inoculation with transcribed RNA. Science 277: 570-574.
Kreig, A.M., et al. (1995) CpG motifs in bacterial DNA trigger direct B-cell activation. Nature 374: 546-549.
Lagging, L.M., et al. (1998) Functional role of hepatitis C virus chimeric glycoproteins in the infectivity of pseudotyped virus. J. Virol. 72: 3539-3546.
Lagging, L.M., et al. (2002) Neutralization of pseudotyped vesicular stomatitis virus expressing hepatitis C virus envelope glycoprotein 1 or 2 by serum from patients. J. Infect. Dis. 185: 1165-1169.
Langer, r. (1990) New methods of drug delivery. Science 249: 1527-1533.
Lauer, G.M., and Walker, B.D. (2001) Hepatitis C virus infection. New Engl. J. Med. 345: 41-52.
Li, K.J., and Garoff, H. (1996) Production of infectious recombinant moloney murine leukemia virus particles in BHK cells using semliki forest virus-derived RNA expression vectors. Proc. Natl. Acad. Sci. USA 93: 11658-11663.
Litwin, V., et al. (1996) Human immunodeficiency virus type 1 membrane fusion mediated by a laboratory-adapted strain and a primary isolate analyzed by resonance energy transfer. J. Virol. 70: 6437-6441.
Lu, Y.E., et al. (2000) Semliki forest virus budding: assay, mechanisms, and cholesterol requirement. J. Virol. 74: 7708-7719.
Martiere, G., et al. (2001) Hepatitis C virus structural proteins reside in the endoplasmic reticulum as well as in the intermediate compartment/cis-Golgi complex region of stably transfected cells. Virology 280: 176-182.
Matsuura, Y., et al. (2001) Characterization of pseudotype VSV possessing HCV envelope proteins. Virology 286: 263-275.
Matsuura, Y., et al. (1994) Processing of E1 and E2 glycoproteins of hepatitis C virus expressed in mammalian and insect cells. Virology 205: 141-150.
McHutchinson, J.G., et al. (1998) Interferon alfa-2b alone or in combination with ribavirin as initial treatment for chronic hepatitis C. Hepatitis Interventional Therapy Group. New Engl. J. Med. 339: 1485-1492.
Meyer, K., et al. (2002) Complement-mediated enhancement of antibody function for neutralization of pseudotype virus containing hepatitis C virus E2 chimeric glycoprotein. J. Virol. 76: 2150-2158.
Meyer, K., et al. (2000) Functional features of hepatitis C virus glycoproteins for pseudotype virus entry into mammalian cells. Virology 276: 214-226.
Michalak, J.P., et al. (1997) Characterization of truncated forms of hepatitis C virus glycoproteins. J. Gen. Virol. 78: 2299-2306.
Op De Beeck, A., et al. (2001) Biogenesis of hepatitis C virus envelope glycoproteins. J. Gen. Virol. 82: 2589-2595.
Op De Beeck, A., et al. (2000) The transmembrane domains of hepatitis C virus envelope glycoproteins E1 and E2 play a major role in heterodimerization. J. Biol. Chem. 275: 21428-31437.
Ouyang, X., et al. (1999a) Solid support synthesis of 2-substituted dibenz[b,f]oxazepin-11(1O*H*)-ones via $S_NAr$ methodology on AMEBA resin. Tetrahedron 55: 2827-2834.
Ouyang, X., and Kiselyov, A.S. (1999b) Fast and efficient synthesis of substituted dibenz[b, f]oxazocines on solid support. Tetrahedron 55: 8295-8302.
Ouyang, X., et al. (1999c) Novel synthesis of dibenzo[*b,g*]1, 5-oxazocines. Tetrahedron Lett. 40: 5827-5830.
Parveen, Z., et al. (2000) Spleen necrosis virus-derived C-type retroviral vectors for gene transfer to quiescent cells. Nat. Biotechnol. 18: 623-629.

Patel, J., et al. (1999) Covalent interactions are not required to permit or stabilize the non-covalent association of hepatitis C virus glycoproteins E1 and E2. J. Gen. Virol. 80: 1681-1690.
Patel, J., et al. (2001) The transmembrane domain of the hepatitis C virus E2 glycoprotein is required for correct folding of the E1 glycoprotein and native complex formation. Virology 279: 58-68.
Person-Fernandez, A., and Beaud, G. (1986) Purification and characterization of a protein synthesis inhibitor associated with vaccinia virus. J. Biol. Chem. 261: 8283-8289.
Pettersson, R.F. (1991) Protein localization and virus assembly at intracellular membranes. Curr. Top. Microbiol. Immunol. 170: 67-106.
Pietschmann, T., et al. (2002) Persistent and transient replication of full-length hepatitis C virus genomes in cell culture. J. Virol. 76: 4008-4021.
Ploubidou, A., et al. (2000) Vaccinia virus infection disrupts microtubule organization and centrosome function. EMBO J. 19: 3932-3944.
Ralston, R., et al. (1993) Characterization of hepatitis C virus envelope glycoprotein complexes expressed by recombinant vaccinia viruses. J. Virol. 67: 6753-6761.
Reed, K.E., and Rice, C.M. (2000) Overview of hepatitis C virus genome structure, polyprotein processing, and protein properties. Curr. Top. Microbiol. Immunol. 242: 55-84.
Rice, C.M. (1996) Flaviviridiae: The viruses and their replication. In "Fields Virology" 3rd ed. (Fields, B.N. et al. Eds.) pp. 931-959. Lippincott-Raven Publishers, Philadelphia.
Risco, C., et al. (2002) Endoplasmic reticulum-golgi intermediate compartment membranes and vimentin filaments participate in vaccinia virus assembly. J. Virol. 76: 1839-1855.
Rodriguez, J.R., et al. (1997) Characterization of early stages in vaccinia virus membrane biogenesis: implications of the 21-kilodalton protein and a newly identified 15-kilodalton envelope protein. J. Virol. 71: 1821-1833.
Sanger, C., et al. (2001) Adverse effects of MVA-T7 on the transport of Marburg virus glycoprotein. J. Virol. Methods 91: 29-35.
Selby, M.J., et al. (1994) Complex processing and protein:protein interactions in the E2:NS2 region of HCV. Virology 204: 114-122.
Serafino, A., et al. (1997) Ultrastructural observations of viral particles within hepatitis C virus-infected human B lymphoblastoid cell line. Res. Virol. 148: 153-159.
Shimizu, Y.K., et al. (1996) Hepatitis C virus: detection of intracellular virus particles by electron microscopy. Hepatology 23: 205-209.
Spaete, R.R., et al. (1992) Characterization of the hepatitis C virus E2/NS1 gene product expressed in mammalian cells. Virology 188: 819-830.
Szepanski, S., et al. (1994) Post-translational folding of the influenza C virus glycoprotein HEF: defective processing in cells expressing the cloned gene. J. Gen. Virol. 75: 1023-1030.
Takikawa, S., et al. (2000) Cell fusion activity of hepatitis C virus envelope proteins. J. Virol. 74: 5066-5074.
Triyatni, M., et al. (2002) Interaction of hepatitis C virus-like particles and cells: a model system for studying viral binding and entry. J. Virol. 76: 9335-9344.
Wei, G.P., and Phillips, G.B. (1998) Solid phase synthesis of benzimidazolones. Tetrahedron Lett. 39: 179-182.
Yanagi, M., et al. (1997) Transcripts from a single full-length cDNA clone of hepatitis C virus are infectious when directly transfected into the liver of a chimpanzee. Proc. Natl. Acad. Sci. USA 94: 8738-8743.
Young, K.K., et al. (1993) Detection of hepatitis C virus RNA by a combined reverse transcription-polymerase chain reaction assay. J. Clin. Microbiol. 31: 882-886.
Seong et al. (2001) Immunogenicity Of The E1E2 Proteins Of Hepatitis C Virus Expressed By Recombinant Adenoviruses. Vaccine, 19: 2955-2964.
V. Falcon et al. (1999) Ultrasound And Immunocytochemical Evidences Of Core-Particle Formation In The Methyloytophic Pichia Pastoris Yeast When . . . Tissue Cell., Tissue Cell., 31(2): 117-125.
T. F. Baumert et al. (1998) Hepatitis C Virus Structural Proteins Assemble Into Viruslike Particles In Insect Cells. J. Virol., 72(5): 1998-2005.

* cited by examiner 1 gccagccccc tgatgggggc gacactccac catgaatcac tcccctgtga ggaactactg
61 tcttcacgca gaaagcgtct agccatggcg ttagtatgag tgtcgtgcag cctccaggac
121 cccccctccc gggagagcca tagtggtctg cggaaccggt gagtacaccg gaattgccag
181 gacgaccggg tcctttcttg gataaacccg ctcaatgcct ggagatttgg gcgtgccccc
241 gcaagactgc tagccgagta gtgttgggtc gcgaaaggcc ttgtggtact gcctgatagg
301 gtgcttgcga gtgccccggg aggtctcgta gaccgtgcac catgagcacg aatcctaaac
361 ctcaaagaaa aaccaaacgt aacaccaacc gtcgcccaca ggacgtcaag ttcccgggtg
421 gcggtcagat cgttggtgga gtttacttgt tgccgcgcag gggccctaga ttgggtgtgc
481 gcgcgacgag gaagacttcc gagcggtcgc aacctcgagg tagacgtcag cctatcccca
541 aggcacgtcg gcccgagggc aggacctggg ctcagcccgg gtacccttgg cccctctatg
601 gcaatgaggg ttgcgggtgg gcgggatggc tcctgtctcc ccgtggctct cggcctagct
661 ggggccccac agacccccgg cgtaggtcgc gcaatttggg taaggtcatc gataccctta
721 cgtgcggctt cgccgacctc atggggtaca taccgctcgt cggcgcccct cttggaggcg
781 ctgccagggc cctggcgcat ggcgtccggg ttctggaaga cggcgtgaac tatgcaacag
841 ggaaccttcc tggttgctct ttctctatct tccttctggc cctgctctct tgcctgactg
901 tgcccgcttc agcctaccaa gtgcgcaatt cctcggggct ttaccatgtc accaatgatt
961 gccctaactc gagtattgtg tacgaggcgg ccgatgccat cctgcacact ccggggtgtg
1021 tcccttgcgt tcgcgagggt aacgcctcga ggtgttgggt ggcggtgacc cccacggtgg
1081 ccaccaggga cggcaaactc cccacaacgc agcttcgacg tcatatcgat ctgcttgtcg
1141 ggagcgccac cctctgctcg gccctctacg tgggggacct gtgcgggtct gtctttcttg
1201 ttggtcaact gtttaccttc tctcccaggc gccactggac gacgcaagac tgcaattgtt
1261 ctatctatcc cggccatata acgggtcatc gcatggcatg ggatatgatg atgaactggt
1321 cccctacggc agcgttggtg gtagctcagc tgctccggat cccacaagcc atcatggaca
1381 tgatcgctgg tgctcactgg ggagtcctgg cgggcatagc gtatttctcc atggtgggga
1441 actgggcgaa ggtcctggta gtgctgctgc tatttgccgg cgtcgacgcg gaaacccacg
1501 tcaccggggg aaatgccggc cgcaccacgg ctgggcttgt tggtctcctt acaccaggcg
1561 ccaagcagaa catccaactg atcaacacca acggcagttg gcacatcaat agcacggcct
1621 tgaattgcaa tgaaagcctt aacaccggct ggttagcagg gctcttctat caacacaaat
1681 tcaactcttc aggctgtcct gagaggttgg ccagctgccg acgccttacc gattttgccc
1741 agggctgggg tcctatcagt tatgccaacg gaagcggcct cgacgaacgc ccctactgct
1801 ggcactaccc tccaagacct tgtggcattg tgcccgcaaa gagcgtgtgt ggcccggtat
1861 attgcttcac tcccagcccc gtggtggtgg gaacgaccga caggtcgggc gcgcctacct
1921 acagctgggg tgcaaatgat acggatgtct tcgtccttaa caacaccagg ccaccgctgg
1981 gcaattggtt cggttgtacc tggatgaact caactggatt caccaaagtg tgcggagcgc
2041 ccccttgtgt catcggaggg gtgggcaaca acaccttgct ctgccccact gattgcttcc
2101 gcaaacatcc ggaagccaca tactctcggt gcggctccgg tccctggatt acacccaggt
2161 gcatggtcga ctacccgtat aggctttggc actatccttg taccatcaat tacaccatat
2221 tcaaagtcag gatgtacgtg ggaggggtcg agcacaggct ggaagcggcc tgcaactgga
2281 cgcggggcga acgctgtgat ctggaagaca gggacaggtc cgagctcagc ccgttgctgc
2341 tgtccaccac acagtggcag gtccttccgt gttctttcac gaccctgcca gccttgtcca
2401 ccggcctcat ccacctccac cagaacattg tggacgtgca gtacttgtac ggggtagggt
2461 caagcatcgc gtcctgggcc attaagtggg agtacgtcgt tctcctgttc cttctgcttg
2521 cagacgcgcg cgtctgctcc tgcttgtgga tgatgttact catatcccaa gcggaggcgg
2581 ctttggagaa cctcgtaata ctcaatgcag catccctggc cgggacgcac ggtcttgtgt
2641 ccttcctcgt gttcttctgc tttgcgtggt atctgaaggg taggtgggtg cccggagcgg
2701 tctacgccct ctacgggatg tggcctctcc tcctgctcct gctggcgttg cctcagcggg
2761 catacgcact ggacacggag gtggccgcgt cgtgtggcgg cgttgttctt gtcgggttaa
2821 tggcgctgac tctgtcgcca tattacaagc gctatatcag ctggtgcatg tggtggcttc
2881 agtattttct gaccagagta gaagcgcaac tgcacgtgtg ggttcccccc ctcaacgtcc
2941 ggggggggcg cgatgccgtc atcttactca tgtgtgtagt acacccgacc ctggtatttg
3001 acatcaccaa actactcctg gccatcttcg gacccctttg gattcttcaa gccagtttgc
3061 ttaaagtccc ctacttcgtg cgcgttcaag gccttctccg gatctgcgcg ctagcgcgga
3121 agatagccgg aggtcattac gtgcaaatgg ccatcatcaa gttaggggcg cttactggca
3181 cctatgtgta taaccatctc acccctcttc gagactgggc gcacaacggc ctgcgagatc
3241 tggccgtggc tgtggaacca gtcgtcttct cccgaatgga gaccaagctc atcacgtggg
3301 gggcagatac cgccgcgtgc ggtgacatca tcaacggctt gcccgtctct gcccgtaggg
3361 gccaggagat actgcttggg ccagccgacg gaatggtctc caaggggtgg aggttgctgg
3421 cgcccatcac ggcgtacgcc cagcagacga gaggcctcct agggtgtata atcaccagcc
3481 tgactggccg ggacaaaaac caagtggagg gtgaggtcca gatcgtgtca actgctaccc

Figure 1a

```
3541 aaaccttcct ggcaacgtgc atcaatgggg tatgctggac tgtctaccac ggggccggaa
3601 cgaggaccat cgcatcaccc aagggtcctg tcatccagat gtataccaat gtggaccaag
3661 accttgtggg ctggcccgct cctcaaggtt cccgctcatt gacaccctgt acctgcggct
3721 cctcggacct ttacctggtc acgaggcacg ccgatgtcat tcccgtgcgc cggcgaggtg
3781 atagcagggg tagcctgctt tcgccccggc ccatttccta cttgaaaggc tcctcggggg
3841 gtccgctgtt gtgccccgcg ggacacgccg tgggcctatt cagggccgcg gtgtgcaccc
3901 gtggagtggc taaagcggtg gactttatcc ctgtggagaa cctagggaca accatgagat
3961 ccccggtgtt cacggacaac tcctctccac cagcagtgcc ccagagcttc caggtggccc
4021 acctgcatgc tcccaccggc agcggtaaga gcaccaaggt cccggctgcg tacgcagccc
4081 agggctacaa ggtgttggtg ctcaacccct ctgttgctgc aacgctgggc tttggtgctt
4141 acatgtccaa ggcccatggg gttgatccta atatcaggac cggggtgaga acaattacca
4201 ctggcagccc catcacgtac tccacctacg gcaagttcct tgccgacggc gggtgctcag
4261 gaggtgctta tgacataata atttgtgacg agtgccactc cacggatgcc acatccatct
4321 tgggcatcgg cactgtcctt gaccaagcag agactgcggg ggcgagactg gttgtgctcg
4381 ccactgctac ccctccgggc tccgtcactg tgtcccatcc taacatcgag gaggttgctc
4441 tgtccaccac cggagagatc cccttttacg gcaaggctat cccccctcgag gtgatcaagg
4501 ggggaagaca tctcatcttc tgccactcaa agaagaagtg cgacgagctc gccgcgaagc
4561 tggtcgcatt gggcatcaat gccgtggcct actaccgcgg tcttgacgtg tctgtcatcc
4621 cgaccagcgg cgatgttgtc gtcgtgtcga ccgatgctct catgactggc tttaccggcg
4681 acttcgactc tgtgatagac tgcaacacgt gtgtcactca gacagtcgat ttcagccttg
4741 accctacctt taccattgag acaaccacgc tcccccagga tgctgtctcc aggactcaac
4801 gccgggggcag gactggcagg gggaagccag gcatctatag atttgtggca ccgggggagc
4861 gcccctccgg catgttcgac tcgtccgtcc tctgtgagtg ctatgacgcg ggctgtgctt
4921 ggtatgagct cacgcccgcc gagactacag ttaggctacg agcgtacatg aacaccccgg
4981 ggcttcccgt gtgccaggac catcttgaat tttgggaggg cgtctttacg ggcctcactc
5041 atatagatgc ccacttttta tcccagacaa agcagagtgg ggagaacttt ccttacctgg
5101 tagcgtacca agccaccgtg tgcgctaggg ctcaagcccc tcccccatcg tgggaccaga
5161 tgtggaagtg tttgatccgc cttaaaccca ccctccatgg gccaacaccc ctgctataca
5221 gactgggcgc tgttcagaat gaagtcaccc tgacgcaccc aatcaccaaa tacatcatga
5281 catgcatgtc ggccgacctg gaggtcgtca cgagcacctg ggtgctcgtt ggcggcgtcc
5341 tggctgctct ggccgcgtat tgcctgtcaa caggctgcgt ggtcatagtg ggcaggatcg
5401 tcttgtccgg gaagccggca attatacctg acagggaggt tctctaccag gagttcgatg
5461 agatggaaga gtgctctcag cacttaccgt acatcgagca agggatgatg ctcgctgagc
5521 agttcaagca gaaggccctc ggcctcctgc agaccgcgtc ccgccatgca gaggttatca
5581 cccctgctgt ccagaccaac tggcagaaac tcgaggtctt ttgggcgaag cacatgtgga
5641 atttcatcag tgggatacaa tacttggcgg gcctgtcaac gctgcctggt aaccccgcca
5701 ttgcttcatt gatggctttt acagctgccg tcaccagccc actaaccact ggccaaaccc
5761 tcctcttcaa catattgggg gggtgggtgg ctgcccagct cgccgccccc ggtgccgcta
5821 ctgcctttgt gggtgctggc ctagctggcg ccgccatcgg cagcgttgga ctggggaagg
5881 tcctcgtgga cattcttgca gggtatggcg cgggcgtggc gggagctctt gtagcattca
5941 agatcatgag cggtgaggtc ccctccacgg aggacctggt caatctgctg cccgccatcc
6001 tctcgcctgg agcccttgta gtcggtgtgg tctgcgcagc aatactgcgc cggcacgttg
6061 gcccgggcga gggggcagtg caatggatga accggctaat agccttcgcc tcccgggggga
6121 accatgtttc ccccacgcac tacgtgccgg agagcgatgc agccgcccgc gtcactgcca
6181 tactcagcag cctcactgta acccagctcc tgaggcgact gcatcagtgg ataagctcgg
6241 agtgtaccac tccatgctcc ggttcctggc taagggacat ctgggactgg atatgcgagg
6301 tgctgagcga ctttaagacc tggctgaaag ccaagctcat gccacaactg cctgggattc
6361 cctttgtgtc ctgccagcgc gggtataggg ggtctggcg aggagacggc attatgcaca
6421 ctcgctgcca ctgtggagct gagatcactg gacatgtcaa aaacgggacg atgaggatcg
6481 tcggtcctag gacctgcagg aacatgtgga gtgggacgtt ccccattaac gcctacacca
6541 cgggcccctg tactcccctt cctgcgccga actataagtt cgcgctgtgg agggtgtctg
6601 cagaggaata cgtggagata aggcgggtgg gggacttcca ctacgtatcg ggtatgacta
6661 ctgacaatct taaatgcccg tgccagatcc catcgcccga atttttcaca gaattggacg
6721 gggtgcgcct acacaggttt gcgccccctt gcaagccctt gctgcgggag gaggtatcat
6781 tcagagtagg actccacgag tacccggtgg ggtcgcaatt accttgcgag cccgaaccgg
6841 acgtagccgt gttgacgtcc atgctcactg atccctccca tataacagca gaggcggccg
6901 ggagaaggtt ggcgagaggg tcacccccctt ctatggccag ctcctcggct agccagctgt
6961 ccgctccatc tctcaaggca acttgcaccg ccaaccatga ctcccctgac gccgagctca
7021 tagaggctaa cctcctgtgg aggcaggaga tgggcggcaa catcaccagg gttgagtcag
```

Figure 1b

```
7081 agaacaaagt ggtgattctg gactccttcg atccgcttgt ggcagaggag gatgagcggg
7141 aggtctccgt acctgcagaa attctgcgga agtctcggag attcgcccgg gccctgcccg
7201 tctgggcgcg gccggactac aacccccCgc tagtagagac gtggaaaaag cctgactacg
7261 aaccacctgt ggtccatggc tgcccgctac cacctccacg gtcccctcct gtgcctccgc
7321 ctcggaaaaa gcgtacggtg gtcctcaccg aatcaaccct atctactgcc ttggccgagc
7381 ttgccaccaa aagttttggc agctcctcaa cttccggcat tacgggcgac aatacgacaa
7441 catcctctga gcccgcccct tctggctgcc cccccgactc cgacgttgag tcctattctt
7501 ccatgccccc cctggagggg gagcctgggg atccggatct cagcgacggg tcatggtcga
7561 cggtcagtag tggggccgac acggaagatg tcgtgtgctg ctcaatgtct tattcctgga
7621 caggcgcact cgtcaccccg tgcgctgcgg aagaacaaaa actgcccatc aacgcactga
7681 gcaactcgtt gctacgccat cacaatctgg tgtattccac cacttcacgc agtgcttgcc
7741 aaaggcagaa gaaagtcaca tttgacagac tgcaagttct ggacagccat taccaggacg
7801 tgctcaagga ggtcaaagca gcggcgtcaa aagtgaaggc taacttgcta tccgtagagg
7861 aagcttgcag cctgacgccc ccacattcag ccaaatccaa gtttggctat ggggcaaaag
7921 acgtccgttg ccatgccaga aaggccgtag cccacatcaa ctccgtgtgg aaagaccttc
7981 tggaagacag tgtaacacca atagacacta ccatcatggc caagaacgag gttttctgcg
8041 ttcagcctga gaaggggggt cgtaagccag ctcgtctcat cgtgttcccc gacctgggcg
8101 tgcgcgtgtg cgagaagatg gccctgtacg acgtggttag caagctcccc ctggccgtga
8161 tgggaagctc ctacggattc caatactcac caggacagcg ggttgaattc ctcgtgcaag
8221 cgtggaagtc caagaagacc ccgatggggt tctcgtatga tacccgctgt tttgactcca
8281 cagtcactga gagcgacatc cgtacggagg aggcaattta ccaatgttgt gacctggacc
8341 cccaagcccg cgtggccatc aagtccctca ctgagaggct ttatgttggg ggccctctta
8401 ccaattcaag gggggaaaac tgcggctacc gcaggtgccg cgcgagcggc gtactgacaa
8461 ctagctgtgg taacaccctc acttgctaca tcaaggcccg ggcagcctgt cgagccgcag
8521 ggctccagga ctgcaccatg ctcgtgtgtg gcgacgactt agtcgttatc tgtgaaagtg
8581 cgggggtcca ggaggacgcg gcgagcctga gagccttcac ggaggctatg accaggtact
8641 ccgccccccc cggggacccc ccacaaccag aatacgactt ggagcttata acatcatgct
8701 cctccaacgt gtcagtcgcc cacgacggcg ctggaaagag ggtctactac cttacccgtg
8761 accctacaac ccccctcgcg agagccgcgt gggagacagc aagacacact ccagtcaatt
8821 cctggctagg caacataatc atgtttgccc ccacactgtg ggcgaggatg atactgatga
8881 cccatttctt tagcgtcctc atagccaggg atcagcttga acaggctctt aactgtgaga
8941 tctacggagc ctgctactcc atagaaccac tggatctacc tccaatcatt caaagactcc
9001 atggcctcag cgcattttca ctccacagtt actctccagg tgaaatcaat agggtggccg
9061 catgcctcag aaaacttggg gtcccgccct tgcgagcttg gagacaccgg gcccggagcg
9121 tccgcgctag gcttctgtcc agaggaggca gggctgccat atgtggcaag tacctcttca
9181 actgggcagt aagaacaaag ctcaaactca ctccaatagc ggccgctggc cggctggact
9241 tgtccggttg gttcacggct ggctacagcg gggagacat ttatcacagc gtgtctcatg
9301 cccggccccg ctggttctgg ttttgcctac tcctgctcgc tgcaggggta ggcatctacc
9361 tcctccccaa ccgatgaagg ttggggtaaa cactccggcc tcttaagcca tttcctgttt
9421 tttttttttt tttttttttt tttttctttt ttttttcttt tcctttcctt ctttttttcc
9481 tttcttttc ccttctttaa tggtggctcc atcttagccc tagtcacggc tagctgtgaa
9541 aggtccgtga gccgcatgac tgcagagagt gctgatactg gcctctctgc agatcatgt
```

Figure 1c

```
   1  atgagcacg aatcctaaac ctcaaagaaa aaccaaacgt aacaccaacc gtcgcccaca
  60 ggacgtcaag ttcccgggtg gcggtcagat cgttggtgga gtttacttgt tgccgcgcag
 120 gggccctaga ttgggtgtgc gcgcgacgag gaagacttcc gagcggtcgc aacctcgagg
 180 tagacgtcag cctatcccca aggcacgtcg gcccgagggc aggacctggg ctcagcccgg
 240 gtacccttgg cccctctatg gcaatgaggg ttgcgggtgg gcgggatggc tcctgtctcc
 300 ccgtggctct cggcctagct ggggccccac agacccccgg cgtaggtcgc gcaatttggg
 360 taaggtcatc gataccctta cgtgcggctt cgccgacctc atggggtaca taccgctcgt
 420 cggcgcccct cttggaggcg ctgccagggc cctggcgcat ggcgtccggg ttctggaaga
 480 cggcgtgaac tatgcaacag ggaaccttcc tggttgctct ttctctatct tccttctggc
 540 cctgctctct tgcctgactg tgcccgcttc agcctaccaa gtgcgcaatt cctcggggct
 600 ttaccatgtc accaatgatt gccctaactc gagtattgtg tacgaggcgg ccgatgccat
 660 cctgcacact ccggggtgtg tcccttgcgt tcgcgagggt aacgcctcga ggtgttgggt
 720 ggcggtgacc cccacggtgg ccaccaggga cggcaaactc cccacaacgc agcttcgacg
 780 tcatatcgat ctgcttgtcg ggagcgccac cctctgctcg gccctctacg tgggggacct
 840 gtgcgggtct gtctttcttg ttggtcaact gtttaccttc tctcccaggc gccactggac
 900 gacgcaagac tgcaattgtt ctatctatcc cggccatata acgggtcatc gcatggcatg
 960 ggatatgatg atgaactggt cccctacggc agcgttggtg gtagctcagc tgctccggat
1020 cccacaagcc atcatggaca tgatcgctgg tgctcactgg ggagtcctgg cgggcatagc
1080 gtatttctcc atggtgggga actgggcgaa ggtcctggta gtgctgctgc tatttgccgg
1140 cgtcgacgcg gaaacccacg tcaccggggg aaatgccggc cgcaccacgg ctgggcttgt
1200 tggtctcctt acaccaggcg ccaagcagaa catccaactg atcaacacca acggcagttg
1260 gcacatcaat agcacggcct tgaattgcaa tgaaagcctt aacaccggct ggttagcagg
1320 gctcttctat caacacaaat tcaactcttc aggctgtcct gagaggttgg ccagctgccg
1380 acgccttacc gattttgccc agggctgggg tcctatcagt tatgccaacg gaagcggcct
1440 cgacgaacgc ccctactgct ggcactaccc tccaagacct tgtggcattg tgcccgcaaa
1500 gagcgtgtgt ggcccggtat attgcttcac tcccagcccc gtggtggtgg gaacgaccga
1560 caggtcgggc gcgcctacct acagctgggg tgcaaatgat acggatgtct tcgtccttaa
1620 caacaccagg ccaccgctgg gcaattggtt cggttgtacc tggatgaact caactggatt
1680 caccaaagtg tgcggagcgc ccccttgtgt catcggaggg gtgggcaaca acaccttgct
1740 ctgccccact gattgcttcc gcaaacatcc ggaagccaca tactctcggt gcggctccgg
1800 tccctggatt acacccaggt gcatggtcga ctacccgtat aggctttggc actatccttg
1860 taccatcaat tacaccatat tcaaagtcag gatgtacgtg ggaggggtcg agcacaggct
1920 ggaagcggcc tgcaactgga cgcggggcga acgctgtgat ctggaagaca gggacaggtc
1980 cgagctcagc ccgttgctgc tgtccaccac acagtggcag gtccttccgt gttctttcac
2040 gaccctgcca gccttgtcca ccggcctcat ccacctccac cagaacattg tggacgtgca
2100 gtacttgtac ggggtagggt caagcatcgc gtcctgggcc attaagtggg agtacgtcgt
2160 tctcctgttc cttctgcttg cagacgcgcg cgtctgctcc tgcttgtgga tgatgttact
2220 catatcccaa gcggaggcgg ctttggagaa cctcgtaata ctcaatgcag catccctggc
2280 cgggacgcac ggtcttgtgt ccttcctcgt gttcttctgc tttgcgtggt atctgaaggg
2340 taggtgggtg cccggagcgg tctacgccct ctacgggatg tggcctctcc tcctgctcct
2400 gctggcgttg cctcagcggg catacgcac
```

Figure 2

1
MSTNPKPQRKTKRNTNRRPQDVKFPGGGQIVGGVYLLPRRGPRLGVRATRKTSERSQPRGRRQPIPKARRPE
73
GRTWAQPGYPWPLYGNEGCGWAGWLLSPRGSRPSWGPTDPRRRSRNLGKVIDTLTCGFADLMGYIPLVGAPL
145
GGAARALAHGVRVLEDGVNYATGNLPGCSFSIFLLALLSCLTVPASAYQVRNSSGLYHVTNDCPNSSIVYEA
217
ADAILHTPGCVPCVREGNASRCWVAVTPTVATRDGKLPTTQLRRHIDLLVGSATLCSALYVGDLCGSVFLVG
289
QLFTFSPRRHWTTQDCNCSIYPGHITGHRMAWDMMMNWSPTAALVVAQLLRIPQAIMDMIAGAHWGVLAGIA
361
YFSMVGNWAKVLVVLLLFAGVDAETHVTGGNAGRTTAGLVGLLTPGAKQNIQLINTNGSWHINSTALNCNES
433
LNTGWLAGLFYQHKFNSSGCPERLASCRRLTDFAQGWGPISYANGSGLDERPYCWHYPPRPCGIVPAKSVCG
505
PVYCFTPSPVVVGTTDRSGAPTYSWGANDTDVFVLNNTRPPLGNWFGCTWMNSTGFTKVCGAPPCVIGGVGN
577
NTLLCPTDCFRKHPEATYSRCGSGPWITPRCMVDYPYRLWHYPCTINYTIFKVRMYVGGVEHRLEAACNWTR
649
GERCDLEDRDRSELSPLLLSTTQWQVLPCSFTTLPALSTGLIHLHQNIVDVQYLYGVGSSIASWAIKWEYVV
721
LLFLLLADARVCSCLWMMLLISQAEAALENLVILNAASLAGTHGLVSFLVFFCFAWYLKGRWVPGAVYALYG
793
MWPLLLLLLALPQRAYALDTEVAASCGGVVLVGLMALTLSPYYKRYISWCMWWLQYFLTRVEAQLHVWVPPL
865
NVRGGRDAVILLMCVVHPTLVFDITKLLLAIFGPLWILQASLLKVPYFVRVQGLLRICALARKIAGGHYVQM
937
AIIKLGALTGTYVYNHLTPLRDWAHNGLRDLAVAVEPVVFSRMETKLITWGADTAACGDIINGLPVSARRGQ
1009
EILLGPADGMVSKGWRLLAPITAYAQQTRGLLGCIITSLTGRDKNQVEGEVQIVSTATQTFLATCINGVCWT
1081
VYHGAGTRTIASPKGPVIQMYTNVDQDLVGWPAPQGSRSLTPCTCGSSDLYLVTRHADVIPVRRRGDSRGSL
1153
LSPRPISYLKGSSGGPLLCPAGHAVGLFRAAVCTRGVAKAVDFIPVENLGTTMRSPVFTDNSSPPAVPQSFQ
1225
VAHLHAPTGSGKSTKVPAAYAAQGYKVLVLNPSVAATLGFGAYMSKAHGVDPNIRTGVRTITTGSPITYSTY
1297
GKFLADGGCSGGAYDIIICDECHSTDATSILGIGTVLDQAETAGARLVVLATATPPGSVTVSHPNIEEVALS
1369
TTGEIPFYGKAIPLEVIKGGRHLIFCHSKKKCDELAAKLVALGINAVAYYRGLDVSVIPTSGDVVVVSTDAL
1441
MTGFTGDFDSVIDCNTCVTQTVDFSLDPTFTIETTTLPQDAVSRTQRRGRTGRGKPGIYRFVAPGERPSGMF
1513
DSSVLCECYDAGCAWYELTPAETTVRLRAYMNTPGLPVCQDHLEFWEGVFTGLTHIDAHFLSQTKQSGENFP
1585
YLVAYQATVCARAQAPPPSWDQMWKCLIRLKPTLHGPTPLLYRLGAVQNEVTLTHPITKYIMTCMSADLEVV
1657
TSTWVLVGGVLAALAAYCLSTGCVVIVGRIVLSGKPAIIPDREVLYQEFDEMEECSQHLPYIEQGMMLAEQF
1729
KQKALGLLQTASRHAEVITPAVQTNWQKLEVFWAKHMWNFISGIQYLAGLSTLPGNPAIASLMAFTAAVTSP
1801
LTTGQTLLFNILGGWVAAQLAAPGAATAFVGAGLAGAAIGSVGLGKVLVDILAGYGAGVAGALVAFKIMSGE
1873
VPSTEDLVNLLPAILSPGALVVGVVCAAILRRHVGPGEGAVQWMNRLIAFASRGNHVSPTHYVPESDAAARV
1945
TAILSSLTVTQLLRRLHQWISSECTTPCSGSWLRDIWDWICEVLSDFKTWLKAKLMPQLPGIPFVSCQRGYR
2017
GVWRGDGIMHTRCHCGAEITGHVKNGTMRIVGPRTCRNMWSGTFPINAYTTGPCTPLPAPNYKFALWRVSAE
2089
EYVEIRRVGDFHYVSGMTTDNLKCPCQIPSPEFFTELDGVRLHRFAPPCKPLLREEVSFRVGLHEYPVGSQL

Figure 3a

2161
PCEPEPDVAVLTSMLTDPSHITAEAAGRRLARGSPPSMASSSASQLSAPSLKATCTANHDSPDAELIEANLL
2233
WRQEMGGNITRVESENKVVILDSFDPLVAEEDEREVSVPAEILRKSRRFARALPVWARPDYNPPLVETWKKP
2305
DYEPPVVHGCPLPPPRSPPVPPPRKKRTVVLTESTLSTALAELATKSFGSSSTSGITGDNTTTSSEPAPSGC
2377
PPDSDVESYSSMPPLEGEPGDPDLSDGSWSTVSSGADTEDVVCCSMSYSWTGALVTPCAAEEQKLPINALSN
2449
SLLRHHNLVYSTTSRSACQRQKKVTFDRLQVLDSHYQDVLKEVKAAASKVKANLLSVEEACSLTPPHSAKSK
2521
FGYGAKDVRCHARKAVAHINSVWKDLLEDSVTPIDTTIMAKNEVFCVQPEKGGRKPARLIVFPDLGVRVCEK
2593
MALYDVVSKLPLAVMGSSYGFQYSPGQRVEFLVQAWKSKKTPMGFSYDTRCFDSTVTESDIRTEEAIYQCCD
2665
LDPQARVAIKSLTERLYVGGPLTNSRGENCGYRRCRASGVLTTSCGNTLTCYIKARAACRAAGLQDCTMLVC
2737
GDDLVVICESAGVQEDAASLRAFTEAMTRYSAPPGDPPQPEYDLELITSCSSNVSVAHDGAGKRVYYLTRDP
2809
TTPLARAAWETARHTPVNSWLGNIIMFAPTLWARMILMTHFFSVLIARDQLEQALNCEIYGACYSIEPLDLP
2881
PIIQRLHGLSAFSLHSYSPGEINRVAACLRKLGVPPLRAWRHRARSVRARLLSRGGRAAICGKYLFNWAVRT
2953
KLKLTPIAAAGRLDLSGWFTAGYSGGDIYHSVSHARPRWFWFCLLLLAAGVGIYLLPNR

Figure 3b

*AAGCTT*ATGAGCACGAATCCTAAACCTCAAAGAAAAACCAAACGTAACACCAACCGTCGCCC
ACAGGACGTCAAGTTCCCGGGTGGCGGTCAGATCGTTGGTGGAGTTTACTTGTTGCCGCGCA
GGGGCCCTAGATTGGGTGTGCGCGCGACGAGGAAGACTTCCGAGCGGTCGCAACCTCGAGGT
AGACGTCAGCCTATCCCCAAGGCACGTCGGCCCGAGGGCAGGACCTGGGCTCAGCCCGGGTA
CCCTTGGCCCCTCTATGGCAATGAGGGTTGCGGGTGGGCGGGATGGCTCCTGTCTCCCCGTG
GCTCTCGGCCTAGCTGGGGCCCCACAGACCCCCGGCGTAGGTCGCGCAATTTGGGTAAGGTC
ATCGATACCCTTACGTGCGGCTTCGCCGACCTCATGGGGTACATACCGCTCGTCGGCGCCCC
TCTTGGAGGCGCTGCCAGGGCCCTGGCGCATGGCGTCCGGGTTCTGGAAGACGGCGTGAACT
ATGCAACAGGGAACCTTCCTGGTTGCTCTTTCTCTATCTTCCTTCTGGCCCTGCTCTCTTGC
CTGACCGTGCCCGCTTCAGCCTACCAAGTGCGCAATTCCTCGGGGCTTTACCATGTCACCAA
TGATTGCCCTAACTCGAGTATTGTGTACGAGGCGGCCGATGCCATCCTGCACACTCCGGGGT
GTGTCCCTTGCGTTCGCGAGGGTAACGCCTCGAGGTGTTGGGTGGCGGTGACCCCCACGGTG
GCCACCAGGGACGGCAAACTCCCCACAACGCAGCTTCGACGTCATATCGATCTGCTTGTCGG
GAGCGCCACCCTCTGCTCGGCCCTCTACGTGGGGGACCTGTGCGGGTCTGTCTTTCTTGTTG
GTCAACTGTTTACCTTCTCTCCCAGGCGCCACTGGACGACGCAAGACTGCAATTGTTCTATC
TATCCCGGCCATATAACGGGTCATCGCATGGCATGGGATATGATGATGAACTGGTCCCCTAC
GGCAGCGTTGGTGGTAGCTCAGCTGCTCCGGATCCCACAAGCCATCATGGACATGATCGCTG
GTGCTCACTGGGGAGTCCTGGCGGGCATAGCGTATTTCTCCATGGTGGGGAACTGGGCGAAG
GTCCTGGTAGTGCTGCTGCTATTTGCCGGCGTCGACGCGGAAACCCACGTCACCGGGGGAAG
TGCCGGCCGCACCACGGCTGGGCTTGTTGGTCTCCTTACACCAGGCGCCAAGCAGAACATCC
AACTGATCAACACCAACGGCAGTTGGCACATCAATAGCACGGCCTTGAACTGCAATGAAAGC
CTTAACACCGGCTGGTTAGCAGGGCTCTTCTATCAGCACAAATTCAACTCTTCAGGCTGTCC
TGAGAGGTTGGCCAGCTGCCGACGCCTTACCGATTTTGCCCAGGGCTGGGGTCCTATCAGTT
ATGCCAACGGAAGCGGCCTCGACGAACGCCCCTACTGCTGGCACTACCCTCCAAGACCTTGT
GGCATTGTGCCCGCAAAGAGCGTGTGTGGCCCGGTATATTGCTTCACTCCCAGCCCCGTGGT
GGTGGGAACGACCGACAGGTCGGGCGCGCCTACCTACAGCTGGGGTGCAAATGATACGGATG
TCTTCGTCCTTAACAACACCAGGCCACCGCTGGGCAATTGGTTCGGTTGTACCTGGATGAAC
TCAACTGGATTCACCAAAGTGTGCGGAGCGCCCCCTTGTGTCATCGGAGGGGTGGGCAACAA
CACCTTGCTCTGCCCCACTGATTGTTTCCGCAAGCATCCGGAAGCCACATACTCTCGGTGCG
GCTCCGGTCCCTGGATTACACCCAGGTGCATGGTCGACTACCCGTATAGGCTTTGGCACTAT
CCTTGTACCATCAATTACACCATATTCAAAGTCAGGATGTACGTGGGAGGGGTCGAGCACAG
GCTGGAAGCGGCCTGCAACTGGACGCGGGGCGAACGCTGTGATCTGGAAGACAGGGACAGGT
CCGAGCTCAGCCCATTGCTGCTGTCCACCACACAGTGGCAGGTCCTTCCGTGTTCTTTCACG
ACCCTGCCAGCCTTGTCCACCGGCCTCATCCACCTCCACCAGAACATTGTGGACGTGCAGTA
CTTGTACGGGGTAGGGTCAAGCATCGCGTCCTGGGCCATTAAGTGGGAGTACGTCGTTCTCC
TGTTCCTCCTGCTTGCAGACGCGCGCGTCTGCTCCTGCTTGTGGATGATGTTACTCATATCC
CAAGCGGAGGCGGCTTTGGAGAACCTCGTAATACTCAATGCAGCATCCCTGGCCGGGACGCA
CGGTCTTGTGTCCTTCCTCGTGTTCTTCTGCTTTGCGTGGTATCTGAAGGGTAGGTGGGTGC
CCGGAGCGGTCTACGCCTTCTACGGGATGTGGCCTCTCCTCCTGCTCCTGCTGGCGTTGCCT
CAGCGGGCATACGCATAA*TCTAGA*

Figure 4

*AAGCTT*ATGAGCACGAATCCTAAACCTCAAAGAAAAACCAAACGTAACACCAACCGTCGCCC
ACAGGACGTCAAGTTCCCGGGTGGCGGTCAGATCGTTGGTGGAGTTTACTTGTTGCCGCGCA
GGGGCCCTAGATTGGGTGTGCGCGCGACGAGGAAGACTTCCGAGCGGTCGCAACCTCGAGGT
AGACGTCAGCCTATCCCCAAGGCACGTCGGCCCGAGGGCAGGACCTGGGCTCAGCCCGGGTA
CCCTTGGCCCCTCTATGGCAATGAGGGTTGCGGGTGGGCGGGATGGCTCCTGTCTCCCCGTG
GCTCTCGGCCTAGCTGGGGCCCCACAGACCCCCGGCGTAGGTCGCGCAATTTGGGTAAGGTC
ATCGATACCCTTACGTGCGGCTTCGCCGACCTCATGGGGTACATACCGCTCGTCGGCGCCCC
TCTTGGAGGCGCTGCCAGGGCCCTGGCGCATGGCGTCCGGGTTCTGGAAGACGGCGTGAACT
ATGCAACAGGGAACCTTCCTGGTTGCTCTTTCTCTATCTTCCTTCTGGCCCTGCTCTCTTGC
CTGACCGTGCCCGCTTCAGCCTACCAAGTGCGCAATTCCTCGGGGCTTTACCATGTCACCAA
TGATTGCCCTAACTCGAGTATTGTGTACGAGGCGGCCGATGCCATCCTGCACACTCCGGGGT
GTGTCCCTTGCGTTCGCGAGGGTAACGCCTCGAGGTGTTGGGTGGCGGTGACCCCCACGGTG
GCCACCAGGGACGGCAAACTCCCCACAACGCAGCTTCGACGTCATATCGATCTGCTTGTCGG
GAGCGCCACCCTCTGCTCGGCCCTCTACGTGGGGGACCTGTGCGGGTCTGTCTTTCTTGTTG
GTCAACTGTTTACCTTCTCTCCCAGGCGCCACTGGACGACGCAAGACTGCAATTGTTCTATC
TATCCCGGCCATATAACGGGTCATCGCATGGCATGGGATATGATGATGAACTGGTCCCCTAC
GGCAGCGTTGGTGGTAGCTCAGCTGCTCCGGATCCCACAAGCCATCATGGACATGATCGCTG
GTGCTCACTGGGGAGTCCTGGCGGGCATAGCGTATTTCTCCATGGTGGGGAACTGGGCGAAG
GTCCTGGTAGTGCTGCTGCTATTTGCCGGCGTCGACGCGGAAACCCACGTCACCGGGGGAAG
TGCCGGCCGCACCACGGCTGGGCTTGTTGGTCTCCTTACACCAGGCGCCAAGCAGAACATCC
AACTGATCAACACCAACGGCAGTTGGCACATCAATAGCACGGCCTTGAACTGCAATGAAAGC
CTTAACACCGGCTGGTTAGCAGGGCTCTTCTATCAGCACAAATTCAACTCTTCAGGCTGTCC
TGAGAGGTTGGCCAGCTGCCGACGCCTTACCGATTTTGCCCAGGGCTGGGGTCCTATCAGTT
ATGCCAACGGAAGCGGCCTCGACGAACGCCCCTACTGCTGGCACTACCCTCCAAGACCTTGT
GGCATTGTGCCCGCAAAGAGCGTGTGTGGCCCGGTATATTGCTTCACTCCCAGCCCCGTGGT
GGTGGGAACGACCGACAGGTCGGGCGCGCCTACCTACAGCTGGGGTGCAAATGATACGGATG
TCTTCGTCCTTAACAACACCAGGCCACCGCTGGGCAATTGGTTCGGTTGTACCTGGATGAAC
TCAACTGGATTCACCAAAGTGTGCGGAGCGCCCCCTTGTGTCATCGGAGGGGTGGGCAACAA
CACCTTGCTCTGCCCCACTGATTGTTTCCGCAAGCATCCGGAAGCCACATACTCTCGGTGCG
GCTCCGGTCCCTGGATTACACCCAGGTGCATGGTCGACTACCCGTATAGGCTTTGGCACTAT
CCTTGTACCATCAATTACACCATATTCAAAGTCAGGATGTACGTGGGAGGGGTCGAGCACAG
GCTGGAAGCGGCCTGCAACTGGACGCGGGGCGAACGCTGTGATCTGGAAGACAGGGACAGGT
CCGAGCTCAGCCCATTGCTGCTGTCCACCACACAGTGGCAGGTCCTTCCGTGTTCTTTCACG
ACCCTGCCAGCCTTGTCCACCGGCCTCATCCACCTCCACCAGAACATTGTGGACGTGCAGTA
CTTGTACGGGGTAGGGTCAAGCATCGCGTCCTGGGCCATTAAGTGGGAGTACGTCGTTCTCC
TGTTCCTCCTGCTTGCAGACGCGCGCGTCTGCTCCTGCTTGTGGATGATGTTACTCATATCC
CAAGCGGAGGCGTAA*TCTAGA*

Figure 5

*AAGCTT*ATGGACCTCATGGGGTACATACCGCTCGTCGGCGCCCCTCTTGGAGGCGCTGCCAG
GGCCCTGGCGCATGGCGTCCGGGTTCTGGAAGACGGCGTGAACTATGCAACAGGGAACCTTC
CTGGTTGCTCTTTCTCTATCTTCCTTCTGGCCCTGCTCTCTTGCCTGACCGTGCCCGCTTCA
GCCTACCAAGTGCGCAATTCCTCGGGGCTTTACCATGTCACCAATGATTGCCCTAACTCGAG
TATTGTGTACGAGGCGGCCGATGCCATCCTGCACACTCCGGGGTGTGTCCCTTGCGTTCGCG
AGGGTAACGCCTCGAGGTGTTGGGTGGCGGTGACCCCCACGGTGGCCACCAGGGACGGCAAA
CTCCCCACAACGCAGCTTCGACGTCATATCGATCTGCTTGTCGGGAGCGCCACCCTCTGCTC
GGCCCTCTACGTGGGGGACCTGTGCGGGTCTGTCTTTCTTGTTGGTCAACTGTTTACCTTCT
CTCCCCGTCGCCACTGGACGACGCAAGACTGCAATTGTTCTATCTATCCCGGCCATATAACG
GGTCATCGCATGGCATGGGATATGATGATGAACTGGTCCCCTACGGCAGCGTTGGTGGTAGC
TCAGCTGCTCCGGATCCCACAAGCCATCATGGACATGATCGCTGGTGCTCACTGGGGAGTCC
TGGCGGGCATAGCGTATTTCTCCATGGTGGGGAACTGGGCGAAGGTCCTGGTAGTGCTGCTG
CTATTTGCCGGCGTCGACGCGGAAACCCACGTCACCGGGGGAAGTGCCGGCCGCACCACGGC
TGGGCTTGTTGGTCTCCTTACACCAGGCGCCAAGCAGAACATCCAACTGATCAACACCAACG
GCAGTTGGCACATCAATAGCACGGCCTTGAACTGCAATGAAAGCCTTAACACCGGCTGGTTA
GCAGGGCTCTTCTATCAGCACAAATTCAACTCTTCAGGCTGTCCTGAGAGGTTGGCCAGCTG
CCGACGCCTTACCGATTTTGCCCAGGGCTGGGGTCCTATCAGTTATGCCAACGGAAGCGGCC
TCGACGAACGCCCCTACTGCTGGCACTACCCTCCAAGACCTTGTGGCATTGTGCCCGCAAAG
AGCGTGTGTGGCCCGGTATATTGCTTCACTCCCAGCCCCGTGGTGGTGGGAACGACCGACAG
GTCGGGCGCGCCTACCTACAGCTGGGgTGCAAATGATACGGATGTCTTCGTCCTTAACAACA
CCAGGCCACCGCTGGGCAATTGGTTCGGTTGTACCTGGATGAACTCAACTGGATTCACCAAA
GTGTGCGGAGCGCCCCCTTGTGTCATCGGAGGGGTGGGCAACAACACCTTGCTCTGCCCCAC
TGATTGTTTCCGCAAGCATCCGGAAGCCACATACTCTCGGTGCGGCTCCGGTCCCTGGATTA
CACCCAGGTGCATGGTCGACTACCCGTATAGGCTTTGGCACTATCCTTGTACCATCAATTAC
ACCATATTCAAAGTCAGGATGTACGTGGGAGGGGTCGAGCACAGGCTGGAAGCGGCCTGCAA
CTGGACGCGGGGCGAACGCTGTGATCTGGAAGACAGGGACAGGTCCGAGCTCAGCCCATTGC
TGCTGTCCACCACACAGTGGCAGGTCCTTCCGTGTTCTTTCACGACCCTGCCAGCCTTGTCC
ACCGGCCTCATCCACCTCCACCAGAACATTGTGGACGTGCAGTACTTGTACGGGGTAGGGTC
AAGCATCGCGTCCTGGGCCATTAAGTGGGAGTACGTCGTTCTCCTGTTCCTCCTGCTTGCTG
ACGCGCGCGTCTGCTCCTGCTTGTGGATGATGTTACTCATATCCCAAGCGGAGGCGTAA*TCT
AGA*

Figure 6

*AAGCTT*ATGGGTTGCTCTTTCTCTATCTTCCTTCTGGCCCTGCTCTCTTGCCTGACCGTGCC
CGCTTCAGCCTACCAAGTGCGCAATTCCTCGGGGCTTTACCATGTCACCAATGATTGCCCTA
ACTCGAGTATTGTGTACGAGGCGGCCGATGCCATCCTGCACACTCCGGGGTGTGTCCCTTGC
GTTCGCGAGGGTAACGCCTCGAGGTGTTGGGTGGCGGTGACCCCCACGGTGGCCACCAGGGA
CGGCAAACTCCCCACAACGCAGCTTCGACGTCATATCGATCTGCTTGTCGGGAGCGCCACCC
TCTGCTCGGCCCTCTACGTGGGGGACCTGTGCGGGTCTGTCTTTCTTGTTGGTCAACTGTTT
ACCTTCTCTCCCAGGCGCCACTGGACGACGCAAGACTGCAATTGTTCTATCTATCCCGGCCA
TATAACGGGTCATCGCATGGCATGGGATATGATGATGAACTGGTCCCCTACGGCAGCGTTGG
TGGTAGCTCAGCTGCTCCGGATCCCACAAGCCATCATGGACATGATCGCTGGTGCTCACTGG
GGAGTCCTGGCGGGCATAGCGTATTTCTCCATGGTGGGGAACTGGGCGAAGGTCCTGGTAGT
GCTGCTGCTATTTGCCGGCGTCGACGCGGAAACCCACGTCACCGGGGGAAGTGCCGGCCGCA
CCACGGCTGGGCTTGTTGGTCTCCTTACACCAGGCGCCAAGCAGAACATCCAACTGATCAAC
ACCAACGGCAGTTGGCACATCAATAGCACGGCCTTGAACTGCAATGAAAGCCTTAACACCGG
CTGGTTAGCAGGGCTCTTCTATCAGCACAAATTCAACTCTTCAGGCTGTCCTGAGAGGTTGG
CCAGCTGCCGACGCCTTACCGATTTTGCCCAGGGCTGGGGTCCTATCAGTTATGCCAACGGA
AGCGGCCTCGACGAACGCCCCTACTGCTGGCACTACCCTCCAAGACCTTGTGGCATTGTGCC
CGCAAAGAGCGTGTGTGGCCCGGTATATTGCTTCACTCCCAGCCCCGTGGTGGTGGGAACGA
CCGACAGGTCGGGCGCGCCTACCTACAGCTGGGGTGCAAATGATACGGATGTCTTCGTCCTT
AACAACACCAGGCCACCGCTGGGCAATTGGTTCGGTTGTACCTGGATGAACTCAACTGGATT
CACCAAAGTGTGCGGAGCGCCCCCTTGTGTCATCGGAGGGGTGGGCAACAACACCTTGCTCT
GCCCCACTGATTGTTTCCGCAAGCATCCGGAAGCCACATACTCTCGGTGCGGCTCCGGTCCC
TGGATTACACCCAGGTGCATGGTCGACTACCCGTATAGGCTTTGGCACTATCCTTGTACCAT
CAATTACACCATATTCAAAGTCAGGATGTACGTGGGAGGGGTCGAGCACAGGCTGGAAGCGG
CCTGCAACTGGACGCGGGGCGAACGCTGTGATCTGGAAGACAGGGACAGGTCCGAGCTCAGC
CCATTGCTGCTGTCCACCACACAGTGGCAGGTCCTTCCGTGTTCTTTCACGACCCTGCCAGC
CTTGTCCACCGGCCTCATCCACCTCCACCAGAACATTGTGGACGTGCAGTACTTGTACGGGG
TAGGGTCAAGCATCGCGTCCTGGGCCATTAAGTGGGAGTACGTCGTTCTCCTGTTCCTCCTG
CTTGCAGACGCGCGCGTCTGCTCCTGCTTGTGGATGATGTTACTCATATCCCAAGCGGAGGC
GGCTTTGGAGAACCTCGTAATACTCAATGCAGCATCCCTGGCCGGGACGCACGGTCTTGTGT
CCTTCCTCGTGTTCTTCTGCTTTGCGTGGTATCTGAAGGGTAGGTGGGTGCCCGGAGCGGTC
TACGCCTTCTACGGGATGTGGCCTCTCCTCCTGCTCCTGCTGGCGTTGCCTCAGCGGGCATA
CGCATAA*TCTAGA*

Figure 7

*AAGCTT*ATGGGTTGCTCTTTCTCTATCTTCCTTCTGGCCCTGCTCTCTTGCCTGACCGTGCC
CGCTTCAGCCTACCAAGTGCGCAATTCCTCGGGGCTTTACCATGTCACCAATGATTGCCCTA
ACTCGAGTATTGTGTACGAGGCGGCCGATGCCATCCTGCACACTCCGGGGTGTGTCCCTTGC
GTTCGCGAGGGTAACGCCTCGAGGTGTTGGGTGGCGGTGACCCCCACGGTGGCCACCAGGGA
CGGCAAACTCCCCACAACGCAGCTTCGACGTCATATCGATCTGCTTGTCGGGAGCGCCACCC
TCTGCTCGGCCCTCTACGTGGGGGACCTGTGCGGGTCTGTCTTTCTTGTTGGTCAACTGTTT
ACCTTCTCTCCCAGGCGCCACTGGACGACGCAAGACTGCAATTGTTCTATCTATCCCGGCCA
TATAACGGGTCATCGCATGGCATGGGATATGATGATGAACTGGTCCCCTACGGCAGCGTTGG
TGGTAGCTCAGCTGCTCCGGATCCCACAAGCCATCATGGACATGATCGCTGGTGCTCACTGG
GGAGTCCTGGCGGGCATAGCGTATTTCTCCATGGTGGGGAACTGGGCGAAGGTCCTGGTAGT
GCTGCTGCTATTTGCCGGCGTCGACGCGGAAACCCACGTCACCGGGGGAAGTGCCGGCCGCA
CCACGGCTGGGCTTGTTGGTCTCCTTACACCAGGCGCCAAGCAGAACATCCAACTGATCAAC
ACCAACGGCAGTTGGCACATCAATAGCACGGCCTTGAACTGCAATGAAAGCCTTAACACCGG
CTGGTTAGCAGGGCTCTTCTATCAGCACAAATTCAACTCTTCAGGCTGTCCTGAGAGGTTGG
CCAGCTGCCGACGCCTTACCGATTTTGCCCAGGGCTGGGGTCCTATCAGTTATGCCAACGGA
AGCGGCCTCGACGAACGCCCCTACTGCTGGCACTACCCTCCAAGACCTTGTGGCATTGTGCC
CGCAAAGAGCGTGTGTGGCCCGGTATATTGCTTCACTCCCAGCCCCGTGGTGGTGGGAACGA
CCGACAGGTCGGGCGCGCCTACCTACAGCTGGGGTGCAAATGATACGGATGTCTTCGTCCTT
AACAACACCAGGCCACCGCTGGGCAATTGGTTCGGTTGTACCTGGATGAACTCAACTGGATT
CACCAAAGTGTGCGGAGCGCCCCCTTGTGTCATCGGAGGGGTGGGCAACAACACCTTGCTCT
GCCCCACTGATTGTTTCCGCAAGCATCCGGAAGCCACATACTCTCGGTGCGGCTCCGGTCCC
TGGATTACACCCAGGTGCATGGTCGACTACCCGTATAGGCTTTGGCACTATCCTTGTACCAT
CAATTACACCATATTCAAAGTCAGGATGTACGTGGGAGGGGTCGAGCACAGGCTGGAAGCGG
CCTGCAACTGGACGCGGGGCGAACGCTGTGATCTGGAAGACAGGGACAGGTCCGAGCTCAGC
CCATTGCTGCTGTCCACCACACAGTGGCAGGTCCTTCCGTGTTCTTTCACGACCCTGCCAGC
CTTGTCCACCGGCCTCATCCACCTCCACCAGAACATTGTGGACGTGCAGTACTTGTACGGGG
TAGGGTCAAGCATCGCGTCCTGGGCCATTAAGTGGGAGTACGTCGTTCTCCTGTTCCTCCTG
CTTGCAGACGCGCGCGTCTGCTCCTGCTTGTGGATGATGTTACTCATATCCCAAGCGGAGGC
GTAA*TCTAGA*

Figure 8

*AAGCTT*ATGGGTTGCTCTTTCTCTATCTTCCTTCTGGCCCTGCTCTCTTGCCTGACCGTGCC
CGCTTCAGCCTACCAAGTGCGCAATTCCTCGGGGCTTTACCATGTCACCAATGATTGCCCTA
ACTCGAGTATTGTGTACGAGGCGGCCGATGCCATCCTGCACACTCCGGGGTGTGTCCCTTGC
GTTCGCGAGGGTAACGCCTCGAGGTGTTGGGTGGCGGTGACCCCCACGGTGGCCACCAGGGA
CGGCAAACTCCCCACAACGCAGCTTCGACGTCATATCGATCTGCTTGTCGGGAGCGCCACCC
TCTGCTCGGCCCTCTACGTGGGGGACCTGTGCGGGTCTGTCTTTCTTGTTGGTCAACTGTTT
ACCTTCTCTCCCC(886)GGCGCCACTGGACGACGCAAGACTGCAATTGTTCTATCTATCCC
GGCCATATAACGGGTCATCGCATGGCATGGGATATGATGATGAACTGGTCCCCTACGGCAGC
GTTGGTGGTAGCTCAGCTGCTCCGGATCCCACAAGCCATCATGGACATGATCGCTGGTGCTC
ACTGGGGAGTCCTGGCGGGCATAGCGTATTTCTCCATGGTGGGGAACTGGGCGAAGGTCCTG
GTAGTGCTGCTGCTATTTGCCGGCGTCGACGCGGAAACCCACGTCACCGGGGGAAGTGCCGG
CCGCACCACGGCTGGGCTTGTTGGTCTCCTTACACCAGGCGCCAAGCAGAACATCCAACTGA
TCAACACCAACGGCAGTTGGCACATCAATAGCACGGCCTTGAACTGCAATGAAAGCCTTAAC
ACCGGCTGGTTAGCAGGGCTCTTCTATCAGCACAAATTCAACTCTTCAGGCTGTCCTGAGAG
GTTGGCCAGCTGCCGACGCCTTACCGATTTTGCCCAGGGCTGGGGTCCTATCAGTTATGCCA
ACGGAAGCGGCCTCGACGAACGCCCCTACTGCTGGCACTACCCTCCAAGACCTTGTGGCATT
GTGCCCGCAAAGAGCGTGTGTGGCCCGGTATATTGCTTCACTCCCAGCCCCGTGGTGGTGGG
AACGACCGACAGGTCGGGCGCGCCTACCTACAGCTGGGGTGCAAATGATACGGATGTCTTCG
TCCTTAACAACACCAGGCCACCGCTGGGCAATTGGTTCGGTTGTACCTGGATGAACTCAACT
GGATTCACCAAAGTGTGCGGAGCGCCCCCTTGTGTCATCGGAGGGGTGGGCAACAACACCTT
GCTCTGCCCCACTGATTGTTTCCGCAAGCATCCGGAAGCCACATACTCTCGGTGCGGCTCCG
GTCCCTGGATTACACCCAGGTGCATGGTCGACTACCCGTATAGGCTTTGGCACTATCCTTGT
ACCATCAATTACACCATATTCAAAGTCAGGATGTACGTGGGAGGGGTCGAGCACAGGCTGGA
AGCGGCCTGCAACTGGACGCGGGGCGAACGCTGTGATCTGGAAGACAGGGACAGGTCCGAGC
TCAGCCCATTGCTGCTGTCCACCACACAGTGGCAGGTCCTTCCGTGTTCTTTCACGACCCTG
CCAGCCTTGTCCACCGGCCTCATCCACCTCCACCAGAACATTGTGGACGTGCAGTACTTGTA
CGGGGTAGGGTCAAGCATCGCGTCCTGGGCCATTAAGTGGGAGTACGTCGTTCTCCTGTTCC
TCCTGCTTGCT(2183)GACGCGCGCGTCTGCTCCTGCTTGTGGATGATGTTACTCATATCC
CAAGCGGAGGCGGCTTTGGAGAACCTCGTAATACTCAATGCAGCATCCCTGGCCGGGACGCA
CGGTCTTGTGTCCTTCCTCGTGTTCTTCTGCTTTGCGTGGTATCTGAAGGGTAGGTGGGTGC
CCGGAGCGGTCTACGCCTTCTACGGGATGTGGCCTCTCCTCCTGCTCCTGCTGGCGTTGCCT
CAGCGGGCATACGCATAA*TCTAGA*

Figure 9

*AAGCTT*ATGGGTTGCTCTTTCTCTATCTTCCTTCTGGCCCTGCTCTCTTGCCTGACCGTGCC
CGCTTCAGCCTACCAAGTGCGCAATTCCTCGGGGCTTTACCATGTCACCAATGATTGCCCTA
ACTCGAGTATTGTGTACGAGGCGGCCGATGCCATCCTGCACACTCCGGGGCGCCACTGGACG
ACGCAAGACTGCAATTGTTCTATCTATCCCGGCCATATAACGGGTCATCGCATGGCATGGGA
TATGATGATGAACTGGTCCCCTACGGCAGCGTTGGTGGTAGCTCAGCTGCTCCGGATCCCAC
AAGCCATCATGGACATGATCGCTGGTGCTCACTGGGGAGTCCTGGCGGGCATAGCGTATTTC
TCCATGGTGGGGAACTGGGCGAAGGTCCTGGTAGTGCTGCTGCTATTTGCCGGCGTCGACGC
GTAA*TCTAGA*

Figure 10 a
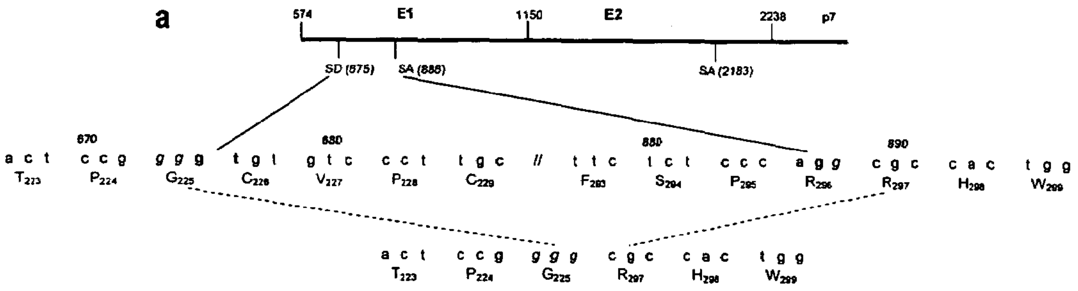
b
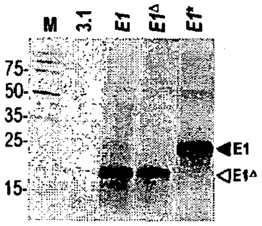
Figure 13

SEQUENCE LISTING

```
<160> NUMBER OF SEQ ID NOS: 20

<210> SEQ ID NO 1
<211> LENGTH: 9599
<212> TYPE: DNA
<213> ORGANISM: Hepatitis C virus

<400> SEQUENCE: 1

gccagccccc tgatgggggc gacactccac catgaatcac tcccctgtga ggaactactg      60

tcttcacgca gaaagcgtct agccatggcg ttagtatgag tgtcgtgcag cctccaggac     120

ccccccctccc gggagagcca tagtggtctg cggaaccggt gagtacaccg gaattgccag    180

gacgaccggg tcctttcttg gataaacccg ctcaatgcct ggagatttgg gcgtgccccc     240
```

-continued

```
gcaagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gtcgcccaca ggacgtcaag ttcccgggtg    420
gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgagggc aggacctggg ctcagcccgg gtacccttgg cccctctatg    600
gcaatgaggg ttgcgggtgg gcgggatggc tcctgtctcc ccgtggctct cggcctagct    660
ggggccccac agacccccgg cgtaggtcgc gcaatttggg taaggtcatc gataccctta    720
cgtgcggctt cgccgacctc atggggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaactc gagtattgtg tacgaggcgg ccgatgccat cctgcacact ccggggtgtg   1020
tcccttgcgt tcgcgagggt aacgcctcga ggtgttgggt ggcggtgacc cccacggtgg   1080
ccaccaggga cggcaaactc cccacaacgc agcttcgacg tcatatcgat ctgcttgtcg   1140
ggagcgccac cctctgctcg gccctctacg tgggggacct gtgcgggtct gtctttcttg   1200
ttggtcaact gtttaccttc tctcccaggc gccactggac gacgcaagac tgcaattgtt   1260
ctatctatcc cggccatata acgggtcatc gcatggcatg ggatatgatg atgaactggt   1320
cccctacggc agcgttggtg gtagctcagc tgctccggat cccacaagcc atcatggaca   1380
tgatcgctgg tgctcactgg ggagtcctgg cgggcatagc gtatttctcc atggtgggga   1440
actgggcgaa ggtcctggta gtgctgctgc tatttgccgg cgtcgacgcg gaaacccacg   1500
tcaccggggg aaatgccggc cgcaccacgg ctgggcttgt tggtctcctt acaccaggcg   1560
ccaagcagaa catccaactg atcaacacca acggcagttg gcacatcaat agcacggcct   1620
tgaattgcaa tgaaagcctt aacaccggct ggttagcagg gctcttctat caacacaaat   1680
tcaactcttc aggctgtcct gagaggttgg ccagctgccg acgccttacc gattttgccc   1740
agggctgggg tcctatcagt tatgccaacg gaagcggcct cgacgaacgc ccctactgct   1800
ggcactaccc tccaagacct tgtggcattg tgcccgcaaa gagcgtgtgt ggcccggtat   1860
attgcttcac tcccagcccc gtggtggtgg gaacgaccga caggtcgggc gcgcctacct   1920
acagctgggg tgcaaatgat acggatgtct tcgtccttaa caacaccagg ccaccgctgg   1980
gcaattggtt cggttgtacc tggatgaact caactggatt caccaaagtg tgcggagcgc   2040
ccccttgtgt catcggaggg gtgggcaaca acaccttgct ctgccccact gattgcttcc   2100
gcaaacatcc ggaagccaca tactctcggt gcggctccgg tccctggatt acacccaggt   2160
gcatggtcga ctacccgtat aggctttggc actatccttg taccatcaat tacaccatat   2220
tcaaagtcag gatgtacgtg ggaggggtcg agcacaggct ggaagcggcc tgcaactgga   2280
cgcggggcga acgctgtgat ctggaagaca gggacaggtc cgagctcagc ccgttgctgc   2340
tgtccaccac acagtggcag gtccttccgt gttctttcac gaccctgcca gccttgtcca   2400
ccggcctcat ccacctccac cagaacattg tggacgtgca gtacttgtac ggggtagggt   2460
caagcatcgc gtcctgggcc attaagtggg agtacgtcgt tctcctgttc cttctgcttg   2520
cagacgcgcg cgtctgctcc tgcttgtgga tgatgttact catatcccaa gcggaggcgg   2580
ctttggagaa cctcgtaata ctcaatgcag catccctggc cgggacgcac ggtcttgtgt   2640
```

-continued

```
ccttcctcgt gttcttctgc tttgcgtggt atctgaaggg taggtgggtg cccggagcgg   2700
tctacgccct ctacgggatg tggcctctcc tcctgctcct gctggcgttg cctcagcggg   2760
catacgcact ggacacggag gtggccgcgt cgtgtggcgg cgttgttctt gtcgggttaa   2820
tggcgctgac tctgtcgcca tattacaagc gctatatcag ctggtgcatg tggtggcttc   2880
agtattttct gaccagagta gaagcgcaac tgcacgtgtg ggttcccccc ctcaacgtcc   2940
ggggggggcg cgatgccgtc atcttactca tgtgtgtagt acacccgacc ctggtatttg   3000
acatcaccaa actactcctg gccatcttcg gacccctttg gattcttcaa gccagtttgc   3060
ttaaagtccc ctacttcgtg cgcgttcaag gccttctccg gatctgcgcg ctagcgcgga   3120
agatagccgg aggtcattac gtgcaaatgg ccatcatcaa gttaggggcg cttactggca   3180
cctatgtgta taaccatctc acccctcttc gagactgggc gcacaacggc ctgcgagatc   3240
tggccgtggc tgtggaacca gtcgtcttct cccgaatgga gaccaagctc atcacgtggg   3300
gggcagatac cgccgcgtgc ggtgacatca tcaacggctt gcccgtctct gcccgtaggg   3360
gccaggagat actgcttggg ccagccgacg gaatggtctc caaggggtgg aggttgctgg   3420
cgcccatcac ggcgtacgcc cagcagacga gaggcctcct agggtgtata atcaccagcc   3480
tgactggccg ggacaaaaac caagtggagg gtgaggtcca gatcgtgtca actgctaccc   3540
aaaccttcct ggcaacgtgc atcaatgggg tatgctggac tgtctaccac ggggccggaa   3600
cgaggaccat cgcatcaccc aagggtcctg tcatccagat gtataccaat gtggaccaag   3660
accttgtggg ctggcccgct cctcaaggtt cccgctcatt gacaccctgt acctgcggct   3720
cctcggacct ttacctggtc acgaggcacg ccgatgtcat tcccgtgcgc cggcgaggtg   3780
atagcagggg tagcctgctt tcgccccggc ccatttccta cttgaaaggc tcctcggggg   3840
gtccgctgtt gtgccccgcg ggacacgccg tgggcctatt cagggccgcg gtgtgcaccc   3900
gtggagtggc taaagcggtg gactttatcc ctgtggagaa cctagggaca accatgagat   3960
ccccggtgtt cacggacaac tcctctccac cagcagtgcc ccagagcttc caggtggccc   4020
acctgcatgc tcccaccggc agcggtaaga gcaccaaggt cccggctgcg tacgcagccc   4080
agggctacaa ggtgttggtg ctcaacccct ctgttgctgc aacgctgggc tttggtgctt   4140
acatgtccaa ggcccatggg gttgatccta atatcaggac cggggtgaga acaattacca   4200
ctggcagccc catcacgtac tccacctacg gcaagttcct tgccgacggc gggtgctcag   4260
gaggtgctta tgacataata atttgtgacg agtgccactc cacggatgcc acatccatct   4320
tgggcatcgg cactgtcctt gaccaagcag agactgcggg ggcgagactg gttgtgctcg   4380
ccactgctac ccctccgggc tccgtcactg tgtcccatcc taacatcgag gaggttgctc   4440
tgtccaccac cggagagatc ccctttttacg gcaaggctat cccccctcgag gtgatcaagg   4500
ggggaagaca tctcatcttc tgccactcaa agaagaagtg cgacgagctc gccgcgaagc   4560
tggtcgcatt gggcatcaat gccgtggcct actaccgcgg tcttgacgtg tctgtcatcc   4620
cgaccagcgg cgatgttgtc gtcgtgtcga ccgatgctct catgactggc tttaccggcg   4680
acttcgactc tgtgatagac tgcaacacgt gtgtcactca gacagtcgat ttcagccttg   4740
accctacctt taccattgag acaaccacgc tcccccagga tgctgtctcc aggactcaac   4800
gccggggcag gactggcagg gggaagccag gcatctatag atttgtggca ccgggggagc   4860
gcccctccgg catgttcgac tcgtccgtcc tctgtgagtg ctatgacgcg ggctgtgctt   4920
ggtatgagct cacgcccgcc gagactacag ttaggctacg agcgtacatg aacaccccgg   4980
```

-continued

```
ggcttcccgt gtgccaggac catcttgaat tttgggaggg cgtctttacg ggcctcactc   5040
atatagatgc ccacttttta tcccagacaa agcagagtgg ggagaacttt ccttacctgg   5100
tagcgtacca agccaccgtg tgcgctaggg ctcaagcccc tcccccatcg tgggaccaga   5160
tgtggaagtg tttgatccgc cttaaaccca ccctccatgg gccaacaccc ctgctataca   5220
gactgggcgc tgttcagaat gaagtcaccc tgacgcaccc aatcaccaaa tacatcatga   5280
catgcatgtc ggccgacctg gaggtcgtca cgagcacctg ggtgctcgtt ggcggcgtcc   5340
tggctgctct ggccgcgtat tgcctgtcaa caggctgcgt ggtcatagtg ggcaggatcg   5400
tcttgtccgg gaagccggca attatacctg acagggaggt tctctaccag gagttcgatg   5460
agatggaaga gtgctctcag cacttaccgt acatcgagca agggatgatg ctcgctgagc   5520
agttcaagca gaaggccctc ggcctcctgc agaccgcgtc ccgccatgca gaggttatca   5580
cccctgctgt ccagaccaac tggcagaaac tcgaggtctt ttgggcgaag cacatgtgga   5640
atttcatcag tgggatacaa tacttggcgg gcctgtcaac gctgcctggt aaccccgcca   5700
ttgcttcatt gatggctttt acagctgccg tcaccagccc actaaccact ggccaaaccc   5760
tcctcttcaa catattgggg gggtgggtgg ctgcccagct cgccgccccc ggtgccgcta   5820
ctgcctttgt gggtgctggc ctagctggcg ccgccatcgg cagcgttgga ctggggaagg   5880
tcctcgtgga cattcttgca gggtatggcg cgggcgtggc gggagctctt gtagcattca   5940
agatcatgag cggtgaggtc ccctccacgg aggacctggt caatctgctg cccgccatcc   6000
tctcgcctgg agcccttgta gtcggtgtgg tctgcgcagc aatactgcgc cggcacgttg   6060
gcccgggcga gggggcagtg caatggatga accggctaat agccttcgcc tcccgggga    6120
accatgtttc ccccacgcac tacgtgccgg agagcgatgc agccgcccgc gtcactgcca   6180
tactcagcag cctcactgta acccagctcc tgaggcgact gcatcagtgg ataagctcgg   6240
agtgtaccac tccatgctcc ggttcctggc taagggacat ctgggactgg atatgcgagg   6300
tgctgagcga ctttaagacc tggctgaaag ccaagctcat gccacaactg cctgggattc   6360
cctttgtgtc ctgccagcgc gggtataggg ggtctggcg aggagacggc attatgcaca    6420
ctcgctgcca ctgtggagct gagatcactg gacatgtcaa aaacgggacg atgaggatcg   6480
tcggtcctag gacctgcagg aacatgtgga gtgggacgtt ccccattaac gcctacacca   6540
cgggcccctg tactcccctt cctgcgccga actataagtt cgcgctgtgg agggtgtctg   6600
cagaggaata cgtggagata aggcgggtgg gggacttcca ctacgtatcg ggtatgacta   6660
ctgacaatct taaatgcccg tgccagatcc catcgcccga atttttcaca gaattggacg   6720
gggtgcgcct acacaggttt gcgccccctt gcaagccctt gctgcgggag gaggtatcat   6780
tcagagtagg actccacgag tacccggtgg ggtcgcaatt accttgcgag cccgaaccgg   6840
acgtagccgt gttgacgtcc atgctcactg atccctccca tataacagca gaggcggccg   6900
ggagaaggtt ggcgagaggg tcaccccctt ctatggccag ctcctcggct agccagctgt   6960
ccgctccatc tctcaaggca acttgcaccg ccaaccatga ctcccctgac gccgagctca   7020
tagaggctaa cctcctgtgg aggcaggaga tgggcggcaa catcaccagg gttgagtcag   7080
agaacaaagt ggtgattctg gactccttcg atccgcttgt ggcagaggag gatgagcggg   7140
aggtctccgt acctgcagaa attctgcgga agtctcggag attcgcccgg gccctgcccg   7200
tctgggcgcg gccggactac aaccccccgc tagtagagac gtggaaaaag cctgactacg   7260
aaccacctgt ggtccatggc tgcccgctac cacctccacg gtcccctcct gtgcctccgc   7320
ctcggaaaaa gcgtacggtg gtcctcaccg aatcaaccct atctactgcc ttggccgagc   7380
```

-continued

```
ttgccaccaa aagttttggc agctcctcaa cttccggcat tacgggcgac aatacgacaa   7440
catcctctga gcccgcccct tctggctgcc cccccgactc cgacgttgag tcctattctt   7500
ccatgccccc cctggagggg gagcctgggg atccggatct cagcgacggg tcatggtcga   7560
cggtcagtag tggggccgac acggaagatg tcgtgtgctg ctcaatgtct tattcctgga   7620
caggcgcact cgtcaccccg tgcgctgcgg aagaacaaaa actgcccatc aacgcactga   7680
gcaactcgtt gctacgccat cacaatctgg tgtattccac cacttcacgc agtgcttgcc   7740
aaaggcagaa gaaagtcaca tttgacagac tgcaagttct ggacagccat taccaggacg   7800
tgctcaagga ggtcaaagca gcggcgtcaa aagtgaaggc taacttgcta tccgtagagg   7860
aagcttgcag cctgacgccc ccacattcag ccaaatccaa gtttggctat ggggcaaaag   7920
acgtccgttg ccatgccaga aaggccgtag cccacatcaa ctccgtgtgg aaagaccttc   7980
tggaagacag tgtaacacca atagacacta ccatcatggc caagaacgag gttttctgcg   8040
ttcagcctga gaagggggt cgtaagccag ctcgtctcat cgtgttcccc gacctgggcg   8100
tgcgcgtgtg cgagaagatg gccctgtacg acgtggttag caagctcccc ctggccgtga   8160
tgggaagctc ctacggattc caatactcac caggacagcg ggttgaattc ctcgtgcaag   8220
cgtggaagtc caagaagacc ccgatggggt tctcgtatga tacccgctgt tttgactcca   8280
cagtcactga gagcgacatc cgtacggagg aggcaattta ccaatgttgt gacctggacc   8340
cccaagcccg cgtggccatc aagtccctca ctgagaggct ttatgttggg ggccctctta   8400
ccaattcaag gggggaaaac tgcggctacc gcaggtgccg cgcgagcggc gtactgacaa   8460
ctagctgtgg taacaccctc acttgctaca tcaaggcccg ggcagcctgt cgagccgcag   8520
ggctccagga ctgcaccatg ctcgtgtgtg gcgacgactt agtcgttatc tgtgaaagtg   8580
cgggggtcca ggaggacgcg gcgagcctga gagccttcac ggaggctatg accaggtact   8640
ccgcccccc cggggacccc ccacaaccag aatacgactt ggagcttata acatcatgct   8700
cctccaacgt gtcagtcgcc cacgacggcg ctggaaagag ggtctactac cttacccgtg   8760
accctacaac ccccctcgcg agagccgcgt gggagacagc aagacacact ccagtcaatt   8820
cctggctagg caacataatc atgtttgccc ccacactgtg ggcgaggatg atactgatga   8880
cccatttctt tagcgtcctc atagccaggg atcagcttga acaggctctt aactgtgaga   8940
tctacggagc ctgctactcc atagaaccac tggatctacc tccaatcatt caaagactcc   9000
atggcctcag cgcattttca ctccacagtt actctccagg tgaaatcaat agggtggccg   9060
catgcctcag aaaacttggg gtcccgccct tgcgagcttg gagacaccgg gcccggagcg   9120
tccgcgctag gcttctgtcc agaggaggca gggctgccat atgtggcaag tacctcttca   9180
actgggcagt aagaacaaag ctcaaactca ctccaatagc ggccgctggc cggctggact   9240
tgtccggttg gttcacggct ggctacagcg gggagacat ttatcacagc gtgtctcatg   9300
cccggccccg ctggttctgg ttttgcctac tcctgctcgc tgcaggggta ggcatctacc   9360
tcctccccaa ccgatgaagg ttggggtaaa cactccggcc tcttaagcca tttcctgttt   9420
ttttttttt ttttttttt tttttctttt ttttttctt tcctttcctt cttttttcc   9480
tttcttttc ccttctttaa tggtggctcc atcttagccc tagtcacggc tagctgtgaa   9540
aggtccgtga gccgcatgac tgcagagagt gctgatactg gcctctctgc agatcatgt    9599
```

<210> SEQ ID NO 2
<211> LENGTH: 2428
<212> TYPE: DNA

-continued

<213> ORGANISM: Hepatitis C virus

<400> SEQUENCE: 2

```
atgagcacga atcctaaacc tcaaagaaaa accaaacgta acaccaaccg tcgcccacag     60
gacgtcaagt tcccgggtgg cggtcagatc gttggtggag tttacttgtt gccgcgcagg    120
ggccctagat tgggtgtgcg cgcgacgagg aagacttccg agcggtcgca acctcgaggt    180
agacgtcagc ctatccccaa ggcacgtcgg cccgagggca ggacctgggc tcagcccggg    240
tacccttggc ccctctatgg caatgagggt tgcgggtggg cgggatggct cctgtctccc    300
cgtggctctc ggcctagctg gggccccaca gacccccggc gtaggtcgcg caatttgggt    360
aaggtcatcg ataccettac gtgcggcttc gccgacctca tggggtacat accgctcgtc    420
ggcgcccctc ttggaggcgc tgccagggcc ctggcgcatg gcgtccgggt tctggaagac    480
ggcgtgaact atgcaacagg gaaccttcct ggttgctctt tctctatctt ccttctggcc    540
ctgctctctt gcctgactgt gcccgcttca gcctaccaag tgcgcaattc ctcggggctt    600
taccatgtca ccaatgattg ccctaactcg agtattgtgt acgaggcggc cgatgccatc    660
ctgcacactc cggggtgtgt cccttgcgtt cgcgagggta acgcctcgag gtgttgggtg    720
gcggtgaccc ccacggtggc caccagggac ggcaaactcc ccacaacgca gcttcgacgt    780
catatcgatc tgcttgtcgg gagcgccacc ctctgctcgg ccctctacgt gggggacctg    840
tgcgggtctg tctttcttgt tggtcaactg tttaccttct ctcccaggcg ccactggacg    900
acgcaagact gcaattgttc tatctatccc ggccatataa cgggtcatcg catggcatgg    960
gatatgatga tgaactggtc ccctacggca gcgttggtgg tagctcagct gctccggatc   1020
ccacaagcca tcatggacat gatcgctggt gctcactggg gagtcctggc gggcatagcg   1080
tatttctcca tggtggggaa ctgggcgaag gtcctggtag tgctgctgct atttgccggc   1140
gtcgacgcgg aaacccacgt caccggggga aatgccggcc gcaccacggc tgggcttgtt   1200
ggtctcctta caccaggcgc caagcagaac atccaactga tcaacaccaa cggcagttgg   1260
cacatcaata gcacggcctt gaattgcaat gaaagcctta acaccggctg gttagcaggg   1320
ctcttctatc aacacaaatt caactcttca ggctgtcctg agaggttggc cagctgccga   1380
cgccttaccg attttgccca gggctggggt cctatcagtt atgccaacgg aagcggcctc   1440
gacgaacgcc cctactgctg gcactaccct ccaagacctt gtggcattgt gcccgcaaag   1500
agcgtgtgtg gcccggtata ttgcttcact cccagccccg tggtggtggg aacgaccgac   1560
aggtcgggcg cgcctaccta cagctggggt gcaaatgata cggatgtctt cgtccttaac   1620
aacaccaggc caccgctggg caattggttc ggttgtacct ggatgaactc aactggattc   1680
accaaagtgt gcggagcgcc cccttgtgtc atcggagggg tggcaacaa caccttgctc    1740
tgccccactg attgcttccg caaacatccg gaagccacat actctcggtg cggctccggt   1800
ccctggatta cacccaggtg catggtcgac tacccgtata ggctttggca ctatccttgt   1860
accatcaatt acaccatatt caaagtcagg atgtacgtgg gaggggtcga gcacaggctg   1920
gaagcggcct gcaactggac gcggggcgaa cgctgtgatc tggaagacag ggacaggtcc   1980
gagctcagcc cgttgctgct gtccaccaca cagtggcagg tccttccgtg ttctttcacg   2040
accctgccag ccttgtccac cggcctcatc cacctccacc agaacattgt ggacgtgcag   2100
tacttgtacg gggtagggtc aagcatcgcg tcctgggcca ttaagtggga gtacgtcgtt   2160
ctcctgttcc ttctgcttgc agacgcgcgc gtctgctcct gcttgtggat gatgttactc   2220
atatcccaag cggaggcggc tttggagaac ctcgtaatac tcaatgcagc atccctggcc   2280
```

-continued gggacgcacg gtcttgtgtc cttcctcgtg ttcttctgct ttgcgtggta tctgaagggt 2340
aggtgggtgc ccggagcggt ctacgccctc tacgggatgt ggcctctcct cctgctcctg 2400
ctggcgttgc ctcagcgggc atacgcac 2428

<210> SEQ ID NO 3
<211> LENGTH: 3011
<212> TYPE: PRT
<213> ORGANISM: Hepatitis C virus

<400> SEQUENCE: 3

Met Ser Thr Asn Pro Lys Pro Gln Arg Lys Thr Lys Arg Asn Thr Asn
1 5 10 15

Arg Arg Pro Gln Asp Val Lys Phe Pro Gly Gly Gly Gln Ile Val Gly
20 25 30

Gly Val Tyr Leu Leu Pro Arg Arg Gly Pro Arg Leu Gly Val Arg Ala
35 40 45

Thr Arg Lys Thr Ser Glu Arg Ser Gln Pro Arg Gly Arg Arg Gln Pro
50 55 60

Ile Pro Lys Ala Arg Arg Pro Glu Gly Arg Thr Trp Ala Gln Pro Gly
65 70 75 80

Tyr Pro Trp Pro Leu Tyr Gly Asn Glu Gly Cys Gly Trp Ala Gly Trp
85 90 95

Leu Leu Ser Pro Arg Gly Ser Arg Pro Ser Trp Gly Pro Thr Asp Pro
100 105 110

Arg Arg Arg Ser Arg Asn Leu Gly Lys Val Ile Asp Thr Leu Thr Cys
115 120 125

Gly Phe Ala Asp Leu Met Gly Tyr Ile Pro Leu Val Gly Ala Pro Leu
130 135 140

Gly Gly Ala Ala Arg Ala Leu Ala His Gly Val Arg Val Leu Glu Asp
145 150 155 160

Gly Val Asn Tyr Ala Thr Gly Asn Leu Pro Gly Cys Ser Phe Ser Ile
165 170 175

Phe Leu Leu Ala Leu Leu Ser Cys Leu Thr Val Pro Ala Ser Ala Tyr
180 185 190

Gln Val Arg Asn Ser Ser Gly Leu Tyr His Val Thr Asn Asp Cys Pro
195 200 205

Asn Ser Ser Ile Val Tyr Glu Ala Ala Asp Ala Ile Leu His Thr Pro
210 215 220

Gly Cys Val Pro Cys Val Arg Glu Gly Asn Ala Ser Arg Cys Trp Val
225 230 235 240

Ala Val Thr Pro Thr Val Ala Thr Arg Asp Gly Lys Leu Pro Thr Thr
245 250 255

Gln Leu Arg Arg His Ile Asp Leu Leu Val Gly Ser Ala Thr Leu Cys
260 265 270

Ser Ala Leu Tyr Val Gly Asp Leu Cys Gly Ser Val Phe Leu Val Gly
275 280 285

Gln Leu Phe Thr Phe Ser Pro Arg Arg His Trp Thr Thr Gln Asp Cys
290 295 300

Asn Cys Ser Ile Tyr Pro Gly His Ile Thr Gly His Arg Met Ala Trp
305 310 315 320

Asp Met Met Met Asn Trp Ser Pro Thr Ala Ala Leu Val Val Ala Gln
325 330 335

Leu Leu Arg Ile Pro Gln Ala Ile Met Asp Met Ile Ala Gly Ala His

-continued

```
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765
```

-continued

```
Leu Val Phe Phe Cys Phe Ala Trp Tyr Leu Lys Gly Arg Trp Val Pro
    770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Gln
        995                 1000                1005

Glu Ile  Leu Leu Gly Pro Ala  Asp Gly Met Val Ser  Lys Gly Trp
    1010                 1015                 1020

Arg Leu  Leu Ala Pro Ile Thr  Ala Tyr Ala Gln Gln  Thr Arg Gly
    1025                 1030                 1035

Leu Leu  Gly Cys Ile Ile Thr  Ser Leu Thr Gly Arg  Asp Lys Asn
    1040                 1045                 1050

Gln Val  Glu Gly Glu Val Gln  Ile Val Ser Thr Ala  Thr Gln Thr
    1055                 1060                 1065

Phe Leu  Ala Thr Cys Ile Asn  Gly Val Cys Trp Thr  Val Tyr His
    1070                 1075                 1080

Gly Ala  Gly Thr Arg Thr Ile  Ala Ser Pro Lys Gly  Pro Val Ile
    1085                 1090                 1095

Gln Met  Tyr Thr Asn Val Asp  Gln Asp Leu Val Gly  Trp Pro Ala
    1100                 1105                 1110

Pro Gln  Gly Ser Arg Ser Leu  Thr Pro Cys Thr Cys  Gly Ser Ser
    1115                 1120                 1125

Asp Leu  Tyr Leu Val Thr Arg  His Ala Asp Val Ile  Pro Val Arg
    1130                 1135                 1140

Arg Arg  Gly Asp Ser Arg Gly  Ser Leu Leu Ser Pro  Arg Pro Ile
    1145                 1150                 1155

Ser Tyr  Leu Lys Gly Ser Ser  Gly Gly Pro Leu Leu  Cys Pro Ala
    1160                 1165                 1170
```

-continued

```
Gly His  Ala Val Gly Leu Phe  Arg Ala Ala Val Cys  Thr Arg Gly
    1175                 1180                 1185

Val Ala  Lys Ala Val Asp Phe  Ile Pro Val Glu Asn  Leu Gly Thr
    1190                 1195                 1200

Thr Met  Arg Ser Pro Val Phe  Thr Asp Asn Ser Ser  Pro Pro Ala
    1205                 1210                 1215

Val Pro  Gln Ser Phe Gln Val  Ala His Leu His Ala  Pro Thr Gly
    1220                 1225                 1230

Ser Gly  Lys Ser Thr Lys Val  Pro Ala Ala Tyr Ala  Ala Gln Gly
    1235                 1240                 1245

Tyr Lys  Val Leu Val Leu Asn  Pro Ser Val Ala Ala  Thr Leu Gly
    1250                 1255                 1260

Phe Gly  Ala Tyr Met Ser Lys  Ala His Gly Val Asp  Pro Asn Ile
    1265                 1270                 1275

Arg Thr  Gly Val Arg Thr Ile  Thr Thr Gly Ser Pro  Ile Thr Tyr
    1280                 1285                 1290

Ser Thr  Tyr Gly Lys Phe Leu  Ala Asp Gly Gly Cys  Ser Gly Gly
    1295                 1300                 1305

Ala Tyr  Asp Ile Ile Ile Cys  Asp Glu Cys His Ser  Thr Asp Ala
    1310                 1315                 1320

Thr Ser  Ile Leu Gly Ile Gly  Thr Val Leu Asp Gln  Ala Glu Thr
    1325                 1330                 1335

Ala Gly  Ala Arg Leu Val Val  Leu Ala Thr Ala Thr  Pro Pro Gly
    1340                 1345                 1350

Ser Val  Thr Val Ser His Pro  Asn Ile Glu Glu Val  Ala Leu Ser
    1355                 1360                 1365

Thr Thr  Gly Glu Ile Pro Phe  Tyr Gly Lys Ala Ile  Pro Leu Glu
    1370                 1375                 1380

Val Ile  Lys Gly Gly Arg His  Leu Ile Phe Cys His  Ser Lys Lys
    1385                 1390                 1395

Lys Cys  Asp Glu Leu Ala Ala  Lys Leu Val Ala Leu  Gly Ile Asn
    1400                 1405                 1410

Ala Val  Ala Tyr Tyr Arg Gly  Leu Asp Val Ser Val  Ile Pro Thr
    1415                 1420                 1425

Ser Gly  Asp Val Val Val Val  Ser Thr Asp Ala Leu  Met Thr Gly
    1430                 1435                 1440

Phe Thr  Gly Asp Phe Asp Ser  Val Ile Asp Cys Asn  Thr Cys Val
    1445                 1450                 1455

Thr Gln  Thr Val Asp Phe Ser  Leu Asp Pro Thr Phe  Thr Ile Glu
    1460                 1465                 1470

Thr Thr  Thr Leu Pro Gln Asp  Ala Val Ser Arg Thr  Gln Arg Arg
    1475                 1480                 1485

Gly Arg  Thr Gly Arg Gly Lys  Pro Gly Ile Tyr Arg  Phe Val Ala
    1490                 1495                 1500

Pro Gly  Glu Arg Pro Ser Gly  Met Phe Asp Ser Ser  Val Leu Cys
    1505                 1510                 1515

Glu Cys  Tyr Asp Ala Gly Cys  Ala Trp Tyr Glu Leu  Thr Pro Ala
    1520                 1525                 1530

Glu Thr  Thr Val Arg Leu Arg  Ala Tyr Met Asn Thr  Pro Gly Leu
    1535                 1540                 1545

Pro Val  Cys Gln Asp His Leu  Glu Phe Trp Glu Gly  Val Phe Thr
    1550                 1555                 1560

Gly Leu  Thr His Ile Asp Ala  His Phe Leu Ser Gln  Thr Lys Gln
```

-continued

```
    1565                1570                1575

Ser Gly  Glu Asn Phe Pro Tyr  Leu Val Ala Tyr Gln  Ala Thr Val
    1580                1585                1590

Cys Ala  Arg Ala Gln Ala Pro  Pro Pro Ser Trp Asp  Gln Met Trp
    1595                1600                1605

Lys Cys  Leu Ile Arg Leu Lys  Pro Thr Leu His Gly  Pro Thr Pro
    1610                1615                1620

Leu Leu  Tyr Arg Leu Gly Ala  Val Gln Asn Glu Val  Thr Leu Thr
    1625                1630                1635

His Pro  Ile Thr Lys Tyr Ile  Met Thr Cys Met Ser  Ala Asp Leu
    1640                1645                1650

Glu Val  Val Thr Ser Thr Trp  Val Leu Val Gly Gly  Val Leu Ala
    1655                1660                1665

Ala Leu  Ala Ala Tyr Cys Leu  Ser Thr Gly Cys Val  Val Ile Val
    1670                1675                1680

Gly Arg  Ile Val Leu Ser Gly  Lys Pro Ala Ile Ile  Pro Asp Arg
    1685                1690                1695

Glu Val  Leu Tyr Gln Glu Phe  Asp Glu Met Glu Glu  Cys Ser Gln
    1700                1705                1710

His Leu  Pro Tyr Ile Glu Gln  Gly Met Met Leu Ala  Glu Gln Phe
    1715                1720                1725

Lys Gln  Lys Ala Leu Gly Leu  Leu Gln Thr Ala Ser  Arg His Ala
    1730                1735                1740

Glu Val  Ile Thr Pro Ala Val  Gln Thr Asn Trp Gln  Lys Leu Glu
    1745                1750                1755

Val Phe  Trp Ala Lys His Met  Trp Asn Phe Ile Ser  Gly Ile Gln
    1760                1765                1770

Tyr Leu  Ala Gly Leu Ser Thr  Leu Pro Gly Asn Pro  Ala Ile Ala
    1775                1780                1785

Ser Leu  Met Ala Phe Thr Ala  Ala Val Thr Ser Pro  Leu Thr Thr
    1790                1795                1800

Gly Gln  Thr Leu Leu Phe Asn  Ile Leu Gly Gly Trp  Val Ala Ala
    1805                1810                1815

Gln Leu  Ala Ala Pro Gly Ala  Ala Thr Ala Phe Val  Gly Ala Gly
    1820                1825                1830

Leu Ala  Gly Ala Ala Ile Gly  Ser Val Gly Leu Gly  Lys Val Leu
    1835                1840                1845

Val Asp  Ile Leu Ala Gly Tyr  Gly Ala Gly Val Ala  Gly Ala Leu
    1850                1855                1860

Val Ala  Phe Lys Ile Met Ser  Gly Glu Val Pro Ser  Thr Glu Asp
    1865                1870                1875

Leu Val  Asn Leu Leu Pro Ala  Ile Leu Ser Pro Gly  Ala Leu Val
    1880                1885                1890

Val Gly  Val Val Cys Ala Ala  Ile Leu Arg Arg His  Val Gly Pro
    1895                1900                1905

Gly Glu  Gly Ala Val Gln Trp  Met Asn Arg Leu Ile  Ala Phe Ala
    1910                1915                1920

Ser Arg  Gly Asn His Val Ser  Pro Thr His Tyr Val  Pro Glu Ser
    1925                1930                1935

Asp Ala  Ala Ala Arg Val Thr  Ala Ile Leu Ser Ser  Leu Thr Val
    1940                1945                1950

Thr Gln  Leu Leu Arg Arg Leu  His Gln Trp Ile Ser  Ser Glu Cys
    1955                1960                1965
```

-continued

```
Thr Thr  Pro Cys Ser Gly Ser  Trp Leu Arg Asp Ile  Trp Asp Trp
    1970                 1975                 1980

Ile Cys  Glu Val Leu Ser Asp  Phe Lys Thr Trp Leu  Lys Ala Lys
    1985                 1990                 1995

Leu Met  Pro Gln Leu Pro Gly  Ile Pro Phe Val Ser  Cys Gln Arg
    2000                 2005                 2010

Gly Tyr  Arg Gly Val Trp Arg  Gly Asp Gly Ile Met  His Thr Arg
    2015                 2020                 2025

Cys His  Cys Gly Ala Glu Ile  Thr Gly His Val Lys  Asn Gly Thr
    2030                 2035                 2040

Met Arg  Ile Val Gly Pro Arg  Thr Cys Arg Asn Met  Trp Ser Gly
    2045                 2050                 2055

Thr Phe  Pro Ile Asn Ala Tyr  Thr Thr Gly Pro Cys  Thr Pro Leu
    2060                 2065                 2070

Pro Ala  Pro Asn Tyr Lys Phe  Ala Leu Trp Arg Val  Ser Ala Glu
    2075                 2080                 2085

Glu Tyr  Val Glu Ile Arg Arg  Val Gly Asp Phe His  Tyr Val Ser
    2090                 2095                 2100

Gly Met  Thr Thr Asp Asn Leu  Lys Cys Pro Cys Gln  Ile Pro Ser
    2105                 2110                 2115

Pro Glu  Phe Phe Thr Glu Leu  Asp Gly Val Arg Leu  His Arg Phe
    2120                 2125                 2130

Ala Pro  Pro Cys Lys Pro Leu  Leu Arg Glu Glu Val  Ser Phe Arg
    2135                 2140                 2145

Val Gly  Leu His Glu Tyr Pro  Val Gly Ser Gln Leu  Pro Cys Glu
    2150                 2155                 2160

Pro Glu  Pro Asp Val Ala Val  Leu Thr Ser Met Leu  Thr Asp Pro
    2165                 2170                 2175

Ser His  Ile Thr Ala Glu Ala  Ala Gly Arg Arg Leu  Ala Arg Gly
    2180                 2185                 2190

Ser Pro  Pro Ser Met Ala Ser  Ser Ser Ala Ser Gln  Leu Ser Ala
    2195                 2200                 2205

Pro Ser  Leu Lys Ala Thr Cys  Thr Ala Asn His Asp  Ser Pro Asp
    2210                 2215                 2220

Ala Glu  Leu Ile Glu Ala Asn  Leu Leu Trp Arg Gln  Glu Met Gly
    2225                 2230                 2235

Gly Asn  Ile Thr Arg Val Glu  Ser Glu Asn Lys Val  Val Ile Leu
    2240                 2245                 2250

Asp Ser  Phe Asp Pro Leu Val  Ala Glu Glu Asp Glu  Arg Glu Val
    2255                 2260                 2265

Ser Val  Pro Ala Glu Ile Leu  Arg Lys Ser Arg Arg  Phe Ala Arg
    2270                 2275                 2280

Ala Leu  Pro Val Trp Ala Arg  Pro Asp Tyr Asn Pro  Pro Leu Val
    2285                 2290                 2295

Glu Thr  Trp Lys Lys Pro Asp  Tyr Glu Pro Pro Val  Val His Gly
    2300                 2305                 2310

Cys Pro  Leu Pro Pro Pro Arg  Ser Pro Pro Val Pro  Pro Pro Arg
    2315                 2320                 2325

Lys Lys  Arg Thr Val Val Leu  Thr Glu Ser Thr Leu  Ser Thr Ala
    2330                 2335                 2340

Leu Ala  Glu Leu Ala Thr Lys  Ser Phe Gly Ser Ser  Ser Thr Ser
    2345                 2350                 2355
```

-continued

```
Gly Ile  Thr Gly Asp Asn Thr  Thr Thr Ser Ser Glu  Pro Ala Pro
    2360                 2365                 2370

Ser Gly  Cys Pro Pro Asp Ser  Asp Val Glu Ser Tyr  Ser Ser Met
    2375                 2380                 2385

Pro Pro  Leu Glu Gly Glu Pro  Gly Asp Pro Asp Leu  Ser Asp Gly
    2390                 2395                 2400

Ser Trp  Ser Thr Val Ser Ser  Gly Ala Asp Thr Glu  Asp Val Val
    2405                 2410                 2415

Cys Cys  Ser Met Ser Tyr Ser  Trp Thr Gly Ala Leu  Val Thr Pro
    2420                 2425                 2430

Cys Ala  Ala Glu Glu Gln Lys  Leu Pro Ile Asn Ala  Leu Ser Asn
    2435                 2440                 2445

Ser Leu  Leu Arg His His Asn  Leu Val Tyr Ser Thr  Thr Ser Arg
    2450                 2455                 2460

Ser Ala  Cys Gln Arg Gln Lys  Lys Val Thr Phe Asp  Arg Leu Gln
    2465                 2470                 2475

Val Leu  Asp Ser His Tyr Gln  Asp Val Leu Lys Glu  Val Lys Ala
    2480                 2485                 2490

Ala Ala  Ser Lys Val Lys Ala  Asn Leu Leu Ser Val  Glu Glu Ala
    2495                 2500                 2505

Cys Ser  Leu Thr Pro Pro His  Ser Ala Lys Ser Lys  Phe Gly Tyr
    2510                 2515                 2520

Gly Ala  Lys Asp Val Arg Cys  His Ala Arg Lys Ala  Val Ala His
    2525                 2530                 2535

Ile Asn  Ser Val Trp Lys Asp  Leu Leu Glu Asp Ser  Val Thr Pro
    2540                 2545                 2550

Ile Asp  Thr Thr Ile Met Ala  Lys Asn Glu Val Phe  Cys Val Gln
    2555                 2560                 2565

Pro Glu  Lys Gly Gly Arg Lys  Pro Ala Arg Leu Ile  Val Phe Pro
    2570                 2575                 2580

Asp Leu  Gly Val Arg Val Cys  Glu Lys Met Ala Leu  Tyr Asp Val
    2585                 2590                 2595

Val Ser  Lys Leu Pro Leu Ala  Val Met Gly Ser Ser  Tyr Gly Phe
    2600                 2605                 2610

Gln Tyr  Ser Pro Gly Gln Arg  Val Glu Phe Leu Val  Gln Ala Trp
    2615                 2620                 2625

Lys Ser  Lys Lys Thr Pro Met  Gly Phe Ser Tyr Asp  Thr Arg Cys
    2630                 2635                 2640

Phe Asp  Ser Thr Val Thr Glu  Ser Asp Ile Arg Thr  Glu Glu Ala
    2645                 2650                 2655

Ile Tyr  Gln Cys Cys Asp Leu  Asp Pro Gln Ala Arg  Val Ala Ile
    2660                 2665                 2670

Lys Ser  Leu Thr Glu Arg Leu  Tyr Val Gly Gly Pro  Leu Thr Asn
    2675                 2680                 2685

Ser Arg  Gly Glu Asn Cys Gly  Tyr Arg Arg Cys Arg  Ala Ser Gly
    2690                 2695                 2700

Val Leu  Thr Thr Ser Cys Gly  Asn Thr Leu Thr Cys  Tyr Ile Lys
    2705                 2710                 2715

Ala Arg  Ala Ala Cys Arg Ala  Ala Gly Leu Gln Asp  Cys Thr Met
    2720                 2725                 2730

Leu Val  Cys Gly Asp Asp Leu  Val Val Ile Cys Glu  Ser Ala Gly
    2735                 2740                 2745

Val Gln  Glu Asp Ala Ala Ser  Leu Arg Ala Phe Thr  Glu Ala Met
```

-continued

```
    2750                2755                2760

Thr Arg  Tyr Ser Ala Pro Pro  Gly Asp Pro Pro Gln  Pro Glu Tyr
    2765                2770                2775

Asp Leu  Glu Leu Ile Thr Ser  Cys Ser Ser Asn Val  Ser Val Ala
    2780                2785                2790

His Asp  Gly Ala Gly Lys Arg  Val Tyr Tyr Leu Thr  Arg Asp Pro
    2795                2800                2805

Thr Thr  Pro Leu Ala Arg Ala  Ala Trp Glu Thr Ala  Arg His Thr
    2810                2815                2820

Pro Val  Asn Ser Trp Leu Gly  Asn Ile Ile Met Phe  Ala Pro Thr
    2825                2830                2835

Leu Trp  Ala Arg Met Ile Leu  Met Thr His Phe Phe  Ser Val Leu
    2840                2845                2850

Ile Ala  Arg Asp Gln Leu Glu  Gln Ala Leu Asn Cys  Glu Ile Tyr
    2855                2860                2865

Gly Ala  Cys Tyr Ser Ile Glu  Pro Leu Asp Leu Pro  Pro Ile Ile
    2870                2875                2880

Gln Arg  Leu His Gly Leu Ser  Ala Phe Ser Leu His  Ser Tyr Ser
    2885                2890                2895

Pro Gly  Glu Ile Asn Arg Val  Ala Ala Cys Leu Arg  Lys Leu Gly
    2900                2905                2910

Val Pro  Pro Leu Arg Ala Trp  Arg His Arg Ala Arg  Ser Val Arg
    2915                2920                2925

Ala Arg  Leu Leu Ser Arg Gly  Gly Arg Ala Ala Ile  Cys Gly Lys
    2930                2935                2940

Tyr Leu  Phe Asn Trp Ala Val  Arg Thr Lys Leu Lys  Leu Thr Pro
    2945                2950                2955

Ile Ala  Ala Ala Gly Arg Leu  Asp Leu Ser Gly Trp  Phe Thr Ala
    2960                2965                2970

Gly Tyr  Ser Gly Gly Asp Ile  Tyr His Ser Val Ser  His Ala Arg
    2975                2980                2985

Pro Arg  Trp Phe Trp Phe Cys  Leu Leu Leu Leu Ala  Ala Gly Val
    2990                2995                3000

Gly Ile  Tyr Leu Leu Pro Asn  Arg
    3005                3010


<210> SEQ ID NO 4
<211> LENGTH: 2442
<212> TYPE: DNA
<213> ORGANISM: Hepatitis C virus

<400> SEQUENCE: 4

aagcttatga gcacgaatcc taaacctcaa agaaaaacca aacgtaacac caaccgtcgc      60

ccacaggacg tcaagttccc gggtggcggt cagatcgttg gtggagttta cttgttgccg     120

cgcaggggcc ctagattggg tgtgcgcgcg acgaggaaga cttccgagcg gtcgcaacct     180

cgaggtagac gtcagcctat ccccaaggca cgtcggcccg agggcaggac ctgggctcag     240

cccgggtacc cttggcccct ctatggcaat gagggttgcg ggtgggcggg atggctcctg     300

tctccccgtg gctctcggcc tagctggggc cccacagacc cccggcgtag gtcgcgcaat     360

ttgggtaagg tcatcgatac ccttacgtgc ggcttcgccg acctcatggg gtacataccg     420

ctcgtcggcg cccctcttgg aggcgctgcc agggccctgg cgcatggcgt ccgggttctg     480

gaagacggcg tgaactatgc aacagggaac cttcctggtt gctctttctc tatcttcctt     540
```

-continued

```
ctggccctgc tctcttgcct gaccgtgccc gcttcagcct accaagtgcg caattcctcg    600

gggctttacc atgtcaccaa tgattgccct aactcgagta ttgtgtacga ggcggccgat    660

gccatcctgc acactccggg gtgtgtccct tgcgttcgcg agggtaacgc ctcgaggtgt    720

tgggtggcgg tgacccccac ggtggccacc agggacggca aactccccac aacgcagctt    780

cgacgtcata tcgatctgct tgtcgggagc gccaccctct gctcggccct ctacgtgggg    840

gacctgtgcg ggtctgtctt tcttgttggt caactgttta ccttctctcc caggcgccac    900

tggacgacgc aagactgcaa ttgttctatc tatcccggcc atataacggg tcatcgcatg    960

gcatgggata tgatgatgaa ctggtcccct acggcagcgt tggtggtagc tcagctgctc   1020

cggatcccac aagccatcat ggacatgatc gctggtgctc actggggagt cctggcgggc   1080

atagcgtatt tctccatggt ggggaactgg gcgaaggtcc tggtagtgct gctgctattt   1140

gccggcgtcg acgcggaaac ccacgtcacc gggggaagtg ccggccgcac cacggctggg   1200

cttgttggtc tccttacacc aggcgccaag cagaacatcc aactgatcaa caccaacggc   1260

agttggcaca tcaatagcac ggccttgaac tgcaatgaaa gccttaacac cggctggtta   1320

gcagggctct tctatcagca caaattcaac tcttcaggct gtcctgagag gttggccagc   1380

tgccgacgcc ttaccgattt tgcccagggc tggggtccta tcagttatgc caacggaagc   1440

ggcctcgacg aacgccccta ctgctggcac taccctccaa gaccttgtgg cattgtgccc   1500

gcaaagagcg tgtgtggccc ggtatattgc ttcactccca gccccgtggt ggtgggaacg   1560

accgacaggt cgggcgcgcc tacctacagc tggggtgcaa atgatacgga tgtcttcgtc   1620

cttaacaaca ccaggccacc gctgggcaat tggttcggtt gtacctggat gaactcaact   1680

ggattcacca aagtgtgcgg agcgccccct tgtgtcatcg gaggggtggg caacaacacc   1740

ttgctctgcc ccactgattg tttccgcaag catccggaag ccacatactc tcggtgcggc   1800

tccggtccct ggattacacc caggtgcatg gtcgactacc cgtataggct ttggcactat   1860

ccttgtacca tcaattacac catattcaaa gtcaggatgt acgtgggagg ggtcgagcac   1920

aggctggaag cggcctgcaa ctggacgcgg ggcgaacgct gtgatctgga agacagggac   1980

aggtccgagc tcagcccatt gctgctgtcc accacacagt ggcaggtcct tccgtgttct   2040

ttcacgaccc tgccagcctt gtccaccggc ctcatccacc tccaccagaa cattgtggac   2100

gtgcagtact tgtacggggt agggtcaagc atcgcgtcct gggccattaa gtgggagtac   2160

gtcgttctcc tgttcctcct gcttgcagac gcgcgcgtct gctcctgctt gtggatgatg   2220

ttactcatat cccaagcgga ggcggctttg gagaacctcg taatactcaa tgcagcatcc   2280

ctggccggga cgcacggtct tgtgtccttc ctcgtgttct tctgctttgc gtggtatctg   2340

aagggtaggt gggtgcccgg agcggtctac gccttctacg ggatgtggcc tctcctcctg   2400

ctcctgctgg cgttgcctca gcgggcatac gcataatcta ga                       2442
```

<210> SEQ ID NO 5
<211> LENGTH: 2253
<212> TYPE: DNA
<213> ORGANISM: Hepatitis C virus

<400> SEQUENCE: 5

```
aagcttatga gcacgaatcc taaacctcaa agaaaaacca aacgtaacac caaccgtcgc     60

ccacaggacg tcaagttccc gggtggcggt cagatcgttg gtggagttta cttgttgccg    120

cgcaggggcc ctagattggg tgtgcgcgcg acgaggaaga cttccgagcg gtcgcaacct    180

cgaggtagac gtcagcctat ccccaaggca cgtcggcccg agggcaggac ctgggctcag    240
```

-continued

```
cccgggtacc cttggcccct ctatggcaat gagggttgcg ggtgggcggg atggctcctg    300
tctccccgtg gctctcggcc tagctggggc cccacagacc cccggcgtag gtcgcgcaat    360
ttgggtaagg tcatcgatac ccttacgtgc ggcttcgccg acctcatggg gtacataccg    420
ctcgtcggcg cccctcttgg aggcgctgcc agggccctgg cgcatggcgt ccgggttctg    480
gaagacggcg tgaactatgc aacagggaac cttcctggtt gctctttctc tatcttcctt    540
ctggccctgc tctcttgcct gaccgtgccc gcttcagcct accaagtgcg caattcctcg    600
gggctttacc atgtcaccaa tgattgccct aactcgagta ttgtgtacga ggcggccgat    660
gccatcctgc acactccggg gtgtgtccct tgcgttcgcg agggtaacgc ctcgaggtgt    720
tgggtggcgg tgacccccac ggtggccacc agggacggca aactccccac aacgcagctt    780
cgacgtcata tcgatctgct tgtcgggagc gccaccctct gctcggccct ctacgtgggg    840
gacctgtgcg ggtctgtctt tcttgttggt caactgttta ccttctctcc caggcgccac    900
tggacgacgc aagactgcaa ttgttctatc tatcccggcc atataacggg tcatcgcatg    960
gcatgggata tgatgatgaa ctggtcccct acggcagcgt tggtggtagc tcagctgctc   1020
cggatcccac aagccatcat ggacatgatc gctggtgctc actggggagt cctggcgggc   1080
atagcgtatt tctccatggt ggggaactgg gcgaaggtcc tggtagtgct gctgctattt   1140
gccggcgtcg acgcggaaac ccacgtcacc gggggaagtg ccggccgcac cacggctggg   1200
cttgttggtc tccttacacc aggcgccaag cagaacatcc aactgatcaa caccaacggc   1260
agttggcaca tcaatagcac ggccttgaac tgcaatgaaa gccttaacac cggctggtta   1320
gcagggctct tctatcagca caaattcaac tcttcaggct gtcctgagag gttggccagc   1380
tgccgacgcc ttaccgattt tgcccagggc tggggtccta tcagttatgc caacggaagc   1440
ggcctcgacg aacgccccta ctgctggcac taccctccaa gaccttgtgg cattgtgccc   1500
gcaaagagcg tgtgtggccc ggtatattgc ttcactccca gccccgtggt ggtgggaacg   1560
accgacaggt cgggcgcgcc tacctacagc tggggtgcaa atgatacgga tgtcttcgtc   1620
cttaacaaca ccaggccacc gctgggcaat tggttcggtt gtacctggat gaactcaact   1680
ggattcacca aagtgtgcgg agcgccccct tgtgtcatcg gaggggtggg caacaacacc   1740
ttgctctgcc ccactgattg tttccgcaag catccggaag ccacatactc tcggtgcggc   1800
tccggtccct ggattacacc caggtgcatg gtcgactacc cgtataggct ttggcactat   1860
ccttgtacca tcaattacac catattcaaa gtcaggatgt acgtgggagg ggtcgagcac   1920
aggctggaag cggcctgcaa ctggacgcgg ggcgaacgct gtgatctgga agacagggac   1980
aggtccgagc tcagcccatt gctgctgtcc accacacagt ggcaggtcct tccgtgttct   2040
ttcacgaccc tgccagcctt gtccaccggc ctcatccacc tccaccagaa cattgtggac   2100
gtgcagtact tgtacggggt agggtcaagc atcgcgtcct gggccattaa gtgggagtac   2160
gtcgttctcc tgttcctcct gcttgcagac gcgcgcgtct gctcctgctt gtggatgatg   2220
ttactcatat cccaagcgga ggcgtaatct aga                                2253
```

<210> SEQ ID NO 6
<211> LENGTH: 1863
<212> TYPE: DNA
<213> ORGANISM: Hepatitis C virus

<400> SEQUENCE: 6

```
aagcttatgg acctcatggg gtacataccg ctcgtcggcg cccctcttgg aggcgctgcc     60
```

-continued

```
agggccctgg cgcatggcgt ccgggttctg gaagacggcg tgaactatgc aacagggaac    120

cttcctggtt gctctttctc tatcttcctt ctggccctgc tctcttgcct gaccgtgccc    180

gcttcagcct accaagtgcg caattcctcg ggctttacc atgtcaccaa tgattgccct    240

aactcgagta ttgtgtacga ggcggccgat gccatcctgc acactccggg gtgtgtccct    300

tgcgttcgcg agggtaacgc ctcgaggtgt tgggtggcgg tgaccccac ggtggccacc    360

agggacggca aactccccac aacgcagctt cgacgtcata tcgatctgct tgtcgggagc    420

gccaccctct gctcggccct ctacgtgggg gacctgtgcg ggtctgtctt tcttgttggt    480

caactgttta ccttctctcc ccgtcgccac tggacgacgc aagactgcaa ttgttctatc    540

tatcccggcc atataacggg tcatcgcatg gcatgggata tgatgatgaa ctggtcccct    600

acggcagcgt tggtggtagc tcagctgctc cggatcccac aagccatcat ggacatgatc    660

gctggtgctc actggggagt cctggcgggc atagcgtatt tctccatggt ggggaactgg    720

gcgaaggtcc tggtagtgct gctgctattt gccggcgtcg acgcggaaac ccacgtcacc    780

gggggaagtg ccggccgcac cacggctggg cttgttggtc tccttacacc aggcgccaag    840

cagaacatcc aactgatcaa caccaacggc agttggcaca tcaatagcac ggccttgaac    900

tgcaatgaaa gccttaacac cggctggtta gcagggctct tctatcagca caaattcaac    960

tcttcaggct gtcctgagag gttggccagc tgccgacgcc ttaccgattt tgcccagggc   1020

tggggtccta tcagttatgc caacggaagc ggcctcgacg aacgccccta ctgctggcac   1080

taccctccaa gaccttgtgg cattgtgccc gcaaagagcg tgtgtggccc ggtatattgc   1140

ttcactccca gccccgtggt ggtgggaacg accgacaggt cgggcgcgcc tacctacagc   1200

tggggtgcaa atgatacgga tgtcttcgtc cttaacaaca ccaggccacc gctgggcaat   1260

tggttcggtt gtacctggat gaactcaact ggattcacca aagtgtgcgg agcgcccct    1320

tgtgtcatcg gaggggtggg caacaacacc ttgctctgcc ccactgattg tttccgcaag   1380

catccggaag ccacatactc tcggtgcggc tccggtccct ggattacacc caggtgcatg   1440

gtcgactacc cgtataggct ttggcactat ccttgtacca tcaattacac catattcaaa   1500

gtcaggatgt acgtgggagg ggtcgagcac aggctggaag cggcctgcaa ctggacgcgg   1560

ggcgaacgct gtgatctgga agacagggac aggtccgagc tcagcccatt gctgctgtcc   1620

accacacagt ggcaggtcct tccgtgttct ttcacgaccc tgccagcctt gtccaccggc   1680

ctcatccacc tccaccagaa cattgtggac gtgcagtact tgtacggggt agggtcaagc   1740

atcgcgtcct gggccattaa gtgggagtac gtcgttctcc tgttcctcct gcttgctgac   1800

gcgcgcgtct gctcctgctt gtggatgatg ttactcatat cccaagcgga ggcgtaatct   1860

aga                                                                 1863
```

<210> SEQ ID NO 7
<211> LENGTH: 1935
<212> TYPE: DNA
<213> ORGANISM: Hepatitis C virus

<400> SEQUENCE: 7

```
aagcttatgg gttgctcttt ctctatcttc cttctggccc tgctctcttg cctgaccgtg     60

cccgcttcag cctaccaagt gcgcaattcc tcggggcttt accatgtcac caatgattgc    120

cctaactcga gtattgtgta cgaggcggcc gatgccatcc tgcacactcc ggggtgtgtc    180

ccttgcgttc gcgagggtaa cgcctcgagg tgttgggtgg cggtgacccc cacggtggcc    240

accagggacg gcaaactccc cacaacgcag cttcgacgtc atatcgatct gcttgtcggg    300
```

-continued

```
agcgccaccc tctgctcggc cctctacgtg ggggacctgt gcgggtctgt ctttcttgtt    360

ggtcaactgt ttaccttctc tcccaggcgc cactggacga cgcaagactg caattgttct    420

atctatcccg gccatataac gggtcatcgc atggcatggg atatgatgat gaactggtcc    480

cctacggcag cgttggtggt agctcagctg ctccggatcc cacaagccat catggacatg    540

atcgctggtg ctcactgggg agtcctggcg ggcatagcgt atttctccat ggtggggaac    600

tgggcgaagg tcctggtagt gctgctgcta tttgccggcg tcgacgcgga aacccacgtc    660

accgggggaa gtgccggccg caccacggct gggcttgttg gtctccttac accaggcgcc    720

aagcagaaca tccaactgat caacaccaac ggcagttggc acatcaatag cacggccttg    780

aactgcaatg aaagccttaa caccggctgg ttagcagggc tcttctatca gcacaaattc    840

aactcttcag gctgtcctga gaggttggcc agctgccgac gccttaccga ttttgcccag    900

ggctggggtc ctatcagtta tgccaacgga agcggcctcg acgaacgccc ctactgctgg    960

cactaccctc caagaccttg tggcattgtg cccgcaaaga gcgtgtgtgg cccggtatat   1020

tgcttcactc ccagccccgt ggtggtggga acgaccgaca ggtcgggcgc gcctacctac   1080

agctggggtg caaatgatac ggatgtcttc gtccttaaca acaccaggcc accgctgggc   1140

aattggttcg gttgtacctg gatgaactca actggattca ccaaagtgtg cggagcgccc   1200

ccttgtgtca tcggaggggt gggcaacaac accttgctct gccccactga ttgtttccgc   1260

aagcatccgg aagccacata ctctcggtgc ggctccggtc cctggattac acccaggtgc   1320

atggtcgact acccgtatag gctttggcac tatccttgta ccatcaatta caccatattc   1380

aaagtcagga tgtacgtggg aggggtcgag cacaggctgg aagcggcctg caactggacg   1440

cggggcgaac gctgtgatct ggaagacagg gacaggtccg agctcagccc attgctgctg   1500

tccaccacac agtggcaggt ccttccgtgt tctttcacga ccctgccagc cttgtccacc   1560

ggcctcatcc acctccacca gaacattgtg gacgtgcagt acttgtacgg ggtagggtca   1620

agcatcgcgt cctgggccat taagtgggag tacgtcgttc tcctgttcct cctgcttgca   1680

gacgcgcgcg tctgctcctg cttgtggatg atgttactca tatcccaagc ggaggcggct   1740

ttggagaacc tcgtaatact caatgcagca tccctggccg ggacgcacgg tcttgtgtcc   1800

ttcctcgtgt tcttctgctt tgcgtggtat ctgaagggta ggtgggtgcc cggagcggtc   1860

tacgccttct acgggatgtg gcctctcctc ctgctcctgc tggcgttgcc tcagcgggca   1920

tacgcataat ctaga                                                    1935
```

<210> SEQ ID NO 8
<211> LENGTH: 1746
<212> TYPE: DNA
<213> ORGANISM: Hepatitis C virus

<400> SEQUENCE: 8

```
aagcttatgg gttgctcttt ctctatcttc cttctggccc tgctctcttg cctgaccgtg     60

cccgcttcag cctaccaagt gcgcaattcc tcggggcttt accatgtcac caatgattgc    120

cctaactcga gtattgtgta cgaggcggcc gatgccatcc tgcacactcc ggggtgtgtc    180

ccttgcgttc gcgagggtaa cgcctcgagg tgttgggtgg cggtgacccc cacggtggcc    240

accagggacg gcaaactccc cacaacgcag cttcgacgtc atatcgatct gcttgtcggg    300

agcgccaccc tctgctcggc cctctacgtg ggggacctgt gcgggtctgt ctttcttgtt    360

ggtcaactgt ttaccttctc tcccaggcgc cactggacga cgcaagactg caattgttct    420
```

-continued

```
atctatcccg gccatataac gggtcatcgc atggcatggg atatgatgat gaactggtcc    480

cctacggcag cgttggtggt agctcagctg ctccggatcc cacaagccat catggacatg    540

atcgctggtg ctcactgggg agtcctggcg ggcatagcgt atttctccat ggtggggaac    600

tgggcgaagg tcctggtagt gctgctgcta tttgccggcg tcgacgcgga aacccacgtc    660

accgggggaa gtgccggccg caccacggct gggcttgttg gtctccttac accaggcgcc    720

aagcagaaca tccaactgat caacaccaac ggcagttggc acatcaatag cacggccttg    780

aactgcaatg aaagccttaa caccggctgg ttagcagggc tcttctatca gcacaaattc    840

aactcttcag gctgtcctga gaggttggcc agctgccgac gccttaccga ttttgcccag    900

ggctggggtc ctatcagtta tgccaacgga agcggcctcg acgaacgccc ctactgctgg    960

cactaccctc caagaccttg tggcattgtg cccgcaaaga gcgtgtgtgg cccggtatat   1020

tgcttcactc ccagccccgt ggtggtggga acgaccgaca ggtcgggcgc gcctacctac   1080

agctggggtg caaatgatac ggatgtcttc gtccttaaca acaccaggcc accgctgggc   1140

aattggttcg gttgtacctg gatgaactca actggattca ccaaagtgtg cggagcgccc   1200

ccttgtgtca tcggaggggt gggcaacaac accttgctct gccccactga ttgtttccgc   1260

aagcatccgg aagccacata ctctcggtgc ggctccggtc cctggattac acccaggtgc   1320

atggtcgact acccgtatag gctttggcac tatccttgta ccatcaatta caccatattc   1380

aaagtcagga tgtacgtggg aggggtcgag cacaggctgg aagcggcctg caactggacg   1440

cggggcgaac gctgtgatct ggaagacagg gacaggtccg agctcagccc attgctgctg   1500

tccaccacac agtggcaggt ccttccgtgt tctttcacga ccctgccagc cttgtccacc   1560

ggcctcatcc acctccacca gaacattgtg gacgtgcagt acttgtacgg ggtagggtca   1620

agcatcgcgt cctgggccat taagtgggag tacgtcgttc tcctgttcct cctgcttgca   1680

gacgcgcgcg tctgctcctg cttgtggatg atgttactca tatcccaagc ggaggcgtaa   1740

tctaga                                                               1746
```

<210> SEQ ID NO 9
<211> LENGTH: 1935
<212> TYPE: DNA
<213> ORGANISM: Hepatitis C virus

<400> SEQUENCE: 9

```
aagcttatgg gttgctcttt ctctatcttc cttctggccc tgctctcttg cctgaccgtg     60

cccgcttcag cctaccaagt gcgcaattcc tcggggcttt accatgtcac caatgattgc    120

cctaactcga gtattgtgta cgaggcggcc gatgccatcc tgcacactcc ggggtgtgtc    180

ccttgcgttc gcgagggtaa cgcctcgagg tgttgggtgg cggtgacccc cacggtggcc    240

accagggacg gcaaactccc cacaacgcag cttcgacgtc atatcgatct gcttgtcggg    300

agcgccaccc tctgctcggc cctctacgtg ggggacctgt gcgggtctgt ctttcttgtt    360

ggtcaactgt ttaccttctc tccccggcgc cactggacga cgcaagactg caattgttct    420

atctatcccg gccatataac gggtcatcgc atggcatggg atatgatgat gaactggtcc    480

cctacggcag cgttggtggt agctcagctg ctccggatcc cacaagccat catggacatg    540

atcgctggtg ctcactgggg agtcctggcg ggcatagcgt atttctccat ggtggggaac    600

tgggcgaagg tcctggtagt gctgctgcta tttgccggcg tcgacgcgga aacccacgtc    660

accgggggaa gtgccggccg caccacggct gggcttgttg gtctccttac accaggcgcc    720

aagcagaaca tccaactgat caacaccaac ggcagttggc acatcaatag cacggccttg    780
```

-continued

```
aactgcaatg aaagccttaa caccggctgg ttagcagggc tcttctatca gcacaaattc    840

aactcttcag gctgtcctga gaggttggcc agctgccgac gccttaccga ttttgcccag    900

ggctggggtc ctatcagtta tgccaacgga agcggcctcg acgaacgccc ctactgctgg    960

cactaccctc caagaccttg tggcattgtg cccgcaaaga gcgtgtgtgg cccggtatat   1020

tgcttcactc ccagccccgt ggtggtggga acgaccgaca ggtcgggcgc gcctacctac   1080

agctggggtg caaatgatac ggatgtcttc gtccttaaca acaccaggcc accgctgggc   1140

aattggttcg gttgtacctg gatgaactca actggattca ccaaagtgtg cggagcgccc   1200

ccttgtgtca tcggaggggt gggcaacaac accttgctct gccccactga ttgtttccgc   1260

aagcatccgg aagccacata ctctcggtgc ggctccggtc cctggattac acccaggtgc   1320

atggtcgact acccgtatag gctttggcac tatccttgta ccatcaatta caccatattc   1380

aaagtcagga tgtacgtggg aggggtcgag cacaggctgg aagcggcctg caactggacg   1440

cggggcgaac gctgtgatct ggaagacagg gacaggtccg agctcagccc attgctgctg   1500

tccaccacac agtggcaggt ccttccgtgt tctttcacga ccctgccagc cttgtccacc   1560

ggcctcatcc acctccacca gaacattgtg gacgtgcagt acttgtacgg ggtagggtca   1620

agcatcgcgt cctgggccat taagtgggag tacgtcgttc tcctgttcct cctgcttgct   1680

gacgcgcgcg tctgctcctg cttgtggatg atgttactca tatcccaagc ggaggcggct   1740

ttggagaacc tcgtaatact caatgcagca tccctggccg ggacgcacgg tcttgtgtcc   1800

ttcctcgtgt tcttctgctt tgcgtggtat ctgaagggta ggtgggtgcc cggagcggtc   1860

tacgccttct acgggatgtg gcctctcctc ctgctcctgc tggcgttgcc tcagcgggca   1920

tacgcataat ctaga                                                   1935
```

```
<210> SEQ ID NO 10
<211> LENGTH: 444
<212> TYPE: DNA
<213> ORGANISM: Hepatitis C virus

<400> SEQUENCE: 10

aagcttatgg gttgctcttt ctctatcttc cttctggccc tgctctcttg cctgaccgtg     60

cccgcttcag cctaccaagt gcgcaattcc tcggggcttt accatgtcac caatgattgc    120

cctaactcga gtattgtgta cgaggcggcc gatgccatcc tgcacactcc ggggcgccac    180

tggacgacgc aagactgcaa ttgttctatc tatcccggcc atataacggg tcatcgcatg    240

gcatgggata tgatgatgaa ctggtcccct acggcagcgt tggtggtagc tcagctgctc    300

cggatcccac aagccatcat ggacatgatc gctggtgctc actggggagt cctggcgggc    360

atagcgtatt tctccatggt ggggaactgg gcgaaggtcc tggtagtgct gctgctattt    420

gccggcgtcg acgcgtaatc taga                                           444


<210> SEQ ID NO 11
<211> LENGTH: 34
<212> TYPE: DNA
<213> ORGANISM: Hepatitis C virus

<400> SEQUENCE: 11

aaaaaaaagc ttatgagcac gaatcctaaa cctc                                 34


<210> SEQ ID NO 12
<211> LENGTH: 35
<212> TYPE: DNA
```

-continued

<213> ORGANISM: Hepatitis C virus

<400> SEQUENCE: 12
aaaaaatcta gattatgcgt atgcccgctg aggca 35

<210> SEQ ID NO 13
<211> LENGTH: 34
<212> TYPE: DNA
<213> ORGANISM: Hepatitis C virus

<400> SEQUENCE: 13
aaaaaaaagc ttatgagcac gaatcctaaa cctc 34

<210> SEQ ID NO 14
<211> LENGTH: 27
<212> TYPE: DNA
<213> ORGANISM: Hepatitis C virus

<400> SEQUENCE: 14
aaaaaatcta gattacgcct ccgcttg 27

<210> SEQ ID NO 15
<211> LENGTH: 33
<212> TYPE: DNA
<213> ORGANISM: Hepatitis C virus

<400> SEQUENCE: 15
aaaaaaaagc ttatggacct catggggtac ata 33

<210> SEQ ID NO 16
<211> LENGTH: 27
<212> TYPE: DNA
<213> ORGANISM: Hepatitis C virus

<400> SEQUENCE: 16
aaaaaatcta gattacgcct ccgcttg 27

<210> SEQ ID NO 17
<211> LENGTH: 33
<212> TYPE: DNA
<213> ORGANISM: Hepatitis C virus

<400> SEQUENCE: 17
aaaaaaaagc ttatgggttg ctctttctct atc 33

<210> SEQ ID NO 18
<211> LENGTH: 35
<212> TYPE: DNA
<213> ORGANISM: Hepatitis C virus

<400> SEQUENCE: 18
aaaaaatcta gattatgcgt atgcccgctg aggca 35

<210> SEQ ID NO 19
<211> LENGTH: 33
<212> TYPE: DNA
<213> ORGANISM: Hepatitis C virus

<400> SEQUENCE: 19
aaaaaaaagc ttatgggttg ctctttctct atc 33

<210> SEQ ID NO 20
<211> LENGTH: 27

-continued

```
<212> TYPE: DNA
<213> ORGANISM: Hepatitis C virus

<400> SEQUENCE: 20

aaaaaatcta gattacgcct ccgcttg                                    27
```

SEQUENCES ENCODING HEPATITIS C VIRUS GLYCOPROTEINS

This application claims the benefit of U.S. Provisional Application No. 60/519,536, filed Nov. 12, 2003, the contents of which are incorporated herein by reference.

The invention disclosed herein was made with United States Government support under grant number AI051134 from the National Institutes of Health, U.S. Department of Health and Human Services. Accordingly, the United States Government has certain rights in this invention.

Throughout this application, various publications are referenced in parentheses by author name and date. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein. However, the citation of a reference herein should not be construed as an acknowledgement that such reference is prior art to the present invention.

BACKGROUND OF THE INVENTION

Hepatitis C virus (HCV) was first recognized in 1989. It infects the liver and is responsible for the majority of cases of non-A, non-B hepatitis (Alter and Seef, 1993). Infections are typically chronic and lifelong; many infected individuals are healthy and unaffected for decades, whereas others develop chronic hepatitis or liver cirrhosis, the latter often leading to hepatocellular carcinoma (Fry and Flint, 1997; Lauer and Walker, 2001). While screening of the blood supply has drastically reduced new transmissions of the virus, there exists a large cohort of infected individuals who will require treatment in the coming decades. Some reports estimate that nearly 3% of the world's population or about 170 million people worldwide, including about 4 million people in the U.S.A., are infected with HCV (Anon, 1999).

HCV infection and its clinical sequelae are the leading causes of liver transplantation in the U.S.A. No vaccine is currently available, and the two licensed therapies, interferon alpha and ribavirin, which are both non-specific antiviral agents with incompletely understood mechanisms of action, are only modestly efficacious (McHutchison et al., 1998). Thus, whereas the best long-term response rates are obtained with a combination of interferon alpha-2b and ribavirin, only a minority of subjects treated with this combination achieves the desired result of no detectable serum HCV RNA six months after stopping treatment (McHutchison et al., 1998). Moreover, these drugs exhibit severe, life-threatening toxicities, including neutropenia, hemolytic anemia and severe depression. There is therefore an urgent need for the development of new therapeutic approaches and agents to combat HCV infection.

The development of new treatments for HCV infection would be facilitated by a detailed knowledge of how the virus attaches to and fuses with cell membranes, enters target cells, replicates therein, infects neighboring cells and induces disease symptoms. However, even a basic understanding of HCV replication and pathogenesis remains poor, primarily due to a lack of experimental models and key reagents. An important step, therefore, is the development of better model systems that will facilitate the elucidation of the mechanisms underlying various aspects of the viral life cycle and disease causation.

The HCV genome is a 9.6 kb positive-sense, single-stranded RNA molecule that replicates exclusively in the cytoplasm of infected cells (Rice, 1996). The genomic RNA encodes a ~3000 amino acid polyprotein that is processed to generate at least ten proteins termed C, E1, E2, p7, NS2, NS3, NS4A, NS4B, NS5A and NS5B (Grakoui et al., 1993; Rice, 1996; Lauer and Walker, 2001). The C protein constitutes the nucleocapsid; E1 and E2 are transmembrane envelope glycoproteins; p7 is a membrane spanning protein of unknown function; and the various non-structural (NS) proteins have replication functions (Bartenschlager and Lohmann, 2000; Op De Beeck et al., 2001).

The envelope glycoproteins are thought to play a crucial role in viral infectivity through their direct effect on various processes including the packaging of virions, the attachment of virions to target cells, fusion with and entry into these cells, and the budding of viruses from cell membranes before another round of cell infection can be initiated. HCV entry into target cells is a particularly attractive target for antiviral therapy because entry inhibitors do not need to cross the plasma membrane nor be modified intracellularly. In addition, viral entry is generally a rate-limiting step that is mediated by conserved structures on the viral envelope and cell membrane. Consequently, inhibitors of viral entry can provide potent and durable suppression of viral replication.

HCV entry into host cells requires attachment of the viral particle to the cell surface, followed by fusion of the viral envelope with the cellular membrane. The HCV envelope glycoproteins, E1 and E2, are thought to be involved in mediating virus entry into susceptible target cells. In mammalian cell-based expression systems, the molecular weight of mature, full length E1 is ~35 kD and that of E2 is ~72 kD (Grakoui et al., 1993; Matsuura et al., 1994; Spaete et al., 1992). E1 and E2 are present as a non-covalently associated heterodimer, hereinafter referred to as E1/E2, on the virus surface and undergo extensive posttranslational modification by N-linked glycosylation (Lauer and Walker, 2001).

Entry of the HCV structural proteins, C-E1-E2-p7, into the cell is followed by translocation into the endoplasmic reticulum (ER), which is accompanied by cleavage of internal signal sequences by ER-resident signal peptidases (Bartenschlager and Lohmann, 2000; Op De Beeck et al., 2001; Reed and Rice, 2000). It is assumed that HCV buds into the ER and matures by passage through cytoplasmic vesicles (Pettersson, 1991). Studies of the subcellular localization of HCV envelope glycoproteins and particles in cells transfected or infected in vitro suggest vesicle-based morphogenesis of HCV (Dash et al., 1997; Egger et al., 2002; Greive et al., 2002; Iocovacci et al., 1997; Pietschmann et al., 2002; Serafino et al., 1997; Shimizu et al., 1996). However, HCV-like particles have been detected in the cytoplasm of hepatocytes from infected patients, which suggests budding at the plasma membrane (DeVos et al., 2002), though the budding and maturation process of HCV have not yet been delineated.

The two most common experimental models of viral entry are cell-cell membrane fusion between receptor- and envelope glycoprotein-expressing cells, and entry of "reporter" viruses pseudotyped with heterologous envelope glycoproteins. Both systems rely on cell surface-associated expression of functional envelope glycoproteins. However, achieving expression of E1 and E2 on the surface of cells has proven to be elusive, and various studies have suggested that modification of the TM domains may be required. Two groups (Lagging et al., 1998; Takikawa et al., 2000) have described fusion and entry mediated by E1 and E2 ectodomains fused to the TM domain of the VSV G envelope glycoprotein. However, the TM domain of VSV G has no known dimerization function, and E1 and E2 were expressed from separate mRNAs, further minimizing their potential to form native heterodimers. It is unclear from these reports whether fusion and entry events were actually mediated by E1 and E2, because key controls demonstrating specificity were omitted.

There has also been some inconsistency in the results reported: one group showed that pH-independent entry of viral pseudotypes was mediated by either E1 or E2 (Lagging et al., 1998; Meyer et al., 2000; Lagging et al., 2002), whereas the other showed that pH-dependent fusion required both glycoproteins (Takikawa et al., 2000; Matsuura et al., 2001). Moreover, a more recent report that HCV-VSV chimeric envelope glycoproteins are not functional (Buonocore et al., 2002), contradicts the results of the earlier studies. It therefore appears that the chimeric VSV G system does not reproducibly model HCV envelope glycoprotein-mediated cell fusion and entry.

The apparent absence of E1/E2 heterodimers on the cell surface and the lack of N-glycan modifications by Golgi enzymes have led to suggestions that HCV envelope glycoproteins are retained in the ER (Duvet et al., 1998; Martire et al., 2001; Michalak et al., 1997; Patel et al., 2001; Selby et al., 1994). Both ER retention of E1/E2 and the heterodimerization of these glycoproteins are thought to be mediated by the TM domains of E1 and E2 (Cocquerel et al., 1999; Cocquerel et al., 1998; Cocquerel et al., 2000; Flint and McKeating, 1999; Flint et al., 1999; (Deleersnyder et al., 1997; Dubuisson et al., 1994; Op De Beeck et al., 2000; Patel et al., 1999; Ralston et al., 1993; Selby et al., 1994), and this has made it difficult to generate cell surface-expressed E1/E2 heterodimers. However, an experimental system for generating such surface-expressed E1/E2 heterodimers would be very valuable, with applications in, for example, the development of assays for measuring the extent of cell membrane fusion and pseudovirion entry and for identifying agents that inhibit HCV entry into susceptible cells, as well as the production of monoclonal antibodies and vaccines.

SUMMARY OF THE INVENTION

The present invention provides a modified nucleic acid comprising consecutive nucleotides having a nucleotide sequence coding for a full length hepatitis C virus (HCV) glycoprotein selected from the group consisting of E1 glycoprotein and E1/E2 glycoprotein heterodimer, this nucleic acid having at least one nucleotide alteration, wherein, due to this alteration, at least one RNA splice site selected from the group consisting of RNA splice acceptor and RNA splice donor sites is eliminated from the coding sequence.

This invention also provides a modified nucleic acid comprising consecutive nucleotides having a nucleotide sequence encoding a truncated hepatitis C virus (HCV) E1 glycoprotein, wherein nucleotides extending from nucleotide positions 675 to 887 inclusive in a coding sequence coding for E1 are deleted, these nucleotide positions being numbered by reference to SEQ ID NO:2.

This invention further provides an expression vector comprising any one of the modified nucleic acids described herein.

This invention still further provides a host cell containing therein the expression vector described above. This invention also provides a method for expressing on a cell surface a hepatitis C virus (HCV) glycoprotein, selected from the group consisting of E1 glycoprotein and E1/E2 glycoprotein heterodimer, wherein the majority of the glycoprotein is full length, which method comprises transfecting a cell with an expression vector comprising a modified HCV coding sequence, selected from the group consisting of the E1 and E1-E2 coding sequences, wherein at least one nucleotide alteration in the modified coding sequence eliminates at least one RNA splice site selected from the group consisting of RNA splice acceptor and RNA splice donor sites so as to reduce the extent of excision of an intron from the modified coding sequence, under conditions suitable for nuclear transcription of the modified coding sequence, such that the glycoprotein is expressed on the cell surface.

This invention further provides a cell expressing on a surface thereof a hepatitis C virus (HCV) glycoprotein selected from the group consisting of E1 glycoprotein and E1/E2 glycoprotein heterodimer, wherein the glycoprotein is expressed from a modified HCV coding sequence according to any of the methods described herein.

This invention additionally provides a cell-surface-localized hepatitis C virus (HCV) glycoprotein, selected from the group consisting of E1 glycoprotein and E1/E2 glycoprotein heterodimer, wherein the glycoprotein is expressed from a modified HCV coding sequence according to any of the methods described herein.

This invention also provides a method for making a pseudovirion expressing on a surface thereof a hepatitis C virus (HCV) glycoprotein selected from the group consisting of E1 glycoprotein and E1/E2 glycoprotein heterodimer, wherein the majority of the glycoprotein is full length, which method comprises (a) co-transfecting a cell with (1) at least one vector which provides virion packaging functions and expresses a reporter gene, and (2) a vector construct comprising a modified HCV coding sequence, selected from the group consisting of E1 and E1-E2 coding sequences, wherein at least one nucleotide alteration in the coding sequence eliminates at least one RNA splice site selected from the group consisting of RNA splice acceptor and RNA splice donor sites from the modified HCV coding sequence so as to reduce the extent of excision of an intron from the modified coding sequence; and (b) collecting viral supernatant containing pseudovirions.

This invention further provides a pseudovirion expressing on its surface a hepatitis C virus (HCV) glycoprotein, selected from the group consisting of E1 glycoprotein and E1/E2 glycoprotein heterodimer, wherein the majority of the glycoprotein is full length.

This invention still further provides an immunogen comprising any one of the hepatitis C virus (HCV) pseudovirions described herein.

This invention also provides a pharmaceutical composition comprising any one of the hepatitis C virus (HCV) pseudovirions described herein and a pharmaceutically acceptable carrier.

This invention further provides a method for producing a polyclonal antibody that specifically binds to hepatitis C virus (HCV) comprising: (a) injecting into a subject an immunogen comprising an HCV pseudovirion to induce a primary immune response in said subject; (b) administering at least one booster injection of pseudovirion to the subject; and (c) purifying from the subject's serum a polyclonal antibody that binds specifically to HCV.

This invention still further provides a polyclonal antibody that specifically binds to HCV.

This invention also provides a method for producing a monoclonal antibody that specifically binds to hepatitis C virus (HCV) comprising: (a) injecting into a subject an immunogen comprising an HCV pseudovirion to induce a primary immune response in the subject; (b) administering at least one booster injection of pseudovirion to the subject; (c) harvesting antibody-producing lymphatic cells from the subject; (d) generating hybridomas by fusing single antibody-producing cells obtained in (c) with myeloma cells; and (e) screening hybridoma supernatants from these hybridomas to identify at least one monoclonal antibody that specifically binds to HCV.

This invention further provides a monoclonal antibody that specifically binds to HCV.

This invention still further provides a nucleic acid molecule encoding a monoclonal antibody or fragment thereof that specifically binds to HCV.

In addition, this invention provides a method for expressing in a cell a modified hepatitis C virus (HCV) glycoprotein selected from the group consisting of modified E1 glycoprotein and modified E1/E2 glycoprotein heterodimer, wherein the glycoprotein produced is homogeneously truncated by a deletion of amino acid residues 226 to 296 inclusive, these amino acid residues being numbered by reference to SEQ ID NO:3, which method comprises transfecting a cell with an expression vector comprising a modified coding sequence, wherein a nucleotide sequence corresponding to a putative intron between nucleotide positions 675 and 887 inclusive is deleted, these nucleotide positions being numbered by reference to SEQ ID NO:2, under conditions suitable for expression of vector-encoded glycoprotein, so as to express a homogeneously truncated glycoprotein lacking amino acid residues 226 to 296 inclusive, these amino acid residues being numbered by reference to SEQ ID NO:3.

This invention also provides a modified hepatitis C virus (HCV) glycoprotein, selected from the group consisting of modified E1 glycoprotein and modified E1/E2 glycoprotein heterodimer, wherein the modified glycoprotein is homogeneously truncated by a deletion of amino acid residues 226 to 296 inclusive, these amino acid residues being numbered by reference to SEQ ID NO:3.

This invention further provides a method for determining whether an agent inhibits fusion of hepatitis C virus (HCV) to a target cell capable of fusing with HCV, which method comprises (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of an agent under conditions which would normally permit fusion of the target cell to the cell expressing HCV E1/E2 glycoprotein dimer on its surface in the absence of the agent, wherein the first and second dyes are selected so as to allow resonance energy transfer between the dyes; (b) exposing the contacted cells to conditions which would result in resonance energy transfer if fusion has occurred; and (c) determining whether there is a reduction of resonance energy transfer in the presence of the agent compared with the resonance energy transfer in the absence of the agent; wherein a reduction in resonance energy transfer in the presence of the agent indicates that the agent inhibits fusion of HCV to the target cell.

This invention still further provides a method for screening a plurality of agents, not known to inhibit fusion of hepatitis C virus (HCV) to a target cell capable of fusing with this virus, to identify at least one agent that inhibits such fusion, which method comprises (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of a plurality of agents under conditions which would normally permit fusion of the target cell to the cell expressing HCV E1/E2 glycoprotein dimer on its surface in the absence of the plurality of agents, wherein the first and second dyes are selected so as to allow resonance energy transfer between the dyes; (b) exposing the contacted cells to conditions which would result in resonance energy transfer if fusion has occurred; (c) determining whether there is a reduction of resonance energy transfer in the presence of the plurality of agents compared with the resonance energy transfer in the absence of the plurality of agents; and (d) if the resonance energy transfer is reduced in the presence of the plurality of agents, separately determining which of the agents present in the plurality of agents causes a reduction in resonance energy transfer, so as to thereby identify at least one agent that inhibits fusion of HCV to a target cell.

The present invention additionally provides an agent that inhibits fusion of hepatitis C virus (HCV) to a target cell capable of fusing with HCV.

This invention also provides a pharmaceutical composition comprising any of the agents described herein and a pharmaceutically acceptable carrier.

This invention further provides a method for determining whether an agent inhibits entry of hepatitis C virus (HCV) into a target cell susceptible to infection by HCV, comprising (a) separately contacting (1) a pseudovirion expressing HCV E1/E2 glycoprotein heterodimer on its surface, wherein a majority of the E1/E2 glycoprotein is full length, which pseudovirion was produced using at least one vector which provides virion packaging functions and expresses a reporter gene, with (2) a target cell in the presence and absence of an agent under conditions which would normally permit entry of the pseudovirion into the target cell in the absence of the agent; and (b) lysing the contacted target cell and determining whether there is a reduction in reporter gene activity in the presence of the agent compared with reporter gene activity in the absence of the agent; wherein a reduction in reporter gene activity in the presence of the agent indicates that the agent inhibits entry of HCV into the target cell.

This invention still further provides a method for screening a plurality of agents, not known to inhibit entry of hepatitis C virus (HCV) into a target cell susceptible to infection by HCV, to identify at least one agent that inhibits such entry, which method comprises (a) separately contacting (1) a pseudovirion expressing HCV E1/E2 glycoprotein heterodimer on its surface, wherein a majority of the E1/E2 glycoprotein is full length, which pseudovirion was produced using at least one vector which provides virion packaging functions and expresses a reporter gene, with (2) a target cell in the presence and absence of a plurality of agents under conditions which would normally permit entry of the pseudovirion into the target cell in the absence of the plurality of agents; (b) lysing the contacted target cell and determining whether there is a reduction in reporter gene activity in the presence of the plurality of agents compared with the reporter gene activity in the absence of the plurality of agents; and (c) if the reporter gene activity is reduced in the presence of the plurality of agents, separately determining which of the agents present in the plurality of agents causes a reduction in reporter gene activity, so as to thereby identify at least one agent that inhibits entry of HCV into a target cell.

Additionally, this invention provides an agent that inhibits entry of hepatitis C virus (HCV) into a target cell susceptible to infection by HCV.

This invention also provides a pharmaceutical composition comprising any of the agents described herein and a pharmaceutically acceptable carrier.

This invention further provides a method for treating a subject afflicted with a hepatitis C virus (HCV)-associated disorder, which treatment is effected by inhibiting fusion of HCV to a target cell capable of fusing with this virus, which method comprises administering to the subject an agent, wherein this agent is (1) determined to inhibit fusion of HCV to a target cell capable of fusing with HCV using a method comprising (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of the agent under conditions which would normally permit fusion of the target cell to the cell expressing HCV E1/E2 glycoprotein dimer on its surface in the absence of the agent, wherein the first and second dyes are selected so as to allow resonance energy transfer between the dyes; (b) exposing the contacted cells to conditions which would result in resonance energy transfer if fusion has occurred; and (c) determining whether there is a reduction of resonance energy transfer in the presence of the agent compared with the resonance energy transfer in the absence of the agent; wherein a reduction in resonance energy transfer in the presence of the agent indicates that the agent inhibits fusion of HCV to the target cell, and (2) administered in a therapeutically effective amount to treat the subject.

This invention still further provides a method for treating a subject afflicted with a hepatitis C virus (HCV)-associated disorder, which treatment is effected by inhibiting entry of HCV into a target cell susceptible to infection by this virus, which method comprises administering to the subject an agent, wherein this agent is (1) determined to inhibit entry of HCV into a target cell using a method comprising: (a) separately contacting a pseudovirion expressing HCV E1/E2 glycoprotein heterodimer on its surface, wherein the majority of the E1/E2 glycoprotein is full length, which pseudovirion was produced using a packaging vector that expresses a reporter gene, with a target cell in the presence and absence of the agent under conditions which would normally permit entry of the pseudovirion into the target cell in the absence of the agent; and (b) lysing the contacted target cell and determining whether there is a reduction in reporter gene activity in the presence of the agent compared with the reporter gene activity in the absence of the agent; wherein a reduction in reporter gene activity in the presence of the agent indicates that the agent inhibits entry of HCV into the target cell; and (2) administered in a therapeutically effective amount to treat the subject.

This invention additionally provides a method for preventing a hepatitis C virus (HCV) infection in a subject, the prevention of which is effected by inhibiting fusion of HCV to a target cell capable of fusing with this virus, which method comprises administering to the subject an agent, wherein this agent is (1) determined to inhibit fusion of HCV to a target cell capable of fusing with HCV using a method comprising: (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of the agent under conditions which would normally permit fusion of the target cell to the cell expressing HCV E1/E2 glycoprotein dimer on its surface in the absence of the agent, wherein the first and second dyes are selected so as to allow resonance energy transfer between the dyes; (b) exposing the contacted cells to conditions which would result in resonance energy transfer if fusion has occurred; and (c) determining whether there is a reduction of resonance energy transfer in the presence of the agent compared with the resonance energy transfer in the absence of the agent; wherein a reduction in resonance energy transfer in the presence of the agent indicates that the agent inhibits fusion of HCV to the target cell; and (2) administered in a prophylactically effective amount to prevent an HCV infection in the subject.

This invention also provides a method for inhibiting in a subject the onset of a hepatitis C virus (HCV)-associated disorder, the inhibition of which is effected by inhibiting fusion of HCV to a target cell capable of fusing with this virus, which method comprises administering to the subject an agent, wherein this agent is (1) determined to inhibit fusion of HCV to a target cell capable of fusing with HCV using a method comprising (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of the agent under conditions which would normally permit fusion of the target cell to the cell expressing HCV E1/E2 glycoprotein dimer on its surface in the absence of the agent, wherein the first and second dyes are selected so as to allow resonance energy transfer between the dyes; (b) exposing the contacted cells to conditions which would result in resonance energy transfer if fusion has occurred; and (c) determining whether there is a reduction of resonance energy transfer in the presence of the agent compared with the resonance energy transfer in the absence of the agent; wherein a reduction in resonance energy transfer in the presence of the agent indicates that the agent inhibits fusion of HCV to the target cell; and (2) administered in a prophylactically effective amount to have a prophylactic effect in the subject.

This invention further provides a method for preventing a hepatitis C virus (HCV) infection in a subject, the prevention of which is effected by inhibiting entry of HCV into a target cell susceptible to infection by this virus, which method comprises administering to the subject an agent, wherein this agent is (1) determined to inhibit entry of HCV into a target cell using a method comprising: (a) separately contacting a pseudovirion expressing HCV E1/E2 glycoprotein heterodimer on its surface, wherein the majority of the E1/E2 glycoprotein is full length, which pseudovirion was produced using a packaging vector that expresses a reporter gene, with a target cell in the presence and absence of the agent under conditions which would normally permit entry of the pseudovirion into the target cell in the absence of the agent; and (b) lysing the contacted target cell and determining whether there is a reduction in reporter gene activity in the presence of the agent compared with the reporter gene activity in the absence of the agent; wherein a reduction in reporter gene activity in the presence of the agent indicates that the agent inhibits entry of HCV into the target cell; and (2) administered in a prophylactically effective amount to prevent an HCV infection in the subject.

This invention still further provides a method for inhibiting in a subject the onset of a hepatitis C virus (HCV)-associated disorder, the inhibition of which is effected by inhibiting entry of HCV into a target cell susceptible to infection by this virus, which method comprises administering to the subject an agent, wherein this agent is (1) determined to inhibit entry of HCV into a target cell using a method comprising: (a) separately contacting a pseudovirion expressing HCV E1/E2 glycoprotein heterodimer on its surface, wherein the majority of the E1/E2 glycoprotein is full length, which pseudovirion was produced using a packaging vector that expresses a reporter gene, with a target cell in the presence and absence of the agent under conditions which would normally permit entry of the pseudovirion into the target cell in the absence of the agent; and (b) lysing the contacted target cell and determining whether there is a reduction in reporter gene activity in the presence of the agent compared with the reporter gene activity in the absence of the agent; wherein a reduction in reporter gene activity in the presence of the agent indicates that the agent inhibits entry of HCV into the target cell; and (2) administered in a prophylactically effective amount to have a prophylactic effect in the subject.

The present invention also provides a method for preventing a hepatitis C virus (HCV) infection in a subject, the prevention of which is effected by immunizing the subject, which method comprises: (a) injecting into the subject a pharmaceutical composition comprising an HCV pseudovirion expressing on its surface a hepatitis C virus (HCV) glycoprotein selected from the group consisting of E1 glycoprotein and E1/E2 glycoprotein heterodimer, wherein the majority of the glycoprotein is full length; and thereby (b) eliciting a protective HCV immune response in the subject.

This invention further provides a method for inhibiting in a subject the onset of a hepatitis C virus (HCV)-associated disorder, the inhibition of which is effected by immunizing the subject, which method comprises: (a) injecting into the subject a pharmaceutical composition comprising an HCV pseudovirionexpressing on its surface a hepatitis C virus (HCV) glycoprotein selected from the group consisting of E1 glycoprotein and E1/E2 glycoprotein heterodimer, wherein the majority of the glycoprotein is full length; and thereby (b) eliciting a protective HCV immune response in the subject.

This invention still further provides a diagnostic kit comprising an antibody as described herein and instructions for using this antibody to detect hepatitis C virus (HCV) in human tissue.

This invention also provides an article of manufacture comprising a packaging material containing therein a modified nucleic acid molecule as described herein and a label providing instructions for using this modified nucleic acid to express on a cell surface a hepatitis C virus (HCV) glycoprotein selected from the group consisting of E1 glycoprotein and E1/E2 glycoprotein heterodimer, wherein the majority of the expressed glycoprotein is full length.

This invention further provides an article of manufacture comprising a packaging material containing therein a modified nucleic acid molecule as described herein and a label providing instructions for using the modified nucleic acid to generate a pseudovirion expressing on its surface a hepatitis C virus (HCV) glycoprotein selected from the group consisting of E1 glycoprotein and E1/E2 glycoprotein heterodimer, wherein the majority of the expressed glycoprotein is full length.

This invention still further provides an article of manufacture comprising a packaging material containing therein a cell expressing on the cell surface a hepatitis C virus (HCV) glycoprotein selected from the group consisting of E1 glycoprotein and E1/E2 glycoprotein heterodimer, wherein the majority of the glycoprotein is full length, and a label providing instructions for using the cell to identify an agent that inhibits fusion of HCV to a target cell capable of fusing with this virus.

Additionally, this invention provides an article of manufacture comprising a packaging material containing therein a pseudovirion expressing on its surface a hepatitis C virus (HCV) glycoprotein selected from the group consisting of E1 glycoprotein and E1/E2 glycoprotein heterodimer, wherein the majority of the glycoprotein is full length, and a label providing instructions for using the pseudovirion to identify an agent that inhibits entry of HCV into a target cell susceptible to infection by this virus.

This invention also provides an article of manufacture comprising a packaging material containing therein an agent as described herein and a label providing instructions for using this agent to treat a subject afflicted with a hepatitis C virus (HCV)-associated disorder, treatment to which is effected by inhibiting fusion of HCV to a target cell capable of fusing with this virus.

This invention further provides an article of manufacture comprising a packaging material containing therein an agent as described herein and a label providing instructions for using this agent to treat a subject afflicted with a hepatitis C virus (HCV)-associated disorder, treatment to which is effected by inhibiting entry of HCV into a target cell susceptible to infection by this virus.

This invention still further provides an article of manufacture comprising a packaging material containing therein an agent as described herein and a label providing instructions for using this agent to inhibit in a subject the onset of a hepatitis C virus (HCV)-associated disorder, the inhibition of which is effected by inhibiting fusion of HCV to a target cell capable of fusing with this virus.

This invention also provides an article of manufacture comprising a packaging material containing therein an agent as described herein and a label providing instructions for using this agent to inhibit in a subject the onset of a hepatitis C virus (HCV)-associated disorder, the inhibition of which is effected by inhibiting entry of HCV into a target cell susceptible to infection by this virus.

BRIEF DESCRIPTION OF THE FIGURES

FIG. 1. Full length consensus sequence of the HCV genome. The genomic sequence (SEQ ID NO:1) shown in (a)-(c) is taken from Yanagi et al. (1997) (Genbank Accession #AF011751). Noncoding sequences are underlined.

FIG. 2. Consensus sequence coding for HCV structural proteins. This sequence (SEQ ID NO:2) encodes the C, E1, E2 and p7 proteins. The first nucleotide in the translation initiation codon of the sequence encoding the C (capsid) protein is numbered 1.

FIG. 3. Full length HCV consensus amino acid sequence. This sequence (SEQ ID NO:3) shown in (a) and (b) is the amino acid sequence deduced from the coding region of consensus HCV genome sequence (SEQ ID NO:1).

FIG. 4. Nucleotide sequence of the 5'-HindIII-C-E1-E2-p7-XbaI-3' construct. Restriction sites are shown in italics, whereas the translation start and stop codons are in bold and underlined. The sequence shown is designated SEQ ID NO:4.

FIG. 5. Nucleotide sequence of the 5'-HindIII-C-E1-E2-XbaI-3' construct. Restriction sites are shown in italics, whereas the translation start and stop codons are in bold and underlined. The sequence shown is designated SEQ ID NO:5.

FIG. 6. Nucleotide sequence of the 5'-HindIII-ΔC-E1*-E2*-XbaI-3' construct. This construct contains a sequence encoding an N-terminally truncated portion (ΔC) of the wild type HCV core protein that serves as a signal sequence (described in PCT International Publication WO 204/024904), and modified E1 and E2 genes (indicated by "*") with mutations of the putative splice sites at positions 675, 887 and 2183. The wild type HCV signal sequence from the core protein is thought to be required for proper folding of the E1/E2 proteins. Restriction sites are shown in italics, whereas the translation start and stop codons are in bold and underlined. The sequence shown is designated SEQ ID NO:6.

FIG. 7. Nucleotide sequence of the 5'-HindIII-E1-E2-p7-XbaI-3' construct. Restriction sites are shown in italics, whereas the translation start and stop codons are in bold and underlined. The sequence shown is designated SEQ ID NO:7.

FIG. 8. Nucleotide sequence of the 5'-HindIII1-E1-E2-XbaI-3' construct. Restriction sites are shown in italics, whereas the translation start and stop codons are in bold and underlined. The sequence shown is designated SEQ ID NO:8.

FIG. 9. Nucleotide sequence of the 5'-HindIII-E1-E2-p7-XbaI-3' construct containing A866C and A2183T double mutations. Restriction sites are shown in italics. The translation start and stop codons as well as nucleotides altered by site-specific mutagenesis are in bold and underlined. The sequence shown is designated SEQ ID NO:9.

FIG. 10. Nucleotide sequence of the 5'-HindIII-E1-XbaI-3' construct with the putative intron deleted. Restriction sites are shown in italics whereas the translation start and stop codons are in bold and underlined. The sequence shown is designated SEQ ID NO:10.

FIG. 13. Excision of a putative intron in E1 mRNA generates a deleted protein. The HCV genome was analyzed with a splice site prediction neural network. (a) Sequences in the E1-E2-p7 coding region having >80% probability of being functional splice donor (SD) and acceptor (SA) sites are indicated. Splicing occurs between nucleotide positions 675 and 887 generating an E1 protein with a deletion spanning amino acids 230 to 292. (b) Unmodified E1 (E1), E1 with a mutated splice acceptor site (E1*), or E1 lacking a putative intron ($E1^{\Delta}_{HCV}$) were transiently expressed in HeLa cells by lipofection and analyzed by immunoblotting with anti-E1 MAb A4. The black arrowhead indicates the position of full length E1 and the white arrowhead indicates the position of the deleted E1 protein species.

DETAILED DESCRIPTION OF THE INVENTION

Definitions

Figure 11:
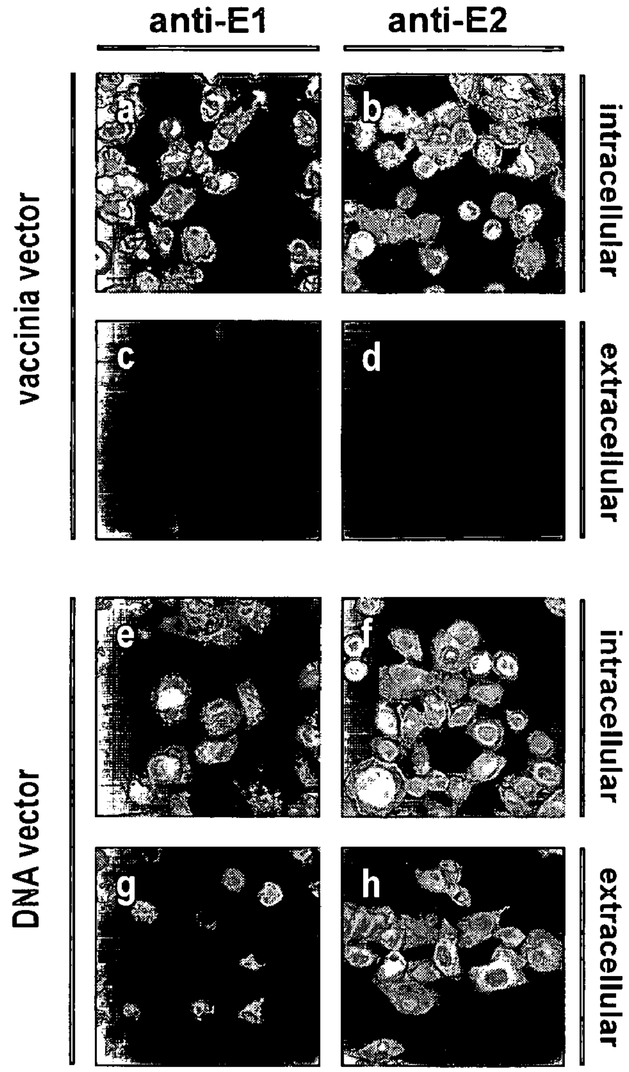
FIG. 11. Cell surface expression of E1 and E2. Unmodified HCV envelope glycoprotein genes were transiently expressed in HeLa cells using either a vaccinia virus vector system (a-d) or lipofection with plasmid DNA constructs (e-h), and protein expression was analyzed 24 h post-infection. Cells were fixed in 3% formaldehyde for 20 min at room temperature (c, d, g, h) or fixed/permeabilized with methanol for 20 min at −20° C. (a, b, e, f). E1 and E2 expression on the cell surface was detected by incubation with the anti-E1 monoclonal antibody (MAb), A4 (a, c, e, g), or the anti-E2 MAb, H53 (b, d, f, h), and visualized by chemifluorescence under a fluorescence microscope (see Methods for details).

As used in this application, except as otherwise expressly provided herein, each of the following terms shall have the meaning set forth below.

"Administering" shall mean delivering in a manner which is effected or performed using any of the various methods and delivery systems known to those skilled in the art. Administering can be performed, for example, topically, intravenously, pericardially, orally, parenterally, via implant, trans-mucosally, transdermally, intradermally, intramuscularly, subcutaneously, intraperitoneally, intrathecally, intralymphatically, intra-lesionally, or epidurally. An agent or composition may also be administered in an aerosol, such as for pulmonary and/or intranasal delivery. Administering can also be performed, for example, once, a plurality of times, and/or over one or more extended periods.

"Attachment" of HCV or a pseudovirion to a target cell shall mean the process that is mediated by the binding of the HCV envelope glycoprotein to a ligand, e.g., L-SIGN, present on the surface of a cell susceptible to HCV infection. This process is distinguished from the fusion of HCV or a pseudovirion with, and entry into a target cell. "Fusion" shall mean the joining or union of the lipid bilayer membranes found on mammalian cells or viruses such as HCV. The fusion of the cell membrane of a cell susceptible to HCV infection with an HCV envelope glycoprotein$^+$ cell membrane shall mean the hydrophobic joining and integration of the cell membrane of the infection-susceptible cell with the HCV envelope glycoprotein$^+$ membrane to form a hybrid membrane comprising components of both cell membranes. In one embodiment, the host cell is a bodily cell from a subject, such as from a human subject. "Entry" shall mean the process whereby viral genetic information is introduced into a host cell. HCV entry into a host cell requires prior attachment of the viral particle to the cell surface, followed by fusion of the viral envelope with the cellular membrane. The overall process of HCV attachment, fusion and entry results in "HCV infection" of a host cell. Infection is usually but not necessarily accompanied by the induction of disease symptoms in a subject.

A "cell" includes a biological cell, e.g., a HeLa cell, and a non-biological cell, e.g., a phospholipid vesicle or virion. A "cell susceptible to HCV infection" may also be referred to as a "target cell" and includes cells capable of being infected by or fusing with HCV or HCV-infected cells.

A "full length" hepatitis C virus (HCV) glycoprotein is one which is identical in amino acid length and sequence to that of a polypeptide encoded by a corresponding unmodified HCV envelope glycoprotein coding sequence. In particular, such full length HCV glycoprotein is not truncated as a result of the excision of any putative intron sequence from a corresponding unmodified HCV envelope glycoprotein coding sequence.

A "fully human" antibody shall mean an antibody wherein all of the amino acids correspond to amino acids in human immunoglobulin molecules.

A "humanized" antibody shall mean an antibody wherein some, most or all of the amino acids outside the complementarity determining regions (CDRs) are replaced with corresponding amino acids derived from human immunoglobulin molecules.

"HCV" shall mean the hepatitis C virus without limitation to strain, subtype or genotype, such as are disclosed in U.S. Pat. Nos. 6,572,864 and 5,882,852. HCV includes but is not limited to extracellular virus particles and the forms of HCV associated with and/or found in HCV-infected cells.

An "immunogenically effective amount" of an immunogen, such as a pseudovirion, is an amount sufficient to elicit a protective immune response in a subject.

"Inhibiting fusion" of HCV, an HCV pseudovirion or a HCV envelope glycoprotein$^+$ cell with a cell susceptible to HCV infection shall mean (a) reducing the rate of fusion of a cell membrane of a cell susceptible to HCV infection with an HCV envelope, an HCV pseudovirion or a cell membrane of an HCV envelope glycoprotein$^+$ cell by at least 5%, preferably by at least 50%, more preferably by at least 75%, and/or (b) reducing by at least 5%, preferably by at least 50%, more preferably by at least 75%, the total amount of fusion of a cell membrane of a cell susceptible to HCV infection with an HCV envelope, an HCV pseudovirion or an HCV envelope glycoprotein$^+$ cell membrane occurring by the endpoint of fusion. The rate of cell membrane fusion means the total quantity of cell membrane fused per unit of time. The endpoint of fusion means the point in time at which all fusion of cell membranes of cells susceptible to HCV infection with HCV envelope glycoprotein$^+$ cell membrane capable of occurring has occurred.

"Inhibiting entry" of HCV or an HCV pseudovirion into a host cell shall mean reducing the amount of viral genetic information introduced into the host cell as compared to the amount that would be introduced without, for example, an inhibiting agent. In one embodiment, "inhibiting" means that the amount of viral genetic information introduced into the host cell is reduced at least 50%, preferably at least 75%. In a preferred embodiment, the amount of viral genetic information introduced into the host cell is reduced 100%.

A "majority" of a hepatitis C virus (HCV) glycoprotein being full length shall mean that greater than fifty percent of the glycoprotein consists of full length molecules.

"Pharmaceutically acceptable carriers" are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. In addition to carriers described above, a vaccine may further include carriers known in the art such as, for example, thyroglobulin, albumin, tetanus toxoid, polyamino acids such as polymers of D-lysine and D-glutamate, inactivated influenza virus and hepatitis B recombinant protein(s). The vaccine may also include any well known adjuvants such as incomplete Freund's adjuvant, alum, aluminum phosphate, aluminum hydroxide, monophosphoryl lipid A (MPL, GlaxoSmithKline), saponins including QS21 (GlaxoSmithKline), CpG oligonucleotides (Krieg et al., 1995), montanide, vitamin E and various water-in-oil emulsions prepared from biodegradable oils such as squalene and/or tocopherol, Quil A, Ribi Detox, CRL-1005, L-121 and combinations thereof. Preservatives and other additives, such as, for example, antimicrobials, antioxidants, chelating agents, inert gases, and the like may also be included with all the above carriers.

A "prophylactically effective amount" is any amount of an agent which, when administered to a subject prone to suffer from a disorder, inhibits the onset of the disorder. "Inhibiting" the onset of a disorder means either lessening the likelihood of the disorder's onset, or preventing the onset of the disorder entirely. In the preferred embodiment, inhibiting the onset of a disorder means preventing its onset entirely.

A "protective immune response" against hepatitis C virus (HCV) shall mean an immune response that prevents infection or inhibits the spread of infection from cell to cell after an initial exposure of a subject to the virus. Such immune response, elicited, for example, by administration of an HCV pseudovirion, may include generation of anti-HCV antibodies and/or generation of a cellular immune response (e.g., activation of cytotoxic T lymphocytes).

"Subject" means any animal, such as a mammal or a bird, including, without limitation, a human, a non-human primate, a cow, a horse, a sheep, a pig, a dog, a cat, a rabbit, a rodent such as a mouse, rat or guinea pig, a turkey or a chicken. In a preferred embodiment, the subject is a human being.

A "therapeutically effective amount" is any amount of an agent which, when administered to a subject afflicted with a disorder against which the agent is effective, causes the subject to be treated. With regards to administration of a hepatitis C virus (HCV) pseudovirion immunogen, a therapeutically effective amount shall mean any amount of pseudovirion that is effective in inhibiting spread of HCV (e.g., to limit a chronic infection) and thus alleviates symptoms or prevents further deterioration of liver tissue.

"Treating" a subject afflicted with a disorder shall mean causing the subject to experience a reduction, remission or regression of the disorder and/or its symptoms. In one embodiment, recurrence of the disorder and/or its symptoms is prevented. In the preferred embodiment, the subject is cured of the disorder and/or its symptoms.

"Suitable conditions" shall have a meaning dependent on the context in which this term is used. Generally, it means conditions that permit an agent, capable of doing something, to do that intended thing. In one embodiment, the term "suitable conditions" as used herein means physiological conditions.

"Unmodified" HCV envelope glycoprotein coding sequences shall mean the C, E1, E2 and p7 consensus gene sequences as they occur in the wild-type HCV genome. "Modified" HCV glycoprotein gene sequences shall refer to the in vitro-mutagenized HCV H77 gene sequences containing conservative mutations that remove splice acceptor sites in E1 (A886C and or G888T; modified sequence designated E1*) and E2 (A2183T; modified sequence designated E2*), or a deletion mutation that removes the putative intron in E1 between nucleotide positions 675 and 887 (modified sequence designated $E1^{\Delta}$). Nucleotide positions and mutations are numbered by reference to SEQ ID NO:2. Constructs for expressing these genes in transfected cells may contain modified or unmodified HCV glycoprotein gene sequences singly or in various combinations.

Embodiments of the Invention

Studies on fundamental aspects of HCV replication and infection of susceptible cells have been stymied by a lack of key reagents and experimental systems. The virus replicates poorly or not at all in vitro, and the apparent retention of HCV envelope glycoproteins in the ER has hindered efforts to develop membrane fusion and pseudovirion entry assays which rely on expression of functional envelope glycoproteins on the cell surface. The present invention helps to overcome these obstacles by providing systems for expression of full-length HCV glycoproteins on the cell surface. As described herein, these systems have in turn enabled the development of HCV fusion and entry assays as well as assays for identifying chemical agents that inhibit HCV fusion with and entry into target cells.

Specifically, this invention provides a modified nucleic acid comprising consecutive nucleotides having a nucleotide sequence coding for a full length hepatitis C virus (HCV) glycoprotein selected from the group consisting of E1 glycoprotein and E1/E2 glycoprotein heterodimer, this nucleic acid having at least one nucleotide alteration, wherein, due to this alteration, at least one RNA splice site selected from the group consisting of RNA splice acceptor and RNA splice donor sites is eliminated from the coding sequence. In one embodiment, the modified nucleic acid is an isolated nucleic acid. In another embodiment, elimination of at least one RNA splice acceptor site or splice donor site reduces an extent to which an intron is excised from the coding sequence. In a preferred embodiment, elimination of at least one RNA splice acceptor site or splice donor site prevents excision of an intron from the coding sequence.

In another embodiment of this modified nucleic acid, the alteration comprises an A886C mutation in the HCV E1 coding sequence, this mutation being numbered by reference to SEQ ID NO:2, such that a splice-acceptor site at nucleotide position 887 in SEQ ID NO:2 is eliminated. In a further embodiment, the alteration comprises a G888T mutation in the HCV E1 coding sequence, this mutation being numbered by reference to SEQ ID NO:2, such that a splice-acceptor site at nucleotide position 887 in SEQ ID NO:2 is eliminated. In a still further embodiment, the alteration comprises a G675A mutation in the HCV E1 coding sequence, this mutation being numbered by reference to SEQ ID NO:2, such that a splice donor site at nucleotide position 675 in SEQ ID NO:2 is eliminated. In another embodiment, the alteration comprises an A886C mutation and a G888T mutation in the HCV E1 coding sequence, these mutations being numbered by reference to SEQ ID NO:2, such that a splice-acceptor site at nucleotide position 887 in SEQ ID NO:2 is eliminated. In yet another embodiment, the alteration comprises an A2183T mutation in the E2 coding sequence, this mutation being numbered by reference to SEQ ID NO:2, such that a splice-acceptor site at nucleotide position 2183 in SEQ ID NO:2 is eliminated. In a further embodiment, the alteration comprises an A886C mutation in the HCV E1 coding sequence and an A2183T mutation in the E2 coding sequence, these mutations being numbered by reference to SEQ ID NO:2, such that splice-acceptor sites at nucleotide positions 887 and 2183 in SEQ ID NO:2 are eliminated. In a still further embodiment, the alteration comprises a G888T mutation in the HCV E1 coding sequence and an A2183T mutation in the E2 coding sequence, these mutations being numbered by reference to SEQ ID NO:2, such that splice-acceptor sites at nucleotide positions 887 and 2183 in SEQ ID NO:2 are eliminated. In another embodiment, the alteration comprises an A886C mutation and a G888T mutation in the HCV E1 coding sequence and an A2183T mutation in the E2 coding sequence, these mutations being numbered by reference to SEQ ID NO:2, such that splice-acceptor sites at nucleotide positions 887 and 2183 in SEQ ID NO:2 are eliminated.

This invention also provides a modified nucleic acid comprising consecutive nucleotides having a nucleotide sequence encoding a truncated hepatitis C virus (HCV) E1 glycoprotein, wherein nucleotides extending from nucleotide positions 675 to 887 inclusive in a coding sequence coding for E1 are deleted, these nucleotide positions being numbered by reference to SEQ ID NO:2. In one embodiment, the modified nucleic acid is an isolated nucleic acid molecule. In another embodiment, the modified nucleic acid molecule further comprises a nucleotide sequence encoding an HCV E2 gene and including an alteration comprising an A2183T mutation such that a splice-acceptor site at nucleotide position 2183 in the E2 coding sequence is eliminated, this nucleotide position being numbered by reference to SEQ ID NO:2.

This invention further provides an expression vector comprising any one of the modified nucleic acid molecules described herein.

This invention still further provides a host cell containing therein the expression vector described above.

This invention also provides a method for expressing on a cell surface a hepatitis C virus (HCV) glycoprotein, selected from the group consisting of E1 glycoprotein and E1/E2 glycoprotein heterodimer, wherein the majority of the glycoprotein is full length, which method comprises transfecting a cell with an expression vector comprising a modified HCV coding sequence, selected from the group consisting of the E1 and E1-E2 coding sequences, wherein at least one nucleotide alteration in the modified coding sequence eliminates at least one RNA splice site selected from the group consisting of RNA splice acceptor and RNA splice donor sites so as to reduce the extent of excision of an intron from the modified coding sequence, under conditions suitable for nuclear transcription of the modified coding sequence, such that the glycoprotein is expressed on the cell surface. In one embodiment, a splice-acceptor site at nucleotide position 887 in the HCV E1 coding sequence is eliminated by introduction of an A886C mutation, this nucleotide position and mutation being numbered by reference to SEQ ID NO:2. In another embodiment, a splice-acceptor site at nucleotide position 887 in the HCV E1 coding sequence is eliminated by introduction of a G888T mutation, this nucleotide position and mutation being numbered by reference to SEQ ID NO:2. In a further embodiment, a splice donor site at nucleotide position 675 in the HCV E1 coding sequence is eliminated by introduction of a G675A mutation, this nucleotide position and mutation being numbered by reference to SEQ ID NO:2. In a still further embodiment, a splice-acceptor site at nucleotide position 887 in the HCV E1 coding sequence is eliminated by introduction of an A886C mutation and a G888T mutation, these nucleotide position and mutations being numbered by reference to SEQ ID NO:2. In an additional embodiment, splice-acceptor sites at nucleotide positions 887 in the HCV E1 coding sequence and 2183 in the E2 coding sequence are eliminated by introduction of an A886C mutation and an A2183T mutation, respectively, these nucleotide positions and mutations being numbered by reference to SEQ ID NO:2. In yet another embodiment, splice-acceptor sites at nucleotide positions 887 in the HCV E1 coding sequence and 2183 in the E2 coding sequence are eliminated by introduction of a G888T mutation and an A2183T mutation, respectively, these nucleotide positions and mutations being numbered by reference to SEQ ID NO:2. In a further embodiment, splice-acceptor sites at nucleotide positions 887 in the HCV E1 coding sequence and 2183 in the E2 coding sequence are eliminated by introduction of an A886C mutation, a G888T mutation and an A2183T mutation, respectively, these nucleotide position and mutations being numbered by reference to SEQ ID NO:2.

In another embodiment of the instant invention, intron excision from the modified HCV coding sequence is sufficiently reduced such that greater than 70% of the glycoprotein is full length. In a further embodiment, intron excision from the modified HCV coding sequence is sufficiently reduced such that greater than 90% of the glycoprotein is full length.

This invention still further provides a cell expressing on a surface thereof a hepatitis C virus (HCV) glycoprotein selected from the group consisting of E1 glycoprotein and E1/E2 glycoprotein heterodimer, wherein the glycoprotein is expressed from a modified HCV coding sequence according to any of the methods described herein.

This invention additionally provides a cell-surface-localized hepatitis C virus (HCV) glycoprotein, selected from the group consisting of E1 glycoprotein and E1/E2 glycoprotein heterodimer, wherein the glycoprotein is expressed from a modified HCV coding sequence according to any of the methods described herein.

This invention further provides a method for making a pseudovirion expressing on a surface thereof a hepatitis C virus (HCV) glycoprotein selected from the group consisting of E1 glycoprotein and E1/E2 glycoprotein heterodimer, wherein the majority of the glycoprotein is full length, which method comprises (a) co-transfecting a cell with (1) at least one vector which provides virion packaging functions and expresses a reporter gene, and (2) a vector construct comprising a modified HCV coding sequence, selected from the group consisting of E1 and E1-E2 coding sequences, wherein at least one nucleotide alteration in the coding sequence eliminates at least one RNA splice site selected from the group consisting of RNA splice acceptor and RNA splice donor sites from the modified HCV coding sequence so as to reduce the extent of excision of an intron from the modified coding sequence; and (b) collecting viral supernatant containing pseudovirions.

In one embodiment of this method, intron excision from the modified HCV coding sequence is sufficiently reduced such that greater than 70% of the glycoprotein is full length. In another embodiment, intron excision from the modified HCV coding sequence is sufficiently reduced such that greater than 90% of the glycoprotein is full length.

In one embodiment, the packaging vector is preferably a retroviral packaging vector such as one of the vectors described in PCT International Publication No. WO 2004/024904. In a further embodiment, the at least one vector which provides virion packaging functions and expresses a reporter gene is derived from human immunodeficiency virus type 1 (HIV-1). In a still further embodiment, a single packaging vector provides virion packaging functions and expresses a reporter gene. In yet another embodiment, the packaging vector expresses a luciferase, a green fluorescent protein, a yellow fluorescent protein or a beta-galactosidase reporter gene. In a preferred embodiment, the packaging vector is pNL4.3-Luc+env-, wherein pNL4.3-Luc+env- expresses a luciferase reporter gene.

In an additional embodiment, the at least one vector which provides virion packaging functions and expresses a reporter gene is derived from human T-cell leukemia virus type 1 (HTLV-1). In another embodiment, a packaging vector provides virion packaging functions and a separate transfer vector expresses a reporter gene. In yet another embodiment, the transfer vector expresses a luciferase, a green fluorescent protein, a yellow fluorescent protein or a beta-galactosidase reporter gene. In a preferred embodiment, the packaging vector is pCMV-HT1 or PCMV-HT-Δenv. In another preferred embodiment, the transfer vector is pHTC-luc, pHTC-luc-tsa, pHTC-eYFP or pHTC-eYFP-tsa.

In another embodiment, the at least one vector which provides virion packaging functions and expresses a reporter gene is derived from an avian C-type retrovirus. In a preferred embodiment, the packaging vector is pRD136. In another preferred embodiment, the transfer vector is pCXL.

In a further embodiment, the cell is a 293T cell.

This invention also provides a pseudovirion expressing on its surface a hepatitis C virus (HCV) glycoprotein, selected from the group consisting of E1 glycoprotein and E1/E2 glycoprotein heterodimer, wherein the majority of the glycoprotein is full length. In one embodiment, greater than 70% of the glycoprotein is full length. In another embodiment, greater than 90% of the glycoprotein is full length.

This invention additionally provides an immunogen comprising any one of the hepatitis C virus (HCV) pseudovirions described herein.

The present invention also provides a pharmaceutical composition comprising any one of the hepatitis C virus (HCV) pseudovirions described herein and a pharmaceutically acceptable carrier. In one embodiment, this pharmaceutical composition further comprises an adjuvant.

The pseudovirion of the present invention may be used to produce antibodies useful for binding to HCV or producing a protective immune response in humans. Anti-HCV antibodies useful for diagnostic kits to detect HCV in human tissues can also be readily produced in animals such as a mouse, rat, rabbit, goat, sheep or horse using well known techniques. It will be understood that human antibodies that bind to pseudovirion can be similarly raised by immunizing a human patient or volunteer.

Accordingly, this invention provides a method for producing a polyclonal antibody that specifically binds to hepatitis C virus (HCV) comprising: (a) injecting into a subject an immunogen comprising an HCV pseudovirion to induce a primary immune response in said subject; (b) administering at least one booster injection of pseudovirion to the subject; and (c) purifying from the subject's serum a polyclonal antibody that binds specifically to HCV.

Pseudovirion are used to immunize the subject generally using a procedure where about 10 to 100 μg, preferably about 50 μg, of the particles are initially administered to the animal to induce a primary immune response followed by one to about five booster injections of about 10 to 100 μg of pseudovirion over a period of about two weeks to twelve months. Depending on the size of the animal to which the pseudovirion are administered, the dosage may vary, as may be readily determined by those skilled in the art. The timing and dosage of the booster injections in particular are determined based on the immune response detected in the animal, using methods well known to those skilled in the art. The pseudovirion are preferably administered subcutaneously as a suspension that includes an adjuvant such as Freund's complete or incomplete adjuvant, although a wide variety of available adjuvants are also suitable. Polyclonal antibodies induced after the primary response to pseudovirion are generally IgM whereas those produced following booster injections are generally IgG, generally reaching levels of 1 to 10 mg/ml of serum.

This invention also provides a polyclonal antibody that specifically binds to HCV. In one embodiment, the antibody neutralizes HCV. In another embodiment, the antibody inhibits HCV fusion with and entry into a target cell. In a further embodiment, the antibody inhibits transinfection. In a still further embodiment, the antibody binds to E1, E2 or E1/E2 and reduces viral load in a cell infected with HCV. In yet another embodiment, the antibody binds to E1, E2 or E1/E2 expressed from any of the modified nucleic acids described herein.

Methods for producing monoclonal antibodies are well known in the art (see, e.g., Kohler and Milstein, 1975). This invention further provides a method for producing a monoclonal antibody that specifically binds to hepatitis C virus (HCV) comprising: (a) injecting into a subject an immunogen comprising an HCV pseudovirion to induce a primary immune response in the subject; (b) administering at least one booster injection of pseudovirion to the subject; (c) harvesting antibody-producing lymphatic cells from the subject; (d) generating hybridomas by fusing single antibody-producing cells obtained in (c) with myeloma cells; and (e) screening hybridoma supernatants from these hybridomas to identify at least one monoclonal antibody that specifically binds to HCV.

This invention still further provides a monoclonal antibody that specifically binds to HCV. In one embodiment, the antibody neutralizes HCV. In another embodiment, the antibody inhibits HCV fusion with and entry into a target cell. In a further embodiment, the antibody inhibits transinfection. In a still further embodiment, the antibody binds to E1, E2 or E1/E2 and reduces viral load in a cell infected with HCV. In yet another embodiment, the antibody binds to E1, E2 or E1/E2 expressed from any of the modified nucleic acids described herein.

In one embodiment, the antibody is humanized. In a further embodiment, the antibody is a human antibody.

In one embodiment of the humanized form of the antibody, some, most or all of the amino acids outside the CDR regions have been replaced with amino acids from human immunoglobulin molecules whereas some, most or all amino acids within one or more CDR regions are unchanged. Small additions, deletions, insertions, substitutions or modifications of amino acids are permissible as long as they do not abrogate the ability of the antibody to bind a given antigen. Suitable human immunoglobulin molecules include IgG1, IgG2, IgG3, IgG4, IgA and IgM molecules. A humanized antibody retains a similar antigenic specificity as the original antibody, i.e., in the present invention, the ability to bind to HCV, inhibit fusion of HCV to or entry into cells so as to inhibit or prevent infection of these cells.

One skilled in the art would know how to make the humanized antibodies of the subject invention. Various publications, several of which are hereby incorporated by reference into this application- also describe how to make humanized antibodies. For example, the methods described in U.S. Pat. No. 4,816,567 enable the production of chimeric antibodies having a variable region of one antibody and a constant region of another antibody. U.S. Pat. No. 5,225,539 describes another approach for the production of a humanized antibody. In this approach, recombinant DNA technology is used to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. Nos. 5,585,089 and 5,693,761 and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

The variable regions of the humanized antibody may be linked to at least a portion of an immunoglobulin constant region of a human immunoglobulin. In one embodiment, the humanized antibody contains both light chain and heavy chain constant regions. The heavy chain constant region usually includes CH1, hinge, CH2, CH3 and sometimes, CH4 region.

Fully human monoclonal antibodies also can be prepared by immunizing mice transgenic for large portions of human immunoglobulin heavy and light chain loci (see, e.g., U.S. Pat. Nos. 5,591,669; 5,598,369; 5,545,806; 5,545,807; 6,150,584 and references cited therein, the contents of which are incorporated herein by reference). These animals have been genetically modified such that there is a functional deletion in the production of endogenous (e.g., murine) antibodies. These animals are further modified to contain all or a portion of the human germ-line immunoglobulin gene locus such that immunization of these animals results in the production of fully human antibodies. Following immunization of these mice (e.g., XenoMouse®, Abgenix, Fremont, Calif.; HuMab-Mouse®, Medarex/GenPharm, Princeton, N.J.), monoclonal antibodies are prepared according to standard hybridoma technology (e.g., Kohler and Milstein, 1975).

This invention additionally provides a nucleic acid molecule encoding a monoclonal antibody or fragment thereof that specifically binds to HCV. In one embodiment, the encoded monoclonal antibody or fragment thereof is humanized. In another embodiment, the encoded monoclonal antibody or fragment thereof is fully human.

The nucleic acid molecule can be RNA, DNA or cDNA. In one embodiment, the nucleic acid molecule encodes the light chain. In another embodiment, the nucleic acid molecule encodes the heavy chain. In a further embodiment, the nucleic acid encodes both the heavy and light chains. In a still further embodiment, one or more nucleic acid molecules encode the Fab portion. In an additional embodiment, one or more nucleic acid molecules encode CDR portions. In another embodiment, the nucleic acid molecule encodes the variable domain. In a further embodiment, the nucleic acid molecule encodes the variable domain and one or more constant domains.

In addition, this invention provides a method for expressing in a cell a modified hepatitis C virus (HCV) glycoprotein selected from the group consisting of modified E1 glycoprotein and modified E1/E2 glycoprotein heterodimer, wherein the glycoprotein produced is homogeneously truncated by a deletion of amino acid residues 226 to 296 inclusive, these amino acid residues being numbered by reference to SEQ ID NO:3, which method comprises transfecting a cell with an expression vector comprising a modified coding sequence, wherein a nucleotide sequence corresponding to a putative intron between nucleotide positions 675 and 887 inclusive is deleted, these nucleotide positions being numbered by reference to SEQ ID NO:2, under conditions suitable for expression of vector-encoded glycoprotein, so as to express a homogeneously truncated glycoprotein lacking amino acid residues 226 to 296 inclusive, these amino acid residues being numbered by reference to SEQ ID NO:3.

This invention also provides a modified hepatitis C virus (HCV) glycoprotein, selected from the group consisting of modified E1 glycoprotein and modified E1/E2 glycoprotein heterodimer, wherein the modified glycoprotein is homogeneously truncated by a deletion of amino acid residues 226 to 296 inclusive, these amino acid residues being numbered by reference to SEQ ID NO:3.

This invention further provides a method for determining Whether an agent inhibits fusion of hepatitis C virus (HCV) to a target cell capable of fusing with HCV, which method comprises (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of an agent under conditions which would normally permit fusion of the target cell to the cell expressing HCV E1/E2 glycoprotein dimer on its surface in the absence of the agent, wherein the first and second dyes are selected so as to allow resonance energy transfer between the dyes; (b) exposing the contacted cells to conditions which would result in resonance energy transfer if fusion has occurred; and (c) determining whether there is a reduction of resonance energy transfer in the presence of the agent compared with the resonance energy transfer in the absence of the agent; wherein a reduction in resonance energy transfer in the presence of the agent indicates that the agent inhibits fusion of HCV to the target cell. In one embodiment of the instant method, the agent is not previously known to inhibit fusion of HCV to the target cell.

This invention still further provides a method for screening a plurality of agents, not known to inhibit fusion of hepatitis C virus (HCV) to a target cell capable of fusing with this virus, to identify at least one agent that inhibits such fusion, which method comprises (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of a plurality of agents under conditions which would normally permit fusion of the target cell to the cell expressing HCV E1/E2 glycoprotein dimer on its surface in the absence of the plurality of agents, wherein the first and second dyes are selected so as to allow resonance energy transfer between the dyes; (b) exposing the contacted cells to conditions which would result in resonance energy transfer if fusion has occurred; (c) determining whether there is a reduction of resonance energy transfer in the presence of the plurality of agents compared with the resonance energy transfer in the absence of the plurality of agents; and (d) if the resonance energy transfer is reduced in the presence of the plurality of agents, separately determining which of the agents present in the plurality of agents causes a reduction in resonance energy transfer, so as to thereby identify at least one agent that inhibits fusion of HCV to a target cell.

In one embodiment of the above methods, the agent is added to the cell expressing HCV E1/E2 glycoprotein heterodimer on its surface, the target cell, or both the target cell and the cell expressing HCV E1/E2 glycoprotein heterodimer on its surface. In another embodiment, the target cell is a liver cell selected from the group consisting of Huh-7, PLC/PRF/5, Hep 3B, HepG2, Caco-2, HT1080, HT-29, LoVo, MCF-7, U118, 293T, and Vero cells. In a further embodiment, the target cell is a fresh or cryopreserved human hepatocyte, isolated from an adult human liver biopsy. In another embodiment, the first dye is a rhodamine moiety-containing molecule and the second dye is a fluorescein moiety-containing molecule. In a further embodiment, the rhodamine moiety-containing molecule is octadecyl rhodamine B chloride and the fluorescein moiety-containing molecule is fluorescein octadecyl ester. In a still further embodiment, the first dye is a fluorescein moiety-containing molecule and the second dye is a rhodamine moiety-containing molecule. In yet another embodiment, the rhodamine moiety-containing molecule is octadecyl rhodamine B chloride and the fluorescein moiety-containing molecule is fluorescein octadecyl ester.

The present invention additionally provides an agent that inhibits fusion of hepatitis C virus (HCV) to a target cell capable of fusing with HCV. In one embodiment, the agent is an antibody or fragment thereof. In another embodiment, the antibody is a monoclonal antibody. In yet another embodiment, the antibody is a polyclonal antibody. In a further embodiment, the antibody is a humanized antibody or fragment thereof. In a still further embodiment, the antibody is a human antibody or fragment thereof. In one embodiment, the fragment of the antibody comprises a light chain of an antibody. In another embodiment, the fragment of the antibody comprises a heavy chain of an antibody. In yet another embodiment, the fragment of the antibody comprises an Fab fragment of an antibody. In a further embodiment, the fragment of the antibody comprises an $F(ab')_2$ fragment of an antibody. In a still further embodiment, the fragment of the antibody comprises an Fd fragment of an antibody. In one embodiment, the fragment of the antibody comprises an Fv fragment of an antibody. In another embodiment, the fragment of the antibody comprises a variable domain of an antibody. In a further embodiment, the fragment of the antibody comprises one or more CDR domains of an antibody.

In another embodiment, the agent is a peptide. In yet another embodiment, the agent comprises a peptide bond. In a further embodiment, the agent is a non-peptidyl agent. In a still further embodiment, the agent is a small molecule or a low molecular weight molecule. In another embodiment, the molecule has a molecular weight less than 500 daltons.

The designing and synthesizing of chemical agents described herein that bind to surface components of HCV or a cell and inhibit fusion of HCV with the cell membrane or inhibit HCV entry into the cell may be facilitated by experimental approaches that are well known in the art, including traditional medicinal chemistry and the newer technology of combinatorial chemistry, both of which may be supported by computer-assisted molecular modeling. With such approaches, chemists and pharmacologists use their knowledge of the structures of surface molecules, e.g., the E1/E2 glycoprotein heterodimer, and agents determined to bind such molecules to design and synthesize a variety of additional agents that will bind to the surface molecules.

Combinatorial chemistry involves automated synthesis of a variety of novel agents by assembling them using different combinations of chemical building blocks. The use of this technique greatly accelerates the process of generating agents. The resulting arrays of agents are called libraries and are used to screen for agents ("lead agents") that demonstrate a sufficient level of binding at molecules of interest. Using combinatorial chemistry it is possible to synthesize "focused" libraries of agents anticipated to be highly biased toward the target molecule.

Once lead agents are identified, whether through the use of combinatorial chemistry or traditional medicinal chemistry or otherwise, a variety of homologs and analogs are prepared to facilitate an understanding of the relationship between chemical structure, binding affinity for the target molecule, and biological or functional activity, which in the methods described herein is the ability of an agent to inhibit the fusion of HCV to a target cell or inhibit HCV entry into the cell. These studies define structure activity relationships (SARs) which are then used to design drugs with improved potency, selectivity and pharmacokinetic properties. Combinatorial chemistry is also used to rapidly generate a variety of structures for lead optimization. Traditional medicinal chemistry, which involves the synthesis of agents one at a time, is also used for further refinement and to generate agents not synthesizable by automated techniques. Once such drugs are defined, production is scaled up using standard chemical manufacturing methodologies utilized throughout the pharmaceutical and chemical industries.

Numerous non-peptidyl small molecules are available from a variety of commercial sources for screening for agents having desired functional properties. For example, ChemDiv (San Diego, Calif.) has an International Diversity collection of small molecules comprising over 150,000 small molecules selected from more than 3,500,000 chemical agents, and a CombiLab set of over 2,000 libraries of "probe" agents. Each library is represented by the validated template, a set of corresponding building blocks, substituents for SAR synthesis, the off-shelf probe compound set and complete synthetic protocol. Every template is prone.

The total feasible chemistry space of CombiLab's libraries is over 10,000,000,000 structures, with 250,000 of these being represented by probe sets. The major emphases of these libraries are on chemical novelty, drug- and lead-likeness, particular protein families identified as potential therapeutic target, favorable predicted absorption, distribution, metabolism, and excretion (ADME) and toxicity properties, and synthetic feasibility and cost. All compounds are produced in >150 mg quantities by liquid-phase parallel synthesis and individually purified to meet a >90% purity threshold. Every final compound and all key intermediates are analyzed by LC-MS or NMR at 400 Mhz.

ChemDiv has a large number of small molecules that are usable as building blocks for identifying and optimizing the chemical structures of agents in the screening methods described herein. The following are examples of building block molecules available for custom synthesis:

S00503

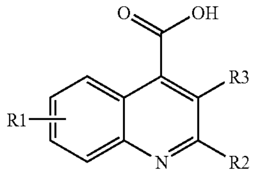

S00501

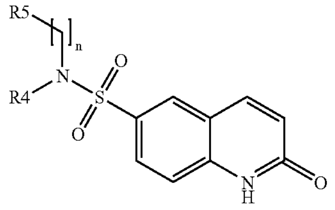

S00504

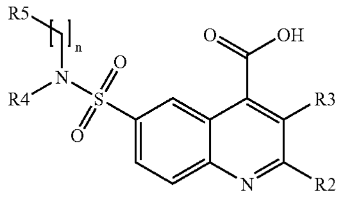

S00507

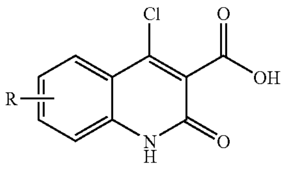

-continued

S00508

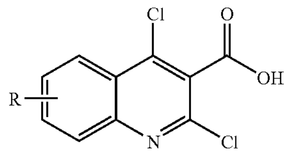

S00501, S00503, S00504: R1=H, $CH_3$, Cl, $CF_3$, and other; R2=alkyl, aryl, hetaryl, and other; R2+R3=$(CH_2)_m$; R4, R5=H, alkyl, aryl, heterocyclyl, and other; m=0, 1-4; n=1-3.

S00507, S00508: R═H, alkyl, alkoxy, Cl and other.

The library of building blocks contains scaffolds with several reaction centers, of which the following are examples:

S00104

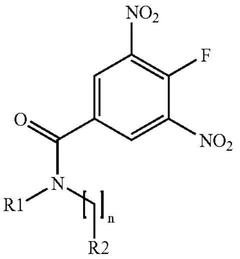

S00105

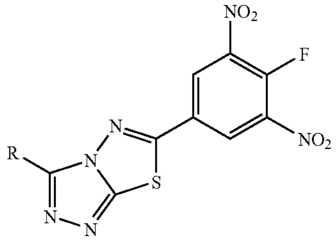

S00106

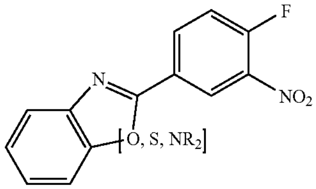

R052-0857

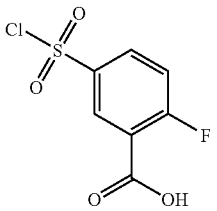

R052-0859

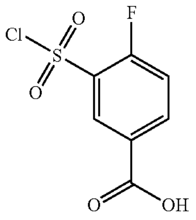

-continued

R052-0856

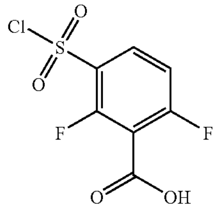

S00104: R1, R2=H, alkyl, aryl, heterocyclyl, and other; n=0, 1-5; R1—N—$(CH_2)_n$—R2=heterocycle.

S00105: R═H, alkyloxyalkyl, alkylthioalkyl, aryl, heterocyclyl, and other.

S00106: R═H, alkyl, alkyloxy, F, Cl, and other.

R052-0733

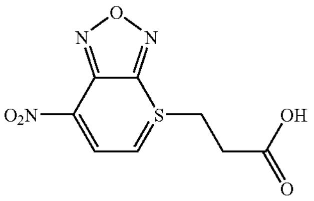

R052-0675

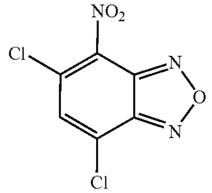

R052-0343

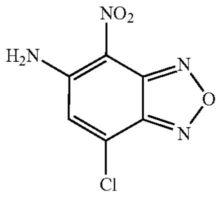

R052-1644

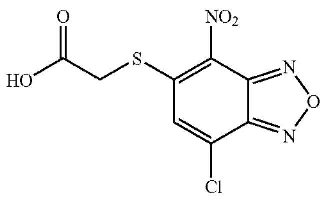

R052-0647

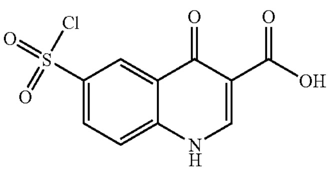

Each of these scaffolds may be used for generating a series of different combinatorial libraries. For example, the scheme below depicts some agents belonging to various combinatorial libraries, which can be produced with the scaffolds containing the fluoronitrobenzene moiety.

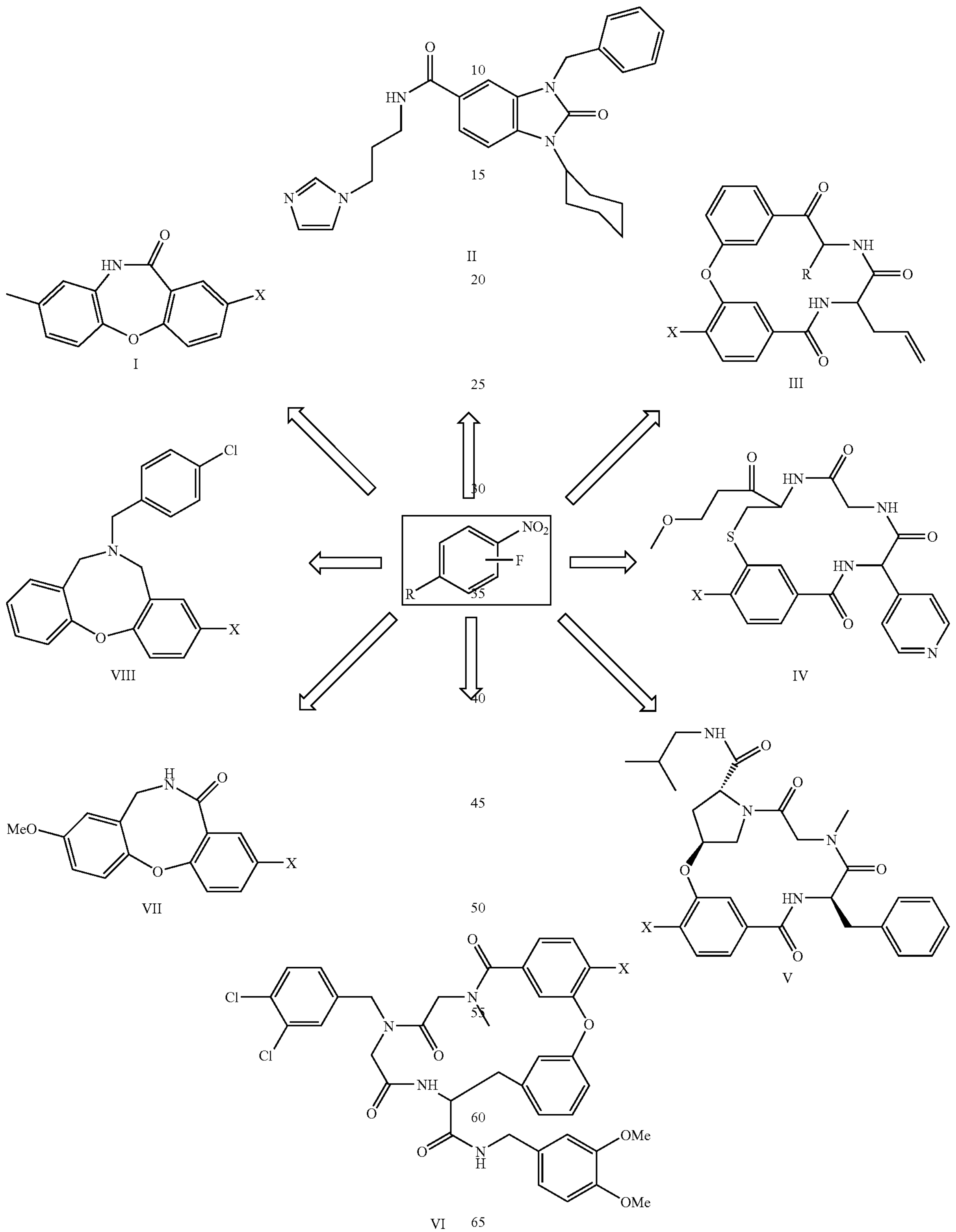
I
II
III
IV
V
VI
VII
VIII

Compound I is described by Ouyang et al. (1999a), VII by Ouyang et al. (1999b) and VIII by Ouyang et al. (1999c). Compound II is described by Wei et al. (1998). Compounds III is described by Kiselyov et al. (1999a); IV by Kiselyov et al. (1998) and VI by Kiselyov et al. (1999b). Compound V is described by Goldberg et al. (1999).

Libraries of nonpeptidyl small molecule agents for use in the present invention are also commercially available from Chembridge Collections (ChemBridge Corp., San Diego, Calif.). One ChemBridge library, PHARMACOphore diverse combination library, has over 60,000 compounds comprising multiple, chemically diverse libraries/templates. The average number of compounds per library/template is less than 2,000 with multiple chemical motifs inside each individual library. Another library available from ChemBridge includes DIVERSet which contains 50,000 compounds.

This invention also provides a pharmaceutical composition comprising any of the agents described herein and a pharmaceutically acceptable carrier. In one embodiment, the pharmaceutical composition further comprises at least one conventional antiviral agent. In a further embodiment, the antiviral agent includes but is not limited to the group consisting of interferon-alpha, interferon-alpha-2B and ribavirin.

Pharmaceutically acceptable carriers are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. In addition to carriers described above, a vaccine may further include carriers known in the art such as, for example, thyroglobulin, albumin, tetanus toxoid, polyamino acids such as polymers of D-lysine and D-glutamate, inactivated influenza virus and hepatitis B recombinant protein(s). The vaccine may also include any well known adjuvants such as incomplete Freund's adjuvant, alum, aluminum phosphate, aluminum hydroxide, monophosphoryl lipid A (MPL, GlaxoSmithKline), saponins including QS21 (GlaxoSmithKline), CpG oligonucleotides (Krieg et al., 1995), montanide, vitamin E and various water-in-oil emulsions prepared from biodegradable oils such as squalene and/or tocopherol, Quil A, Ribi Detox, CRL-1005, L-121 and combinations thereof. Preservatives and other additives, such as, for example, antimicrobials, antioxidants, chelating agents, inert gases, and the like may also be included with all the above carriers.

This invention further provides a method for determining whether an agent inhibits entry of hepatitis C virus (HCV) into a target cell susceptible to infection by HCV, comprising (a) separately contacting (1) a pseudovirion expressing HCV E1/E2 glycoprotein heterodimer on its surface, wherein a majority of the E1/E2 glycoprotein is full length, which pseudovirion was produced using at least one vector which provides virion packaging functions and expresses a reporter gene, with (2) a target cell in the presence and absence of an agent under conditions which would normally permit entry of the pseudovirion into the target cell in the absence of the agent; and (b) lysing the contacted target cell and determining whether there is a reduction in reporter gene activity in the presence of the agent compared with reporter gene activity in the absence of the agent; wherein a reduction in reporter gene activity in the presence of the agent indicates that the agent inhibits entry of HCV into the target cell. In one embodiment of the instant method, the agent is not previously known to inhibit entry of HCV into the target cell.

This invention still further provides a method for screening a plurality of agents, not known to inhibit entry of hepatitis C virus (HCV) into a target cell susceptible to infection by HCV, to identify at least one agent that inhibits such entry, which method comprises (a) separately contacting (1) a pseudovirion expressing HCV E1/E2 glycoprotein heterodimer on its surface, wherein a majority of the E1/E2 glycoprotein is full length, which pseudovirion was produced using at least one vector which provides virion packaging functions and expresses a reporter gene, with (2) a target cell in the presence and absence of a plurality of agents under conditions which would normally permit entry of the pseudovirion into the target cell in the absence of the plurality of agents; (b) lysing the contacted target cell and determining whether there is a reduction in reporter gene activity in the presence of the plurality of agents compared with the reporter gene activity in the absence of the plurality of agents; and (c) if the reporter gene activity is reduced in the presence of the plurality of agents, separately determining which of the agents present in the plurality of agents causes a reduction in reporter gene activity, so as to thereby identify at least one agent that inhibits entry of HCV into a target cell.

In one embodiment of the above methods, the agent is added to the target cell, the pseudovirion or both the target cell and the pseudovirion. In another embodiment, the agent is added after the target cell is contacted with the pseudovirion but prior to viral entry. In a further embodiment, the target cell is selected from a group of liver cells consisting of Huh-7, PLC/PRF/5, Hep 3B, HepG2, Caco-2, HT1080, HT-29, LoVo, MCF-7, U118, 293T, and Vero cells. In another embodiment, the target cell is a fresh or cryopreserved human hepatocyte, isolated from an adult human liver biopsy.

In one embodiment, the packaging vector is preferably a retroviral packaging vector such as one of the vectors described in PCT International Publication No. WO 2004/024904. In a further embodiment, the at least one vector which provides virion packaging functions and expresses a reporter gene is derived from human immunodeficiency virus type 1 (HIV-1). In a still further embodiment, a single packaging vector provides virion packaging functions and expresses a reporter gene.

In one embodiment, the packaging vector expresses a luciferase, a green fluorescent protein, a yellow fluorescent protein or a beta-galactosidase reporter gene.

In a preferred embodiment, the packaging vector is pNL4.3-Luc+env-, wherein pNL4.3-Luc+env- expresses a luciferase reporter gene.

In another embodiment, the at least one vector which provides virion packaging functions and expresses a reporter gene is derived from human T-cell leukemia virus type 1 (HTLV-1). In a further embodiment, a packaging vector provides virion packaging functions and a separate transfer vector expresses a reporter gene. In yet another embodiment, the transfer vector expresses a luciferase, a green fluorescent protein, a yellow fluorescent protein or a beta-galactosidase reporter gene. In a preferred embodiment, the packaging vector is pCMV-HT1 or PCMV-HT-Δenv. In another preferred embodiment, the transfer vector is pHTC-luc, pHTC-luc-tsa, pHTC-eYFP or pHTC-eYFP-tsa.

In an additional embodiment, the at least one vector which provides virion packaging functions and expresses a reporter gene is derived from an avian C-type retrovirus. In a preferred embodiment, the packaging vector is pRD136. In another preferred embodiment, the transfer vector is pCXL.

Additionally, this invention provides an agent that inhibits entry of hepatitis C virus (HCV) into a target cell susceptible to infection by HCV. In one embodiment, the agent is an antibody or fragment thereof. In another embodiment, the antibody is a monoclonal antibody. In yet another embodiment, the antibody is a polyclonal antibody. In a further embodiment, the antibody is a humanized antibody or fragment thereof. In a still further embodiment, the antibody is a human antibody or fragment thereof. In one embodiment, the fragment of the antibody comprises a light chain of an antibody. In another embodiment, the fragment of the antibody comprises a heavy chain of an antibody. In yet another embodiment, the fragment of the antibody comprises an Fab fragment of an antibody. In a further embodiment, the fragment of the antibody comprises an $F(ab')_2$ fragment of an antibody. In a still further embodiment, the fragment of the antibody comprises an Fd fragment of an antibody. In one embodiment, the fragment of the antibody comprises an Fv fragment of an antibody. In another embodiment, the fragment of the antibody comprises a variable domain of an antibody. In a further embodiment, the fragment of the antibody comprises one or more CDR domains of an antibody.

In another embodiment, the agent is a peptide. In yet another embodiment, the agent comprises a peptide bond. In a further embodiment, the agent is a non-peptidyl agent. In a still further embodiment, the agent is a small molecule or a low molecular weight molecule. In another embodiment, the molecule has a molecular weight less than 500 daltons.

This invention also provides a pharmaceutical composition comprising any of the agents described herein and a pharmaceutically acceptable carrier. In one embodiment, the pharmaceutical composition further comprises at least one conventional antiviral agent. In a further embodiment, the antiviral agent includes but is not limited to the group consisting of interferon-alpha, interferon-alpha-2B and ribavirin.

In various methods described herein, agents identified to inhibit HCV fusion with or entry into target cells are used in therapeutically or prophylactically effective amounts respectively to treat a subject afflicted with a pathogen-related disorder or to inhibit the onset of such a disorder. Specifically, the present invention provides a method for treating a subject afflicted with a hepatitis C virus (HCV)-associated disorder, which treatment is effected by inhibiting fusion of HCV to a target cell capable of fusing with this virus, which method comprises administering to the subject an agent, wherein this agent is (1) determined to inhibit fusion of HCV to a target cell capable of fusing with HCV using a method comprising (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of the agent under conditions which would normally permit fusion of the target cell to the cell expressing HCV E1/E2 glycoprotein dimer on its surface in the absence of the agent, wherein the first and second dyes are selected so as to allow resonance energy transfer between the dyes; (b) exposing the contacted cells to conditions which would result in resonance energy transfer if fusion has occurred; and (c) determining whether there is a reduction of resonance energy transfer in the presence of the agent compared with the resonance energy transfer in the absence of the agent; wherein a reduction in resonance energy transfer in the presence of the agent indicates that the agent inhibits fusion of HCV to the target cell, and (2) administered in a therapeutically effective amount to treat the subject.

This invention also provides a method for treating a subject afflicted with a hepatitis C virus (HCV)-associated disorder, which treatment is effected by inhibiting entry of HCV into a target cell susceptible to infection by this virus, which method comprises administering to the subject an agent, wherein this agent is (1) determined to inhibit entry of HCV into a target cell using a method comprising: (a) separately contacting a pseudovirion expressing HCV E1/E2 glycoprotein heterodimer on its surface, wherein the majority of the E1/E2 glycoprotein is full length, which pseudovirion was produced using a packaging vector that expresses a reporter gene, with a target cell in the presence and absence of the agent under conditions which would normally permit entry of the pseudovirion into the target cell in the absence of the agent; and (b) lysing the contacted target cell and determining whether there is a reduction in reporter gene activity in the presence of the agent compared with the reporter gene activity in the absence of the agent; wherein a reduction in reporter gene activity in the presence of the agent indicates that the agent inhibits entry of HCV into the target cell; and (2) administered in a therapeutically effective amount to treat the subject.

This invention further provides a method for preventing a hepatitis C virus (HCV) infection in a subject, the prevention of which is effected by inhibiting fusion of HCV to a target cell capable of fusing with this virus, which method comprises administering to the subject an agent, wherein this agent is (1) determined to inhibit fusion of HCV to a target cell capable of fusing with HCV using a method comprising: (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of the agent under conditions which would normally permit fusion of the target cell to the cell expressing HCV E1/E2 glycoprotein dimer on its surface in the absence of the agent, wherein the first and second dyes are selected so as to allow resonance energy transfer between the dyes; (b) exposing the contacted cells to conditions which would result in resonance energy transfer if fusion has occurred; and (c) determining whether there is a reduction of resonance energy transfer in the presence of the agent compared with the resonance energy transfer in the absence of the agent; wherein a reduction in resonance energy transfer in the presence of the agent indicates that the agent inhibits fusion of HCV to the target cell; and (2) administered in a prophylactically effective amount to prevent an HCV infection in the subject.

This invention still further provides a method for inhibiting in a subject the onset of a hepatitis C virus (HCV)-associated disorder, the inhibition of which is effected by inhibiting fusion of HCV to a target cell capable of fusing with this virus, which method comprises administering to the subject an agent, wherein this agent is (1) determined to inhibit fusion of HCV to a target cell capable of fusing with HCV using a method comprising (a) separately contacting a target cell, which is labeled with a first dye, with a cell expressing HCV E1/E2 glycoprotein heterodimer on its surface, which HCV glycoprotein-expressing cell is labeled with a second dye, in the presence and absence of the agent under conditions which would normally permit fusion of the target cell to the cell expressing HCV E1/E2 glycoprotein dimer on its surface in the absence of the agent, wherein the first and second dyes are selected so as to allow resonance energy transfer between the dyes; (b) exposing the contacted cells to conditions which would result in resonance energy transfer if fusion has occurred; and (c) determining whether there is a reduction of resonance energy transfer in the presence of the agent compared with the resonance energy transfer in the absence of the agent; wherein a reduction in resonance energy transfer in the presence of the agent indicates that the agent inhibits fusion of HCV to the target cell; and (2) administered in a prophylactically effective amount to have a prophylactic effect in the subject.

This invention additionally provides a method for preventing a hepatitis C virus (HCV) infection in a subject, the prevention of which is effected by inhibiting entry of HCV into a target cell susceptible to infection by this virus, which method comprises administering to the subject an agent, wherein this agent is (1) determined to inhibit entry of HCV into a target cell using a method comprising: (a) separately contacting a pseudovirion expressing HCV E1/E2 glycoprotein heterodimer on its surface, wherein the majority of the E1/E2 glycoprotein is full length, which pseudovirion was produced using a packaging vector that expresses a reporter gene, with a target cell in the presence and absence of the agent under conditions which would normally permit entry of the pseudovirion into the target cell in the absence of the agent; and (b) lysing the contacted target cell and determining whether there is a reduction in reporter gene activity in the presence of the agent compared with the reporter gene activity in the absence of the agent; wherein a reduction in reporter gene activity in the presence of the agent indicates that the agent inhibits entry of HCV into the target cell; and (2) administered in a prophylactically effective amount to prevent an HCV infection in the subject.

This invention also provides a method for inhibiting in a subject the onset of a hepatitis C virus (HCV)-associated disorder, the inhibition of which is effected by inhibiting entry of HCV into a target cell susceptible to infection by this virus, which method comprises administering to the subject an agent, wherein this agent is (1) determined to inhibit entry of HCV into a target cell using a method comprising: (a) separately contacting a pseudovirion expressing HCV E1/E2 glycoprotein heterodimer on its surface, wherein the majority of the E1/E2 glycoprotein is full length, which pseudovirion was produced using a packaging vector that expresses a reporter gene, with a target cell in the presence and absence of the agent under conditions which would normally permit entry of the pseudovirion into the target cell in the absence of the agent; and (b) lysing the contacted target cell and determining whether there is a reduction in reporter gene activity in the presence of the agent compared with the reporter gene activity in the absence of the agent; wherein a reduction in reporter gene activity in the presence of the agent indicates that the agent inhibits entry of HCV into the target cell; and (2) administered in a prophylactically effective amount to have a prophylactic effect in the subject.

Determining a therapeutically or prophylactically effective amount of the agents and compositions described herein can be done based on animal data using routine computational methods. The effective amount is based upon, among other things, the size, form, biodegradability, bioactivity and bioavailability of the agent. By way of illustration, if the agent does not degrade quickly, is bioavailable and highly active, a smaller amount will be required to be effective.

In one embodiment of the instant method, the therapeutically or prophylactically effective amount contains between about 0.000001 mg/kg body weight and about 1000 mg/kg body weight of polypeptide or non-peptidyl agent. In another embodiment, the effective amount contains between about 0.0001 mg/kg body weight and about 250 mg/kg body weight of polypeptide or non-peptidyl agent. In a further embodiment, the effective amount contains between about 0.001 mg/kg body weight and about 50 mg/kg body weight of polypeptide or non-peptidyl agent. In a still further embodiment, the effective amount contains between about 0.01 mg/kg body weight and about 10 mg/kg body weight of polypeptide or non-peptidyl agent. In another embodiment, the effective amount contains between about 0.05 mg/kg body weight and about 2.5 mg/kg body weight of polypeptide or non-peptidyl agent. In yet another embodiment, the effective amount contains between about 0.1 mg/kg body weight and about 0.5 mg/kg body weight of polypeptide or non-peptidyl agent.

Embodiments of methods described above for treating a subject afflicted with a hepatitis C virus (HCV)-associated disorder and methods for inhibiting in a subject the onset of a hepatitis C virus (HCV)-associated disorder further comprise administration of at least one conventional antiviral agent. In further embodiments, the antiviral agent includes but is not limited to the group consisting of interferon-alpha, interferon-alpha-2B and ribavirin.

Treatment of hepatitis C virus (HCV) infection may also be accomplished using pharmaceutical compositions comprising pseudovirion. Suitable formulations for delivery of pseudovirion are found in Remington's Pharmaceutical Sciences (1985). These pharmaceutical compositions are suitable for use in a variety of drug delivery systems (se Langer, 1990). Pseudovirion in compositions are suitable for single administration or in a series of inoculations (e.g., an initial immunization followed by subsequent inoculations to boost the anti-HCV immune response). The pharmaceutical compositions are intended for parenteral, topical or oral administration. Parenteral administration is preferably by intravenous, subcutaneous, intradermal, intraperitoneal or intramuscular administration. Parenteral administration may be preferentially directed to the patient's liver such as by catheterization to hepatic arteries or into a bile duct. For parenteral administration, the compositions can include pseudovirion suspended in a suitable sterile carrier such as water, aqueous buffer, 0.4% saline solution, 0.3% glycine, hyaluronic acid or emulsions of nontoxic nonionic surfactants as is well known in the art. The compositions may further include substances to approximate physiological conditions such as buffering agents and wetting agents such as NaCl, KCl, $CaCl_2$, sodium acetate and sodium lactate. Aqueous suspensions of pseudovirion can be lyophilized for storage and can be suitably recombined with sterile water before administration. Solid compositions including pseudovirion in conventional nontoxic solid carriers may be used. For oral administration of solid compositions, the pseudovirion preferably comprise 10% to 95%, and more preferably 25% to 75% of the composition.

Pseudovirion, formulated with a nontoxic surfactant, a propellant and possibly other carriers well known in the art, can also be administered in an aerosol such as for pulmonary and/or intranasal delivery Pseudovirion can be used prophylactically as a vaccine to prevent HCV infection. Accordingly, this invention also provides a method for preventing a hepatitis C virus (HCV) infection in a subject, the prevention of which is effected by immunizing the subject, which method comprises: (a) injecting into the subject a pharmaceutical composition comprising an HCV pseudovirion expressing on its surface a hepatitis C virus (HCV) glycoprotein selected from the group consisting of E1 glycoprotein and E1/E2 glycoprotein heterodimer, wherein the majority of the glycoprotein is full length; and thereby (b) eliciting a protective HCV immune response in the subject.

This invention further provides a method for inhibiting in a subject the onset of a hepatitis C virus (HCV)-associated disorder, the inhibition of which is effected by immunizing the subject, which method comprises: (a) injecting into the subject a pharmaceutical compositions comprising an HCV pseudovirion; thereby (b) eliciting a protective immune response in the subject. One embodiment of the instant immunization methods further comprises injecting into the subject a hepatitis C virus (HCV) glycoprotein selected from the group consisting of E1 glycoprotein, E1/E2 glycoprotein heterodimer and immunogenic fragments thereof. In another embodiment, the methods further comprise injecting into the subject a nucleic acid vector capable of expressing an HCV glycoprotein selected from the group consisting of E1 glycoprotein, E1/E2 glycoprotein heterodimer and immunogenic fragments thereof. In an additional embodiment, the methods further comprise administration of at least one conventional antiviral agent. In yet another embodiment, the antiviral agent includes but is not limited to the group consisting of interferon-alpha, interferon-alpha-2B and ribavirin.

A vaccine containing pseudovirion contains an immunogenically effective amount of the particles admixed with a pharmaceutically acceptable carrier such as those described above. The vaccine may further include carriers known in the art such as, for example, thyroglobulin, albumin, tetanus toxoid, polyamino acids such as polymers of D-lysine and D-glutamate, inactivated influenza virus and hepatitis B recombinant protein(s). The vaccine may also include any well known adjuvants such as incomplete Freund's adjuvant, alum, aluminum phosphate, aluminum hydroxide, monophosphoryl lipid A (MPL, GlaxoSmithKline), saponins including QS21 (GlaxoSmithKline), CpG oligonucleotides. (Krieg et al., 1995), montanide, vitamin E and various water-in-oil emulsions prepared from biodegradable oils such as squalene and/or tocopherol, Quil A, Ribi Detox, CRL-1005, L-121 and combinations thereof. The immune response generated to the pseudovirion may include generation of anti-HCV antibodies and/or generation of a cellular immune response (e.g., activation of cytotoxic T lymphocytes or CTL).

A vaccine composition containing a HCV pseudovirion is administered to a patient in an immunogenically effective amount to elicit a protective immune response against HCV. The immunogenically effective amount will vary depending on the composition of the vaccine (e.g., whether or not it contains adjuvant), the manner of administration, the weight and general health of the patient and the judgment of the prescribing health care provider. For initial vaccination, the general range of pseudovirion in the administered vaccine is about 100 μg to about 1 μm per 70 kg patient; subsequent inoculations to boost the immune response include pseudovirion in the range of 100 μg to about 1 μm per 70 kg patient. Single or multiple boosting immunizations are administered over a period of about two weeks to about six months from the initial vaccination. The prescribing health care provider may determine the number and timing of booster immunizations based on well known immunization protocols and the individual patient's response to the immunizations (e.g., as monitored by assaying for anti-HCV antibodies).

For treatment of a patient infected with HCV, the amount of pseudovirion to be delivered will vary with the method of delivery, the number of administrations and the state of the person receiving the composition (e.g., age, weight, severity of HCV infection, active or chronic status of HCV infection and general health status). Before therapeutic administration, the patient will already have been diagnosed as HCV-infected and may or may not be symptomatic. Generally, a therapeutically effective amount of pseudovirion will be in the range of about 1 mg to about 10 gm per day, preferably about 50 mg to about 5 gm per day, and most preferably about 100 mg to 1 gm per day for a 70 kg patient. The pseudovirion may be administered as a prime and/or boost, alone or in various prime/boost combinations with E1 glycoprotein, E1/E2 glycoprotein dimer or immunogenic portions thereof, or nucleic acid molecules encoding such glycoproteins as described above.

This invention further provides a diagnostic kit comprising an antibody as described herein and instructions for using this antibody to detect hepatitis C virus (HCV) in human tissue. In one embodiment, the instructions describe use of the antibody for an immunoassay. In another embodiment, the antibody is immobilized on a solid support. In a further embodiment, the solid support is selected from the group consisting of polysaccharide polymers (see U.S. Pat. No. 3,642,852), filter paper, nitrocellulose membrane, polyethylene, polystyrene and polypropylene.

This invention also provides an article of manufacture comprising a packaging material containing therein a modified nucleic acid molecule as described herein and a label providing instructions for using this modified nucleic acid to express on a cell surface a hepatitis C virus (HCV) glycoprotein selected from the group consisting of E1 glycoprotein and E1/E2 glycoprotein heterodimer, wherein the majority of the expressed glycoprotein is full length.

This invention further provides an article of manufacture comprising a packaging material containing therein a modified nucleic acid molecule as described herein and a label providing instructions for using the modified nucleic acid to generate a pseudovirion expressing on its surface a hepatitis C virus (HCV) glycoprotein selected from the group consisting of E1 glycoprotein and E1/E2 glycoprotein heterodimer, wherein the majority of the expressed glycoprotein is full length.

This invention still further provides an article of manufacture comprising a packaging material containing therein a cell expressing on the cell surface a hepatitis C virus (HCV) glycoprotein selected from the group consisting of E1 glycoprotein and E1/E2 glycoprotein heterodimer, wherein the majority of the glycoprotein is full length, and a label providing instructions for using the cell to identify an agent that inhibits fusion of HCV to a target cell capable of fusing with this virus.

Additionally, this invention provides an article of manufacture comprising a packaging material containing therein a pseudovirion expressing on its surface a hepatitis C virus (HCV) glycoprotein selected from the group consisting of E1 glycoprotein and E1/E2 glycoprotein heterodimer, wherein the majority of the glycoprotein is full length, and a label providing instructions for using the pseudovirion to identify an agent that inhibits entry of HCV into a target cell susceptible to infection by this virus.

This invention also provides an article of manufacture comprising a packaging material containing therein an agent as described herein and a label providing instructions for using this agent to treat a subject afflicted with a hepatitis C virus (HCV)-associated disorder, treatment to which is effected by inhibiting fusion of HCV to a target cell capable of fusing with this virus.

This invention further provides an article of manufacture comprising a packaging material containing therein an agent as described herein and a label providing instructions for using this agent to treat a subject afflicted with a hepatitis C virus (HCV)-associated disorder, treatment to which is effected by inhibiting entry of HCV into a target cell susceptible to infection by this virus.

This invention still further provides an article of manufacture comprising a packaging material containing therein an agent as described herein and a label providing instructions for using this agent to inhibit in a subject the onset of a hepatitis C virus (HCV)-associated disorder, the inhibition of which is effected by inhibiting fusion of HCV to a target cell capable of fusing with this virus.

This invention also provides an article of manufacture comprising a packaging material containing therein an agent as described herein and a label providing instructions for using this agent to inhibit in a subject the onset of a hepatitis C virus (HCV)-associated disorder, the inhibition of which is effected by inhibiting entry of HCV into a target cell susceptible to infection by this virus.

EXPERIMENTAL DETAILS

The following Experimental Details are set forth to aid in an understanding of the invention, and are not intended, and should not be construed, to limit in any way the invention set forth in the claims which follow thereafter.

It should also be understood that the HCV isolates used as examples to provide nucleotide and amino acid sequences in the present invention are not intended to limit the scope of the invention, and that any HCV isolate from type 1, 2, 3, 4, 5, 6, 7, 8, 9, 10, 11 or any other new genotype of HCV is a suitable source of E1 and/or E2 sequence for the practice of the present invention. Analysis of the entire HCV sequence from any genotype of HCV by a splice site neural network (http://www.fruitfly.org/seq tools/splice.html) is used to identify the presence of a splice donor site and/or splice acceptor site, and conservative mutagenesis is performed to generate the modified nucleic acid molecules of the present invention.

Materials and Methods

DNA constructs for expression of HCV envelope glycoproteins The sequences used to construct vectors for expression of different combinations of HCV envelope glycoproteins were derived from the full length HCV consensus sequence (Yanagi et al., 1997; Genbank Accession #AF011751). The genomic sequence (SEQ ID NO:1) is shown in FIGS. 1*a-c*, the sequence (SEQ ID NO:2) encoding the HCV structural proteins is shown in FIG. 2, and the deduced amino acid sequence (SEQ ID NO:3) of the HCV polyprotein is shown in FIGS. 3*a* and *b*. The pBR cloning vector derivative, p90/HCV FL-long pU, expressing a full-length cDNA of the consensus HCV H77 (1a genotype) sequence (Koykhalov et al., 1997), is available from the NIH AIDS Research & Reference Reagent Program (Catalog #7672). PCR cloning was used to insert translation initiation and stop codons near the ends of the HCV inserts in each construct, and flanking HindIII and XbaI restriction enzyme site at the 5' and 3' termini respectively. The following primer pairs, showing HindIII and XbaI restriction enzyme sites in bold, were used to generate the PCR fragments encompassing the sequences encoding unmodified HCV structural proteins:

```
Upstream (U) and downstream (D) primers
used for construction of the 5'-HindIII-
C-E1-E2-p7-XbaI-3' sequence (FIG. 4):
                                        (SEQ ID NO:11)
U: 5'-aaaaaaaagcttatgagcacgaatcctaaacctc-3'
                                        (SEQ ID NO:12)
D: 5'-aaaaaatctagattatgcgtatgcccgctgaggca-3'

Primers used for construction of 5'-HindIII-C-E1-
E2-XbaI-3' sequence (FIG. 5):
                                        (SEQ ID NO:13)
U: 5'-aaaaaaaagcttatgagcacgaatcctaaacctc-3'
                                        (SEQ ID NO:14)
D: 5'-aaaaaatctagattacgcctccgcttg-3'

Primers used for construction of 5'-HindIII-ΔC-
E1*-E2*-XbaI-3' sequence (FIG. 6):
                                        (SEQ ID NO:15)
U: 5'-aaaaaaaagcttatggacctcatggggtacata-3'
                                        (SEQ ID NO:16)
D: 5'-aaaaaatctagattacgcctccgcttg-3'

Primers used for construction of 5'-HindIII-E1-
E2-p7-XbaI-3' sequence (FIG. 7):
                                        (SEQ ID NO:17)
U: 5'-aaaaaaaagcttatgggttgctctttctctatc-3'
                                        (SEQ ID NO:18)
D: 5'-aaaaaatctagattatgcgtatgcccgctgaggca-3'

Primers used for construction of 5'-HindIII-E1-E2-
XbaI-3' sequence (FIG. 8):
                                        (SEQ ID NO:19)
U: 5'-aaaaaaaagcttatgggttgctctttctctatc-3'
                                        (SEQ ID NO:20)
D: 5'-aaaaaatctagattacgcctccgcttg-3'
```

Fragments encoding unmodified HCV glycoprotein sequences with HindIII and XbaI sticky ends at the 5' and 3' termini respectively were generated by double digestion with HindIII and XbaI, and ligated into HindIII/XbaI-doubly digested pcDNA3.1+expression vector (Invitrogen). Ligation products were transformed into MAX Efficiency® DH5α™ chemically competent cells (Invitrogen). Ampicillin resistant clones were selected and plasmid DNA was purified using a QIAprep® Spin Miniprep Kit (Qiagen, Valencia, Calif.). Recombinant vector constructs were verified by DNA sequencing.

Putative splice donor and/or splice acceptor sites in E1 and E2 sequences (nucleotide positions 887, 888 and 2182 in SEQ ID NO:1) were modified by conservative mutagenesis ($A_{886}\rightarrow C_{886}$ and $A_{2183}\rightarrow T_{2183}$ substitutions) using the QuickChange® Mutagenesis Kit (Stratagene, La Jolla, Calif.). As an example, the sequence (SEQ ID NO:9) of the 5'-HindIII-E1-E2-p7-XbaI-3' construct with A886C and A2183T double mutations is shown in FIG. 9. The predicted intron in E1 (between nucleotide positions 673 and 887 in SEQ ID NO:1) was excised with restriction enzymes following PCR generation of restriction sites flanking the sequence to be deleted. The sequence (SEQ ID NO:10) of the 5'-HindIII-E1-XbaI-3' construct with the intron deleted is shown in FIG. 10. The same nucleotide substitutions and intron deletion modifications were introduced into constructs encoding E1/E2 with or without C and p7 as described above.

Extraction of Viral RNA from Cells

Viral RNA was extracted from cells using a QIAmp Viral RNA Mini Spin Kit (Qiagen) with modifications. Briefly, two extractions with 280 μl of lysis buffer were performed per well and transferred to a 1.7-ml tube. The empty plate was washed with 140 μl of Dulbecco's phosphate-buffered saline containing calcium and magnesium, and pooled into the same tube. RNA extraction and binding to spin columns were carried out according to the manufacturer's instructions. Following a wash with wash buffer, contaminating DNA on the column was removed by treatment with RNase-free DNase (Qiagen) according to the manufacturer's instructions. The bound RNA was washed and eluted from the column in two steps using 30 μl and 40 μl of elution buffer respectively, and the eluates were combined.

Reverse Transcriptase-polymerase Chain Reaction (RT-PCR)

Total RNA was isolated from cells using an RNeasy® Protect Mini Kit (Qiagen) according to the manufacturer's instructions. The RNA was used in a one-tube RT-PCR reaction using a Sensiscript™ Reverse Transcriptase Kit (Qiagen) according to the manufacturer's instructions.

A primer pair comprising SEQ ID NOS: 19 and 20 was used in a PCR reaction to specifically amplify DNA encoding the HCV E1/E2 envelope glycoproteins, thereby placing a HindIII site and an Xba1 site at the 5' and 3' ends, respectively, of the amplified DNA (see FIG. 8), and facilitating cloning into HindIII/Xba1-doubly digested pcDNA-3.1+(Invitrogen) as described.

Transient Expression of HCV Envelope Glycoproteins in HeLa Cells

HeLa cells were seeded overnight on glass coverslips and infected with 5 plaque forming units per cell of a recombinant T7 polymerase-expressing vaccinia virus vector, vTF7.3 (Earl and Moss, 1991), for 1 h at 37° C., followed by lipofection (Invitrogen) with the E1-E2 gene construct. Alternatively, cells were lipofected with plasmid vector containing the E1-E2 construct. Following each of these procedures, protein expression was analyzed 24 h post-infection by immunofluorescent staining using anti-E1 or anti-E2 MAbs. Cells were either fixed in 3% formaldehyde for 20 min at room temperature or fixed/permeabilized with methanol for 20 min at −20° C., followed by washing with 2% gelatin in phosphate-buffered saline (PBS). The fixed cells were then incubated with the anti-E1 MAb, A4 (1:100; provided by Dr. Jean Dubuisson), or the anti-E2, MAb H53 (1:100; provided by Dr. Jean Dubuisson), washed and incubated with a phycoerythrin (PE)-labeled goat anti-mouse IgG secondary antibody (1:100, Pierce, Rockford, Ill.). Coverslips were mounted on slides with Moviol (Calbiochem-Novabiochem Corp., La Jolla, Calif.) and observed under a fluorescence microscope.

Stable Expression of HCV Envelope Glycoproteins in Mammalian Cells

HeLa cells were lipofected with different recombinant plasmid vectors containing HCV envelope glycoprotein gene constructs and placed in medium containing 1 mg/ml G418 (Sigma Chemical, St. Louis, Mo.). G418-resistant cells were pooled and labeled with anti-E2 MAb H53. The 10% most strongly labeled cells were sorted using the FACS Vantage SE (Becton Dickinson, San Jose, Calif.) and subcloned by limiting dilution in order to generate clonal populations. For E1-expressing stable cell lines, cells were subcloned directly after G418 selection and individual clones were tested for E1 expression by immunoblotting. Proteins from whole cell lysates were analyzed by immunoblotting with anti-E2 MAb A11 or anti-E1 MAb A4.

Immunoblot Analysis of HCV Proteins Expressed in Cells

HCV envelope glycoproteins were expressed in HeLa cells with a vaccinia- or a plasmid-based expression system. Cells were lysed in a 1% Nonidet® P40 (NP40), 150 mM NaCl, 50 mM Tris-HCl pH 7.5, 1 mM EDTA buffer containing a protease inhibitor cocktail (Roche, Indianapolis, Ind.). A fraction of the cell lysates was treated with 0.25 units/ml of endoglycosidase H (Boehringer, Indianapolis, Ind.) overnight at 37° C. Proteins were separated by 10% or 12% SDS-PAGE (BioRad, Hercules, Calif.) followed by transfer to Trans-Blot nitrocellulose membranes (BioRad). Membranes were probed either with anti-E2 MAb A11 (1:1000) or anti-E1 MAb A4 (1:1000), followed by horseradish peroxidase (HRP)-labeled goat anti-mouse IgG (1:10,000, Amersham, Piscataway, N.J.) and incubation with a chemifluorescent substrate (Vistra ECF™, Amersham).

Biotinylation and Streptavidin Capture of Cell Surface-localized HCV Envelope Glycoproteins Cell surface proteins of HeLa cells stably expressing HCV envelope glycoproteins were tagged with EZ-Link Sulfo-NHS-LC-Biotin (Pierce) before cell lysis as described by Lu and Kielian (2000). Biotinylated proteins were recovered by incubation of lysates with streptavidin-coupled agarose beads (Molecular Probes, Eugene, Oreg.) for 1 h at 4° C. followed by three washes with the lysis buffer. For detection of E1 proteins, recovered proteins were immunoblotted with anti-E1 MAb A4. Surface-associated E2 proteins in HeLa or NKNT3 cells were detected by flow cytometry analyses after labeling of cells with different anti-E2 MAbs as indicated.

Protein G Immunoprecipitation of Cell Surface-localized E1/E2 Heterdiomers

HeLa cells were stably transfected with constructs for expression of modified HCV envelope glycoproteins. Intact transfected cells were incubated with the anti-E2 MAb H53 (1:100), lysed and incubated with protein G-coupled agarose beads (Oncogene Research Products, San Diego, Calif.) overnight at 4° C., followed by three washes with the lysis buffer. The presence of E1 was detected by immunoblotting with anti-E1 MAb A4 and the presence of E2 was detected by immunoblotting with anti-E2 MAb A11.

Generation of HCV Pseudovirions Expressing Modified HCV Glycoprotein Genes

HCV pseudotyped particles were generated in 293T cells by co-transfection with an HCV envelope glycoprotein vector construct and an HIV-1-based packaging vector, pNL4.3-Luc+env-, expressing a luciferase reporter gene, as described (Bartosch et al., 2003; Hsu et al., 2003). Briefly, 293T cells were plated the day before transfection at a confluence of 1.5 million cells per 10 cm plate. Cells were transfected using the standard calcium phosphate precipitation method with a mix of 15 μg of a pcDNA-3.1-HCVenvelope glycoprotein construct and 5 μg of pNL-Luc+env-DNA per plate. The following day, the medium was replaced with 7 ml of fresh medium and the cells were incubated for another 24 h. Viral supernatant was collected, centrifuged for 10 min at 4,000 rpm or filtered through a 0.2 μm membrane, and either frozen at −70° C. or used directly to infect target cells.

A human T-cell leukemia virus type 1 (HTLV-1)-based packaging system (e.g., Derse et al., 2001) can also be used for preparing HCV pseudotyped particles. Examples of vectors used in this system are described in detail by Derse et al. (2001). Briefly, an initial packaging plasmid, pCMVHT1, encoding Gag-Pol and other HTLV-1 accessory proteins under the control of a cytomegalovirus (CMV) promoter, was constructed from an infectious clone of HTLV-1 (pCS-HTLV; Derse et al., 1995) by replacing the 5'-LTR and 5'-untranslated region with a CMV promoter linked to a fragment from the R region of the LTR. pCMVHT1 lacks the minus-strand primer binding site and virion RNA-packaging elements are absent. Derivatives of pCMVHT1 include pCMVHT-Δenv, generated by deletion of the XhoI fragment (positions 5779 to 6497) in the env gene of pCMVHT1, and pCMVHT-Int$^-$ which was derived from pCMVHT-Δenv by site-directed mutagenesis to create a stop codon (nucleotide position 4700) in the integrase-coding region. A transfer vector, pHTC-luc, containing the 5' and 3' LTR, the psi encapsidation element and the firefly luciferase reporter gene under the control of a CMV promoter, was derived from pCS-HTLV by replacing sequences between the NcoI and MluI sites at positions 1232 and 7482, respectively, with a cassette containing the CMV immediate early promoter joined to the luciferase gene. A modified version of this vector, pHTC-luc-tsa, was generated by inserting a fragment containing the HTLV-1 tax/rex splice acceptor site (positions 6731 to 7436) immediately upstream of the CMV promoter. pHTC-luc-tsa seems to give better transduction efficiency due the presence of the splice acceptor site upstream from the CMV promoter. Other transfer vectors, pHTC-eYFP and pHTC-eYFP-tsa, were derived from pHTC-luc and pHTC-luc-tsa, respectively, by replacing the luciferase gene with the enhanced yellow fluorescent protein (eYFP) gene (Derse et al., 2001).

HCV pseudotyped particles are generated by co-transfecting 293T cells, seeded at 3 million cells in 10-cm plates the previous day, with 10 μg each of any of the HCV envelope glycoprotein-expressing vectors described herein, pCMVHT1, pCMVHT-Δenv, or a similar packaging vector encoding Gag-Pol and other HTLV-1 accessory proteins, and pHTC-luc, pHTC-luc-tsa, pHTC-eYFP, pHTC-eYFP-tsa or a similar transfer vector containing at least the 5' and 3' LTR, the psi encapsidation element and a reporter gene. Cells are transfected by calcium phosphate precipitation. The medium is changed 16 h after co-transfection, and virus-containing supernatant is collected 12 h later. Viral supernatant is cleared by low-speed centrifugation and filtered through a 0.45 μm filter.

Another retroviral packaging system that can be used to prepare HCV pseudotyped particles is derived from spleen necrosis virus (SNV), an avian C-type retrovirus (Parveen et al., 2000). This packaging system employs a transfer vector, pCXL, which is a SNV vector containing 5' and 3' LTRs, an encapsidation sequence and the bacterial β-galactosidase (lacZ) reporter gene inserted in place of the retroviral protein coding sequences. A packaging vector, pRD136, expresses the SNV wild-type Gag-Pol genes from the murine leukemia virus (MLV) U3 promoter and contains the adenovirus tripartite leader sequence (AVtl) downstream of the promoter for enhanced gene expression. Polyadenylation is mediated by the simian virus 40 (SV40) polyadenylation signal sequence (Parveen et al., 2000). HCV pseudotyped particles are generated by essentially as described above for the HIV-1- and HTLV-1-based packaging systems by co-transfecting 293T cells with any of the HCV envelope glycoprotein-expressing vectors disclosed herein, pRD136 or a similar packaging vector encoding Gag-Pol, and pCXL or a similar transfer vector containing a reporter gene.

Infection of Cells with HCV Pseudovirions

One day prior to infection, target cells were plated in 24-well plates at a confluence of 40,000 cells per well. On the day of infection, viral supernatant (500 μl) was applied directly onto the cells and incubated overnight at 37° C. The medium was then changed and cells were incubated for another 24 h. Cells were lysed and luciferase activity quantified using the Luciferase Assay System (Promega, Madison, Wis.) according to the manufacturer's recommendations.

Assay for Identification of Inhibitors of HCV Fusion to Target Cells

The resonance energy transfer (RET) technique (Litwin et al., 1996) may be used to quantify HCV envelope glycoprotein-mediated membrane fusion and to identify inhibitors of HCV fusion to target cells. Briefly, one fusion partner (e.g., an E1/E2-expressing cell line) is labeled with a fluorescent dye such as octadecyl fluorescein (F18; Molecular Probes, Eugene, Oreg.), and the other fusion partner (e.g., a target cell capable of fusing with HCV) is labeled with a dye such as octadecyl rhodamine (R18; Molecular Probes, Eugene, Oreg.). The octadecyl versions of these probes spontaneously insert into the plasma membranes of cells using the labeling protocol described by Litwin et al. (1996). The fluorochromes are chosen such that the emission spectrum of one (F18) overlaps the excitation spectrum of the second (R18).

F18 or R18 is dissolved in ethanol at 5-10 mg/ml and diluted approximately 1000-fold into the appropriate cell culture medium. The exact concentration in the medium is adjusted to bring the OD to 0.34 at 506 nm (F18) or 1.04 at 565 nm (R18). The labeled cells are then contacted under conditions that permit cell fusion. Monolayers of cells are incubated with the appropriate medium overnight, then washed and counted. 100,000 cells of each type are mixed together in wells of a 24-well tissue culture plate and incubated at 37° C. At intervals after mixing, the cells are removed with EDTA, washed and placed in a fluorometer cuvette.

Upon cell fusion, the F18 and R18 associate together closely enough that stimulation of F18 results in resonance energy transfer to R18 and emission at the R18 emission wavelengths. The dyes are excited at the wavelengths indicated in Table 1, and fluorescence measured at the indicated emission wavelengths (Table 1) using a LS50 fluorometer (Perkin-Elmer).

TABLE 1

Excitation and emission wavelengths used in RET assay.

| Excitation Wavelength (nm) | Emission Wavelength (nm) | Measurement obtained |
|---|---|---|
| 450 | 530 | Total F18 fluorescence |
| 557 | 590 | Total R18 fluorescence |
| 450 | 590 | RET* |

*The calculation of RET requires first subtracting the fluorescence due to direct F18 and R18 fluorescence following excitation at 450 nm and emission at 590 nm. The fluorescence measurements are determined by measuring the fluorescence of cells labeled with each dye separately. The RET value, calculated as described by Litwin et al. (1996), is divided by the total R18 fluorescence to give a % RET value.

Assay for Identification of Inhibitors of HCV Entry Into Target Cells

HCV pseudovirions expressing modified HCV glycoproteins are used to infect target cells as described above. A panel of liver target cells lines, available from the ATCC (Catalog #CRL-HB-8065) and including HepG2 human hepatocellular carcinoma cells, is used. Alternatively, fresh or cryopreserved human hepatocytes, isolated from adult human liver biopsies (available from Cambrex/Clonetics, San Diego, Calif.), may be used. Duplicate infections are performed in the presence and absence respectively of the agent being assayed for entry inhibitory activity. The agent is added to the target cells, pseudovirions or both and incubated for 0-4 h. Alternatively, the agent is added after contacting the target cells with the pseudovirions but prior to viral entry. The degree of inhibition is quantified as a decrease in the level of luciferase activity measured in the presence of an inhibitory agent compared to the level observed in the absence of that agent.

Results

Plasmid-based Expression Causes Cell Surface Localization of E1 and E2

Constructs were generated for expression of full-length unmodified HCV E1 (E1), E2 (E2) and E1/E2 (E1-E2), using HCV envelope glycoprotein gene sequences derived by PCR amplification of p90/HCV FL-long pU which contains a cDNA insert corresponding to the full-length genome of an infectious HCV isolate, H77 (Kolykhalov et al., 1997). The first nucleotide of the capsid (C) start codon is defined as position +1 in the HCV genome (SEQ ID NO:1; see FIG. 1). Therefore, C extends from nucleotides +1 to 510 inclusive, E1 extends from nucleotides 511 to 1149, E2 extends from nucleotides 1111 to 2238, E1-E2 extends from nucleotides 511 to 2238, and p7 extends from nucleotides 2238 to 2427.

Transient expression of HCV envelope glycoproteins was achieved by lipofection of the different expression plasmids into HeLa cells. Alternatively, HeLa cells were infected with vTF7.3, a vaccinia virus vector expressing T7 polymerase, followed by lipofection with HCV E1/E2-expression plasmids (resulting in cytoplasmic transcription from the T7 promoter in pcDNA3.1+).

Intracellular but not cell surface-associated E1 and E2 were detected by immunofluorescence after vaccinia virus-driven expression of E1-E2 (FIGS. 11*a-d*). In contrast, E1 and E2 were detected both intracellularly and on the cell surface following plasmid-based expression of the E1-E2 construct (FIGS. 11*e-h*). Intracellular staining of envelope glycoproteins was comparable in the two expression systems (FIGS. 11*a, b, e, f*), indicating that similar levels of E1 and E2 expression were achieved in both systems but that transport to the cell surface was not occurring in the vaccinia-based expression system. Differences in expression levels were not observed between envelope glycoproteins expressed as single proteins (E1 and E2) or as part of an E1-E2 polyprotein (E1-E2, data not shown). Similar expression patterns were obtained after transient expression of E1 and E2 by vaccinia- and plasmid-based systems in a hepatoma cell line, HepG2 (data not shown).

Size Heterogeneity of HCV Envelope Glycoproteins Expressed in HeLa Cells

Figure 12:
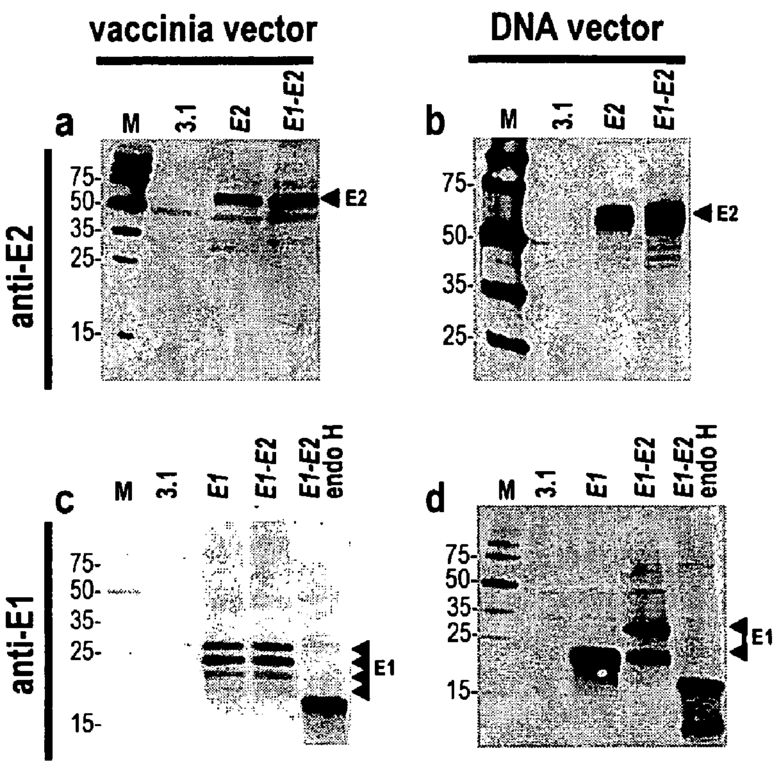
FIG. 12. Characterization of E1 and E2 proteins. Unmodified HCV envelope glycoprotein genes (E1, E2 and E1-E2) were expressed in HeLa cells with a vaccinia-(a, c) or a plasmid-based system (b, d), and protein expression was analyzed by immunoblotting of cell lysates with anti-E2 MAb A11 (a, b) or anti-E1 MAb A4 (c, d) (see Methods for details). M, molecular weight markers showing sizes in kDa; 3.1, cell lysate from cells transfected with the expression vector, pcDNA3.1+ (Invitrogen, Carlsbad, Calif.); endoH, endoglycosidase H-treated lysate. Arrowheads indicate the positions of E1 and E2 proteins on the blots.

Vaccinia vector- and plasmid vector-based expression of unmodified E2 and E1-E2 constructs HCV invariably generated a major E2 protein species with an apparent molecular weight of 62 kDa (FIGS. 12*a, b*). However, vaccinia expression of unmodified E1 and E1-E2 constructs generated four E1 protein species of 18, 21, 24 and 27 kDa apparent molecular weights (FIG. 12*c*). Treatment of cell lysates with endoglycosidase H generated a single low molecular weight band corresponding to the deglycosylated E1 protein core (FIG. 12*c*). The 27 kDa species therefore corresponds to the fully glycosylated E1 protein, whereas the lower molecular weight species correspond to incomplete glycosylation products. By contrast, plasmid-based expression of E1-E2 generated E1 proteins of 27 and 20 kDa apparent molecular weights (FIG. 12*d*). The 20 kDa E1 species was not the result of hypoglycosylation because two E1 protein species were still present after endoglycosidase H treatment of cell lysates (FIG. 12*d*, see below).

A Putative Intron is Excised from the E1 Gene Transcribed in Cell Nuclei

Vaccinia virus-based expression of heterologous genes depends on transcription in the cytoplasm. By contrast, transient and stable expression from plasmid vectors requires transcription in the nucleus, followed by mRNA maturation and transport to the cytoplasm. It appeared likely that mRNA modifications accounted for the different E1 species expressed by plasmid vectors. RT-PCR was therefore performed on RNA extracts of HeLa cells stably expressing E1. Sequence analyses of the PCR products detected a deletion between nucleotides 675 and 887 (inclusive), which preserves the E1 reading frame but results in a protein with a 71 amino acid deletion (FIG. 13*a* and data not shown). This deletion was not present in PCR products derived by amplification of genomic DNA containing the integrated E1 construct (data not shown).

Figure 14:
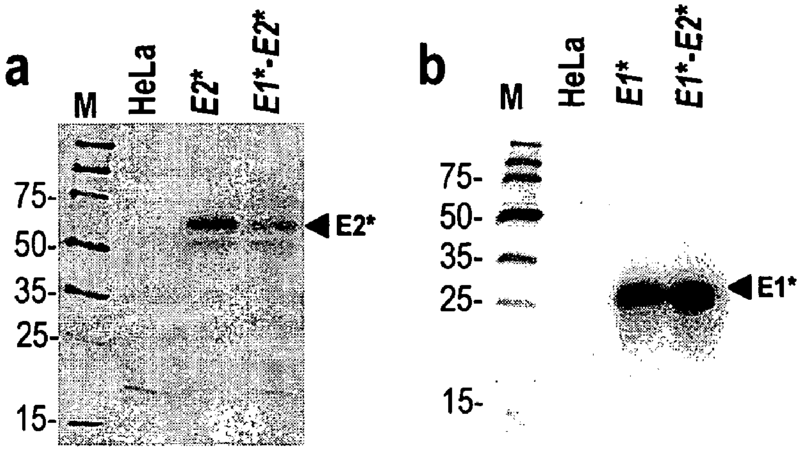
FIG. 14. Stable expression of E1 and E2 lacking putative splice acceptor sites. Proteins from whole cell lysates of HeLa cells, stably transfected with different constructs comprising modified E1, E2 or E1-E2 genes (indicated by "*"), were analyzed by immunoblotting with anti-E2 MAb A11 (a) or anti-E1 MAb A4 (b). M, molecular weight markers showing sizes in kDa. Arrowheads indicate the positions of full-length E1 and E2 proteins.

Analysis of the entire HCV genomic sequence by a splice site prediction neural network (available at http://www.fruitfly.org/seq_tools/splice.html) revealed the presence of a putative splice donor site at position 675 of E1, whereas putative splice acceptor sites were found at positions 887 of E1 and 2183 of E2 (see FIG. 14*a*). These findings suggested that putative intron splicing between positions 675 and 887 resulted in expression of a truncated E1 protein, corresponding to the 20 kDa species observed after transient expression of E1 and E1-E2 constructs. The absence of a larger deletion corresponding to nucleotides between positions 675 and 2183 suggests that the splice acceptor at position 2183 is not functional.

Nature of E1 Proteins Expressed from Modified E1 Genes

E1-expression constructs were generated wherein the splice acceptor site in E1 was removed by conservative substitution of $A_{886}GG$ to $C_{886}GT$ (E1*), or the sequence encoding the putative intron between positions 675 and 887 was deleted ($E1^{\Delta}$). Transient, plasmid-based expression of both E1 and $E1^{\Delta}$ generated a single 20 kDa protein species (FIG. 13*b*). A single, 27 kDa protein species was generated by E1*, wherein the splice acceptor site was mutated (FIG. 13*b*). The 2.0 kDa protein species generated by unmodified E1 is therefore the result of E1 mRNA splicing, whereas the 27 kDa protein species corresponds to full-length E1. Secondary structure may partially obstruct splice sites in E1-E2 mRNA leading to expression of full-length (27 kDa) as well as truncated (20 kDa) forms of E1 (cf. E1-E2 lane in FIG. 12*d*).

The putative splice acceptor site in position 887 was also eliminated by conservative mutagenesis in all constructs to ensure that splicing would not occur. To guard against the splice acceptor site at position 2183 in E2 becoming functional in the absence of the upstream splice acceptor eliminated from position 887, that putative splice acceptor site was also modified by a conservative $A_{2183} \rightarrow T_{2183}$ substitution. Constructs expressing modified E1, E2 or E1-E2 (indicated by "*", i.e., E1*, E2* or E1*-E2*) were stably transfected into HeLa cells. Stable clones were also generated with constructs expressing E1/E2 in conjunction with p7 (extending from nucleotides 511 to 2427), an HCV structural protein of unknown function. RT-PCR analyses of RNA extracts showed that the length of transcripts matched the full-length of the coding sequences, indicating that putative intron splicing was no longer occurring (data not shown). E2* and E1*-E2* expression generated a major 62 kDa protein corresponding to E2 (FIG. 14*a*). Immunoblotting demonstrated that E1 was now expressed as a single 27 kDa species by E1* and E1*-E2* constructs (FIG. 14*b*).

Immunological Detection of Cell Surface-localized E1 and E2

Figure 15:
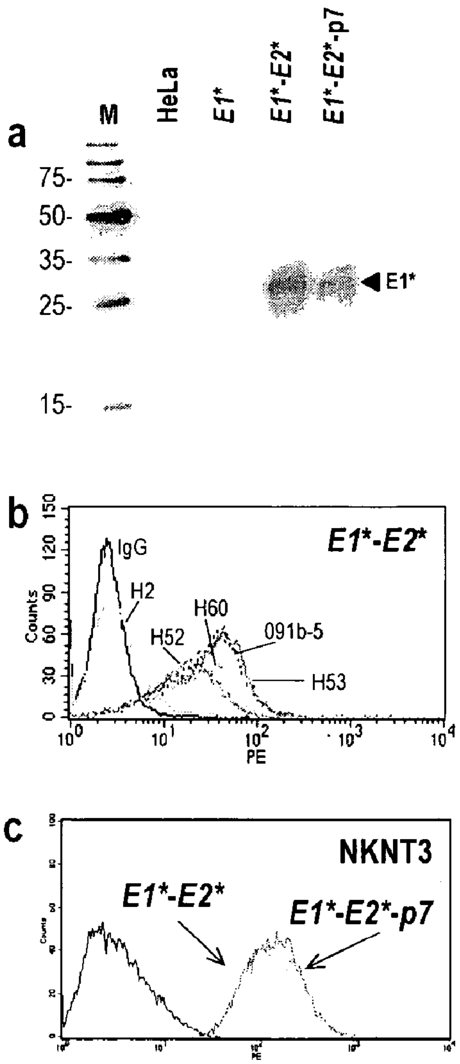
FIG. 15. Cell surface expression of E1 and E2 lacking putative splice acceptor sites. (a) Cell surface proteins of HeLa cells stably expressing modified E1*, E1*-E2* and E1*-E2*-p7 were tagged with biotin before lysis. After cell lysis, the biotinylated proteins were immunoblotted with anti-E1 MAb A4. The arrowhead indicates the position of E1 proteins. (b) Cell surface-associated E2 proteins generated by stable expression of E1*-E2* and E1*-E2*-p7 were detected by flow cytometry analyses after labeling of cells with five different anti-E2 MAbs, H2, H52, H53, H60 and 091b-5 or a control mouse IgG. (c) Cell surface-associated E2 proteins, generated by stable expression of E1*-E2* and E1*-E2*-p7 in NKNT3 cells, were detected by anti-E2 MAb H53.

Cell surface-associated E1 protein could not be detected in any of the stable HeLa clones by flow cytometry using two different anti-E1 MAbs, A4 (Dubuisson et al., 1994) and 081-5 (Austral Biologicals, San Ramon, Calif.) (data not shown). This suggests that the E1 epitopes recognized by these MAbs may not be accessible in the full-length protein. Cell surface-associated E1 was readily detected, however, by cell surface biotinylation followed by streptavidin capture and immunoblotting of E1*-E2* and E1*-E2*-p7-expressing cells with an anti-E1 MAb (FIG. 15*a*). When E1 was expressed alone, it was not detectable on the cell surface, suggesting that coexpression of E2 is required for efficient transport of E1 to the plasma membrane (FIG. 15*a*).

Cell surface-associated E2 was detected in stable HeLa clones by flow cytometry after labeling with four different anti-E2 MAbs of E2*-, E1*-E2*- as well as E1*-E2*-p7-expressing cells (FIG. 15*b* and data not shown). MAb H2, which has been reported to recognize E1/E2 heterodimers, did not recognize cell surface E2, but this antibody is also not reactive with HCV particles in patient sera (Deleersnyder et al., 1997). E1*-E2* and E1*-E2*-p7 were also stably expressed in hepatic NKNT3 cells. These cells display morphological characteristics of liver parenchyma cells, express key genes of liver metabolism, and are not tumorigenic in SCID mice (Kobayashi et al., 2000; 2001). E2 was readily detected on the surface of NKNT3 cells, suggesting that plasma membrane localization is an inherent property of HCV envelope glycoproteins rather than of the cell line in which they are expressed (FIG. 15*c*). Coexpression of E1/E2 with p7 did not appear to influence the processing and cell surface localization of the envelope glycoproteins.

E1 and E2 Form Non-covalent Heterodimers in Cell Membranes

Figure 16:
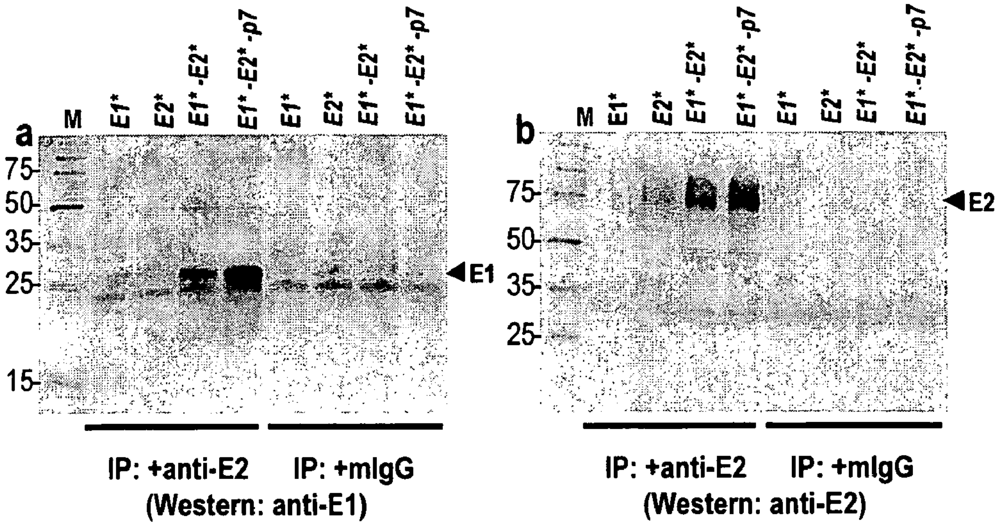
FIG. 16. Heterodimerization of E1 and E2 on the cell surface. HeLa cells stably expressing modified HCV envelope glycoproteins were incubated with the anti-E2 MAb H53, lysed and incubated with protein G-coupled agarose beads. Lysates from cells treated with a mouse immunoglobulin (mIgG), but not H53, were used as a control. E1 was detected by immunoblotting with anti-E1 MAb A4 (a), whereas E2 was detected by immunoblotting with anti-E2 MAb A11 (b). Arrowheads indicate the positions of full-length E1* and E2* proteins.

Cell surface-associated E1 and E2 were analyzed for their ability to form non-covalent heterodimers. HeLa cells stably expressing different combinations of E1, E2 and p7 were preincubated with an anti-E2 MAb, and protein-antibody complexes were recovered by immunoprecipitation of cell lysates with G protein-coupled agarose beads. In this manner, cell surface-associated envelope glycoproteins were selected for analysis by SDS-PAGE and immunoblotting with an anti-E1 MAb. E1 readily coimmunoprecipitated with E2 only in cells expressing E1*-E2*, and only if the cells were preincubated with an anti-E2 MAb (FIG. 16*a*). Similarly, E2 was detected in cells expressing E2*, E1*-E2* or E1*-E2*-p7, only if the cells were preincubated with an anti-E2 MAb (FIG. 16*b*). E1 and E2 proteins associated with the plasma membrane therefore also form non-covalent heterodimers.

Preliminary Evaluation of Pseudovirions Expressing Modified HCV Glycoproteins

Envelope constructs with mutated E1-E2 splice acceptor sites generated higher concentrations of HCV pseudovirions than non-mutated E1-E2 sequences (data not shown). This is an important finding because the E1 and E2 proteins used for pseudotyping, though translated from modified nucleotide sequences, are of identical length and amino acid sequence as the native HCV glycoproteins. However, homogeneous proteins are generated when the modified gene sequences are expressed from DNA plasmids. Therefore, the nucleic acid modifications in E1 and E2 may induce more efficient folding of the encoded protein, thereby enhancing the packaging, assembly, budding and ultimately stability of the pseudovirions. The inclusion of all or part of the capsid, C, further enhanced pseudoparticle production, suggesting that the C region may stabilize protein folding. Importantly, these pseudoparticles were found to be fusion-competent and were demonstrated to enter hepatic cell lines with high efficiency. They therefore provide powerful tools to help elucidate the molecular mechanisms underlying HCV attachment to, fusion with and entry into cells, and other aspects of HCV pathogenesis. These pseudovirions can also be used in assays for identifying inhibitors of HCV entry.

Discussion

HCV envelope glycoproteins, E1 and E2, have previously been described to form membrane-anchored, non-covalent heterodimers that are retained in the ER, where HCV budding is believed to occur (Op De Beeck et al., 2001). The colocolization of heterodimerization and ER retention signals to residues in the TM domains of E1 and E2 suggested that the two functions cannot be dissociated (Op De Beeck et al., 2001). Thus, it has been difficult to generate cell surface-associated variants of E1/E2 heterodimers which would be invaluable for developing cell fusion and entry assays and generating virus pseudotypes. Attempts to create such variants have hitherto focused on fusing E1 and E2 ectodomains to the TM domains of Vesicular Stomatitis Virus (VSV) G or influenza HA envelope glycoproteins, which have no known dimerization function (Flint et al., 1999; Lagging et al., 1998; Takikawa et al., 2000). Additionally, in these previous studies, chimeric E1 and E2 proteins were translated from separate mRNAs, which may have further minimized their potential to form native heterodimers. Even though E2-HA chimeras underwent pH-dependent conformational changes and were incorporated into influenza virus particles, they did not induce fusion with target cells (Flint et al., 1999). HCV-VSV chimeric envelope glycoproteins also did not appear to reproducibly model HCV fusion and entry (cf. Buonocore et al., 2002; Lagging et al., 1998; Lagging et al., 2002; Matsuura et al., 2001; Meyer et al., 2000; Takikawa et al., 2000).

The initial goal of the present study was to create chimeric HCV envelope glycoproteins that would be expressed on the cell surface as E1/E2 heterodimers and that would be incorporated onto pseudovirions and mediate entry into HCV target cells. A strategy was therefore chosen wherein the ectodomains of HCV E1 and E2 were fused to the TM domains of E1 and E2 from a related alphavirus, the Semliki Forest virus (SFV). The SFV envelope glycoproteins form cell surface-associated heterodimers that efficiently pseudotype heterologous viral nucleocapsids in order to mediate their entry into host cells. It was found that chimeric HCV-SFV envelope glycoproteins were expressed on the cell surface and resembled unmodified HCV envelope glycoproteins in size and post-translational processing. However, a surprising finding, and one that changed the focus the study, was the expression of unmodified HCV E1 and E2 on the cell surface.

E2 was detected on the cell surface by flow cytometry with four different anti-E2 MAbs. Cell surface-associated E2 expression was also detected in a hepatic cell line and was not influenced by the presence of p7. By biotin-tagging cell surface proteins, it was demonstrated that full-length E1 was also associated with the plasma membrane. Most importantly, it was found that E1 protein could be specifically coimmunoprecipitated with an anti-E2 MAb, thus demonstrating that cell surface-associated E1 and E2 form non-covalent heterodimers.

One of the complicating factors in identifying properly folded and functional E1 and E2 has been the multitude of expression systems used to study these proteins, and a careful survey of the literature reveals significant diversity in the number and size of protein species corresponding to E1 and E2. In the present study, unmodified and chimeric envelope glycoproteins were generated using two different expression systems. The use of vaccinia-based expression is justifiable on the premise that it circumvents the nucleus, just as HCV replication does. In this expression system, E1 and E2 remain intracellular. Vaccinia replication, however, is known to modify internal cellular membranes as well as the translation machinery (Person-Fernandez and Beaud, 1986; Ploubidou et al., 2000; Rice and Roberts, 1983; Risco et al., 2002: Rodriguez et al., 1997; Sanger et al., 2001), and the apparent trapping of HCV envelope glycoproteins inside the cell may be an artifact of these vaccinia-induced modifications. Indeed, vaccinia-based expression has been shown to cause ER retention of other viral envelope glycoproteins (Sanger et al., 2001; Szepanski et al., 1994).

The observation that vaccinia-based expression generates hypoglycosylated E1 proteins prompted the use of an alternative, plasmid-based system for expressing HCV envelope glycoproteins. Plasmid-based expression of proteins typically does not adversely affect cellular protein synthesis but does involve nuclear transcription, which is not a natural part of HCV replication. Indeed, it was clearly demonstrated that plasmid-based expression of HCV envelope glycoproteins results in putative intron excision in E1 mRNA that is subsequently translated to give a truncated protein. This finding highlights an inherent complication in expressing RNA virus proteins by DNA-based expression systems.

To circumvent the problem of excision of the potential intron from the E1 gene, which results in the production of heterogeneous E1 proteins, site-specific mutagenesis was used to introduce conservative mutations in the E1 and E2 coding sequences. These mutations eliminated putative intron acceptor sites and prevented intron excision but did not alter the sequence of the encoded E1 and E2 proteins. Thus, E1 and E2 proteins identical to the native HCV glycoproteins were expressed in cells, and these proteins were found to be localized in the plasma membrane. The modified nucleic acid molecules encoding HCV glycoproteins have several potential applications. First, for example, although the envelope glycoproteins translated from the mutated constructs have identical amino acid sequences to native HCV envelope glycoproteins, the translation of the mRNA and co-translational folding of the protein may be different from unmodified HCV glycoproteins. Moreover, the homogeneity of the envelope proteins produced from modified DNA sequences may be advantageous, compared to the synthesis of a mixture of full length and truncated proteins from unmodified coding sequences. These differences may enable more efficient heterodimerization of E1 and E2, and lead to enhanced packaging of virions. Alternatively, interactions with other components (C, p7) of the HCV envelope complex may be more efficient with the envelope glycoproteins synthesized from modified coding sequences than from native HCV coding sequences.

Second, the modified nucleic acids encoding the envelope proteins may allow more efficient production of virus pseudotype particles in transient expression systems or in packaging cell lines. They may also be able to package HCV replicons (Blight et al., 2000) or be useful in the culture of infectious, replication-competent HCV. Further, they may facilitate the manufacture of vaccines using nucleic acid vectors (DNA, RNA, viruses) or proteins.

Third, modified HCV glycoprotein sequences could be invaluable in developing novel HCV fusion and entry assays, including the use of pseudovirion systems and resonance energy transfer (RET) assays, as well as in studying of viral budding from membranes and viral particle formation. They may have further utility in developing novel virus replicon packaging systems with HCV or non-structural protein vectors from other viruses.

Fourth, the production of homogeneous HCV envelope glycoproteins may be useful in vaccine design or in generating monoclonal antibodies to HCV as these glycoproteins may contain epitopes that are capable of eliciting neutralizing antibodies to native HCV.

Fifth, these novel systems for expressing cell surface-localized, full length HCV envelope glycoproteins enable the design of screening assays to identify agents that inhibit HCV fusion and entry into cells.

Recently, two groups reported that HCV envelope glycoproteins are able to pseudotype retroviral particles and mediate their entry into target cells (Bartosch et al., 2003; Hsu et al., 2003). Both groups used plasmid vectors to express E1/E2 from unmodified coding sequences, and thus the pseudoviral envelopes likely contained both full-length and truncated E1 proteins. The present study has confirmed that unmodified HCV envelope glycoproteins are able to mediate entry of retroviral pseudotypes into several hepatic and non-hepatic cell lines as well as primary hepatocytes. Studies are underway to determine how the presence of truncated E1 species in pseudoviral envelopes affects entry into different target cells. These studies will permit optimization of pseudovirion entry mediated by HCV envelope glycoproteins, which will facilitate structure/function studies of HCV envelope glycoproteins as well as the identification of HCV receptors and target cells.

It remains to be determined whether cell surface-associated E1/E2 heterodimers have any physiological relevance in the viral replication cycle. The observation that HCV envelope glycoproteins are expressed on the surface of cells that closely resemble primary hepatocytes implies that there is no specific retention mechanism for HCV envelope glycoproteins in liver cells. The postulated HCV replication cycle is based on analogies to the closely related flavi- and pestiviruses and it is generally assumed that flaviviridae bud into the endoplasmic reticulum and mature by passage into cytoplasmic vesicles (Pettersson, 1991). Thus far, the cellular localization of HCV envelope glycoproteins and particles has mostly been studied in cells transfected or infected in vitro. Virus-like particles mostly occurred in cytoplasmic vesicles, suggesting vesicle-based morphogenesis of HCV (Dash et al., 1997; Egger et al., 2002; Greive et al., 2002; Iacovacci et al., 1997; Pietschmann et al., 2002; Serafino et al., 1997; Shimizu et al., 1996). No study to date, however, has clearly documented the budding and maturation process of HCV, probably because they do not occur in currently available experimental systems though it is also possible that budding of HCV is an extremely rare event that is difficult to detect by standard techniques. Ongoing studies will address these questions by expressing E1/E2 envelope glycoproteins in human primary hepatocytes.

REFERENCES

U.S. Pat. No. 3,645,852 issued to Axen et al. on Feb. 29, 1972.

U.S. Pat. No. 4,816,567 issued to Cabilly et al. on Mar. 28, 1989.

U.S. Pat. No. 5,225,539 issued to Winter on Jul. 6, 1993.

U.S. Pat. No. 5,545,806 issued to Lonberg et al. on Aug. 13, 1996.

U.S. Pat. No. 5,545,807 issued to Surani et al. on Aug. 13, 1996.

U.S. Pat. No. 5,585,089 issued to Queen et al. on Dec. 17, 1996.

U.S. Pat. No. 5,591,669 issued to Krimpenfort et al. on Jan. 7, 1997.

U.S. Pat. No. 5,598,369 issued to Chen et al. on Jan. 28, 1997.

U.S. Pat. No. 5,693,761 issued to Queen et al. on Dec. 2, 1997.

U.S. Pat. No. 5,882,852 issued to Bukh et al. on Mar. 16, 1999.

U.S. Pat. No. 6,150,584 issued to Kucherlapati et al. on Nov. 21, 2000.

U.S. Pat. No. 6,572,864 issued to Bukh et al. on Jun. 3, 2003.

PCT International Application No. PCT/US89/05857, filed Dec. 28, 1989, International Publication No. WO 90/07861, published Jul. 26, 1990.

PCT International Application No. PCT/IB2003/003882, filed Sep. 12, 2003, International Publication No. WO 2004/024904 A2, published Mar. 25, 2004.

Alter, H. J. and L. B. Seef (1993) Transfusion-associated hepatitis. In "Viral Hepatitis" (Z. A. Thomas, ed.). Churchill Livingstone, Edinburgh.

Anonymous (1999) Global surveillance and control of hepatitis C. Report of a WHO Consultation organized in collaboration with the Viral Hepatitis Prevention Board, Antwerp, Belgium. J. Viral. Hepat. 6: 35-47.

Bartenschlager, R. and V. Lohmann (2000) Replication of hepatitis C virus. J. Gen. Virol. 81: 1631-1648.

Bartosch, B., J. Dubuisson and F. L. Cosset (2003) Infectious hepatitis c virus pseudo-particles containing functional E1-E2 envelope protein complexes. J. Exp. Med. 197: 633-642.

Blight, K. J., A. A. Kolykhalov and C. M. Rice (2000) Efficient initiation of HCV RNA replication in cell culture. Science 290: 1972-1974.

Buonocore, L., K. J. Blight, C. M. Rice and J. K. Rose (2002) Characterization of vesicular stomatitis virus recombinants that express and incorporate high levels of hepatitis C virus glycoproteins. J. Virol. 76: 6865-6872.

Charloteaux, B., L. Lins, H. Moereels and R. Brasseur (2002) Analysis of the C-terminal membrane anchor domains of hepatitis C virus glycoproteins E1 and E2: toward a topological model. J. Virol. 76: 1944-1958.

Cocquerel, L., S. Duvet, J. C. Meunier, A. Pillez, R. Cacan, C. Wychowski and J. Dubuisson (1999) The transmembrane domain of hepatitis C virus glycoprotein E1 is a signal for static retention in the endoplasmic reticulum. J. Virol. 73: 2641-2649.

Cocquerel, L., J. C. Meunier, A. Op de Beeck, D. Bonte, C. Wychowski and J. Dubuisson (2001) Coexpression of hepatitis C virus envelope proteins E1 and E2 in cis improves the stability of membrane insertion of E2. J. Gen. Virol. 82: 1629-1635.

Cocquerel, L., J. C. Meunier, A. Pillez, C. Wychowski and J. Dubuisson (1998) A retention signal necessary and sufficient for endoplasmic reticulum localization maps to the transmembrane domain of hepatitis C virus glycoprotein E2. J. Virol. 72: 2183-2191.

Cocquerel, L., A. Op de Beeck, M. Lambot, J. Roussel, D. Delgrange, A. Pillez, C. Wychowski, F. Penin and J. Dubuisson (2002) Topological changes in the transmembrane domains of hepatitis C virus envelope glycoproteins. EMBO J. 21: 2893-2902.

Cocquerel, L., C. Wychowski, F. Minner, F. Penin and J. Dubuisson (2000) Charged residues in the transmembrane domains of hepatitis C virus glycoproteins play a major role in the processing, subcellular localization, and assembly of these envelope proteins. J. Virol. 74: 3623-3633.

Dash, S., A. B. Halim, H. Tsuji, N. Hiramatsu and M. A. Gerber (1997) Transfection of HepG2 cells with infectious hepatitis C virus genome. Am. J. Pathol. 151: 363-373.

Deleersnyder, V., A. Pillez, C. Wychowski, K. Blight, J. Xu, Y. S. Hahn, C. M. Rice and J. Dubuisson (1997) Formation of native hepatitis C virus glycoprotein complexes. J. Virol. 71: 697-704.

Derse, D., J. Miksvits, M. Polianova, E. K. Felber ond F. Ruscetti (1995) Virions released from cells transfected with a molecular clone of human T-cell leukemia virus type I give rise to primary and secondary infections of T cells. J. Virol.69: 1907 1912.

Derse, D., S. A. Hill, P. A. Lloyd, H. K. Chung and B. A. Morse (2001) Examining human T-lymphotropic virus type 1 infection and replication by cell-free infection with recombinant virus vectors. J. Virol. 75: 8461-8468.

De Vos, R., C. Verslype, E. Depla, J. Fevery, B. Van Damme, V. Desmet and T. Roskams (2002) Ultrastructural visualization of hepatitis C virus components in human and primate liver biopsies. J. Hepatol. 37: 370.

Dubuisson, J., S. Duvet, J. C. Meunier, A. Op De Beeck, R. Cacan, C. Wychowski and L. Cocquerel (2000) Glycosylation of the hepatitis C virus envelope protein E1 is dependent on the presence of a downstream sequence on the viral polyprotein. J. Biol. Chem. 275: 30605-30609.

Dubuisson, J., H. H. Hsu, R. C. Cheung, H. B. Greenberg, D. G. Russell and C. M. Rice (1994) Formation and intracellular localization of hepatitis C virus envelope glycoprotein complexes expressed by recombinant vaccinia and Sindbis viruses. J. Virol. 68: 6147-6160.

Duvet, S., L. Cocquerel, A. Pillez, R. Cacan, A. Verbert, D. Moradpour, C. Wychowski and J. Dubuisson (1998) Hepatitis C virus glycoprotein complex localization in the endoplasmic reticulum involves a determinant for retention and not retrieval. J. Biol. Chem. 273: 32088-32095.

Earl, P. L. and B. Moss (1991) Generation of recombinant vaccinia viruses. In "Current Protocols in Molecular Biology" (F. M. Ausubel, R. Brent, R. E. Kingston, D. D. Moore, J. G. Seidman, J. A. Smith and K. Struhl (eds.), Greene Publishing Associates/Wiley Interscienc, New York, pp. 16.17.1-16.17.16.

Egger, D., B. Wolk, R. Gosert, L. Bianchi, H. E. Blum, D. Moradpour and K. Bienz (2002) Expression of hepatitis C virus proteins induces distinct membrane alterations including a candidate viral replication complex. J. Virol. 76: 5974-5984.

Flint, M. and J. A. McKeating (1999) The C-terminal region of the hepatitis C virus E1 glycoprotein confers localization within the endoplasmic reticulum. J. Gen. Virol. 80: 1943-1947.

Flint, M., J. M. Thomas, C. M. Maidens, C. Shotton, S. Levy, W. S. Barclay and J. A. McKeating (1999) Functional analysis of cell surface-expressed hepatitis C virus E2 glycoprotein. J. Virol. 73: 6782-6790.

Fry, D. E. and L. M. Flint (1997) Hepatitis: an overview of important issues. Bull. Am. Coll. Surg. 82: 8-13.

Gardner, J., R. J. Durso, R. R. Arrigale, G. P. Donovan, P. J. Maddon, T. Dragic and W. C. Olson (2003) L-SIGN is a liver-specific capture receptor for hepatitis C virus. Proc. Natl. Acad. Sci. USA 100: 4498-4503.

Goldberg, M., L. Smith, II, N. Tamayo and A. S. Kiselyov (1999) Solid support synthesis of 14-macrocycles containing 4-hydroxyproline structural unit via $S_NAr$ methodology. Tetrahedron 55: 13887-13898.

Grakoui, A., C. Wychowski, C. Lin, S. M. Feinstone and C. M. Rice (1993) Expression and identification of hepatitis C virus polyprotein cleavage products. J. Virol. 67: 1385-1395.

Greive, S. J., R. I. Webb, J. M. Mackenzie and E. J. Gowans (2002) Expression of the hepatitis C virus structural proteins in mammalian cells induces morphology similar to that in natural infection. J. Viral Hepat. 9: 9-17.

Hsu, M., J. Zhang, M. Flint, C. Logvinoff, C. Cheng-Mayer, C. M. Rice and J. A. McKeating (2003) Hepatitis C virus glycoproteins mediate pH-dependent cell entry of pseudotyped retroviral particles. Proc. Natl. Acad. Sci. USA 100: 7271-7276.

Iacovacci, S., A. Manzin, S. Barca, M. Sargiacomo, A. Serafino, M. B. Valli, G. Macioce, H. J. Hassan, A. Ponzetto, M. Clementi, C. Peschle and G. Carloni (1997) Molecular characterization and dynamics of hepatitis C virus replication in human fetal hepatocytes infected in vitro. Hepatology 26: 1328-1337.

Kiselyov, A., S. Eisenberg and Y. Luo (1998) Solid support synthesis of 14-membered macrocycles containing the thioether bridge via $S_NAr$ methodology. Tetrahedron 54: 10635-10640.

Kiselyov, A., S. Eisenberg and Y. Luo (1999a) Tetrahedron Lett. 40: 2465-2468.

Kiselyov, A., L. Smith, II and P. Tempest (1999b) Solid support synthesis of 14- and 17-membered macrocycles via the $S_NAr$ methodology. Tetrahedron 55: 14813-14822.

Kobayashi, N., T. Fujiwara, K. A. Westerman, Y. Inoue, M. Sakaguchi, H. Noguchi, M. Miyazaki, J. Cai, N. Tanaka, I. J. Fox and P. Leboulch (2000) Prevention of acute liver failure in rats with reversibly immortalized human hepatocytes. Science 287: 1258-1262.

Kobayashi, N., H. Noguchi, K. A. Westerman, T. Watanabe, T. Matsumura, T. Totsugawa, T. Fujiwara, P. Leboulch and N. Tanaka (2001) Cre/loxP-based reversible immortalization of human hepatocytes. Cell Transplant. 10: 383-386.

Kohler, G. and C. Milstein (1975) Continuous cultures of fused cells secreting antibody of predefined specificity. Nature 256: 495-497.

Kolykhalov, A. A., E. V. Agapov, K. J. Blight, K. Mihalik, S. M. Feinstone and C. M. Rice (1997) Transmission of hepatitis C by intrahepatic inoculation with transcribed RNA. Science 277: 570-574.

Krieg, A. M., A. K. Yi, S. Matson, T. J. Waldschmidt, G. A. Bishop, R. Teasdale, G. A. Koretzky and D. M. Klinman (1995) CpG motifs in bacterial DNA trigger direct B-cell activation. Nature 374: 546-549.

Lagging, L. M., K. Meyer, R. J. Owens and R. Ray (1998) Functional role of hepatitis C virus chimeric glycoproteins in the infectivity of pseudotyped virus. J. Virol. 72: 3539-3546.

Lagging, L. M., K. Meyer, J. Westin, R. Wejstal, G. Norkrans, M. Lindh and R. Ray (2002) Neutralization of pseudotyped vesicular stomatitis virus expressing hepatitis C virus envelope glycoprotein 1 or 2 by serum from patients. J. Infect. Dis. 185: 1165-1169.

Langer R. (1990) New methods of drug delivery. Science 249: 1527-1533.

Lauer, G. M. and B. D. Walker (2001) Hepatitis C virus infection. New Engl. J. Med. 345: 41-52.

Litwin, V., K. A. Nagashima, A. M. Ryder, C. H. Chang, J. M. Carver, W. C. Olson, M. Alizon, K. W. Hasel, P. J. Maddon and G. P. Allaway (1996) Human immunodeficiency virus type 1 membrane fusion mediated by a laboratory-adapted strain and a primary isolate analyzed by resonance energy transfer. J. Virol. 70: 6437-6441.

Lu, Y. E. and M. Kielian (2000) Semliki forest virus budding: assay, mechanisms, and cholesterol requirement. J. Virol. 74: 7708-7719.

Martire, G., A. Viola, L. Iodice, L. V. Lotti, R. Gradini and S. Bonatti (2001) Hepatitis C virus structural proteins reside in the endoplasmic reticulum as well as in the intermediate compartment/cis-Golgi complex region of stably transfected cells. Virology 280: 176-182.

Matsuura, Y., H. Tani, K. Suzuki, T. Kimura-Someya, R. Suzuki, H. Aizaki, K. Ishii, K. Moriishi, C. S. Robison, M. A. Whitt and T. Miyamura (2001) Characterization of pseudotype VSV possessing HCV envelope proteins. Virology 286: 263-275.

Matsuura, Y., T. Suzuki, R. Suzuki, M. Sato, H. Aizaki, I. Saito and T. Miyamura (1994) Processing of E1 and E2 glycoproteins of hepatitis C virus expressed in mammalian and insect cells. Virology 205: 141-150.

McHutchison, J. G., S. C. Gordon, E. R. Schiff, M. L. Shiffman, W. M. Lee et al. (1998) Interferon alpha-2b alone or in combination with ribavirin as initial treatment for chronic hepatitis C. Hepatitis Interventional Therapy Group. New Engl. J. Med. 339: 1485-1492.

Meyer, K., A. Basu and R. Ray (2000) Functional features of hepatitis C virus glycoproteins for pseudotype virus entry into mammalian cells. Virology 276: 214-226.

Michalak, J. P., C. Wychowski, A. Choukhi, J. C. Meunier, S. Ung, C. M. Rice and J. Dubuisson (1997) Characterization of truncated forms of hepatitis C virus glycoproteins. J. Gen. Virol. 78: 2299-2306.

Op De Beeck, A., L. Cocquerel and J. Dubuisson (2001) Biogenesis of hepatitis C virus envelope glycoproteins. J. Gen. Virol. 82: 2589-2595.

Op De Beeck, A., R. Montserret, S. Duvet, L. Cocquerel, R. Cacan, B. Barberot, M. Le Maire, F. Penin and J. Dubuisson (2000) The transmembrane domains of hepatitis C virus envelope glycoproteins E1 and E2 play a major role in heterodimerization. J. Biol. Chem. 275: 31428-31437.

Ouyang, X., N. Tamayo and A. S. Kiselyov (1999a) Solid support synthesis of 2-substituted dibenz[b,f]oxazepin-11 (10H)-ones via $S_NAr$ methodology on AMEBA resin. Tetrahedron 55: 2827-2834.

Ouyang, X. and A. S. Kiselyov (1999b) Fast and efficient synthesis of substituted dibenz[b,f]oxazocines on solid support. Tetrahedron 55: 8295-8302.

Ouyang, X. and A. S. Kiselyov (1999c) Novel synthesis of dibenzo[b,g]1,5-oxazocines. Tetrahedron Lett. 40: 5827-5830.

Parveen, Z., A. Krupetsky, M. Engelstadter, K. Cichutek, R. J. Pomerantz and R. Dornburg (2000) Spleen necrosis virus-derived C-type retroviral vectors for gene transfer to quiescent cells. Nat. Biotechnol. 18: 623-629.

Patel, J., A. H. Patel and J. McLauchlan (1999) Covalent interactions are not required to permit or stabilize the non-covalent association of hepatitis C virus glycoproteins E1 and E2. J. Gen. Virol. 80: 1681-1690.

Patel, J., A. H. Patel and J. McLauchlan (2001) The transmembrane domain of the hepatitis C virus E2 glycoprotein is required for correct folding of the E1 glycoprotein and native complex formation. Virology 279: 58-68.

Person-Fernandez, A. and G. Beaud (1986) Purification and characterization of a protein synthesis inhibitor associated with vaccinia virus. J. Biol. Chem. 261: 8283-8289.

Pettersson, R. F. (1991) Protein localization and virus assembly at intracellular membranes. Curr. Top. Microbiol. Immunol. 170: 67-106.

Pietschmann, T., V. Lohmann, A. Kaul, N. Krieger, G. Rinck, G. Rutter, D. Strand and R. Bartenschlager (2002) Persistent and transient replication of full-length hepatitis C virus genomes in cell culture. J. Virol. 76: 4008-4021.

Ploubidou, A., V. Moreau, K. Ashman, I. Reckmann, C. Gonzalez and M. Way (2000) Vaccinia virus infection disrupts microtubule organization and centrosome function. EMBO J. 19: 3932-3944.

Ralston, R., K. Thudium, K. Berger, C. Kuo, B. Gervase, J. Hall, M. Selby, G. Kuo, M. Houghton and Q. L. Choo (1993) Characterization of hepatitis C virus envelope glycoprotein complexes expressed by recombinant vaccinia viruses. J. Virol. 0.67: 6753-6761.

Reed, K. E. and C. M. Rice (2000) Overview of hepatitis C virus genome structure, polyprotein processing, and protein properties. Curr. Top. Microbiol. Immunol. 242: 55-84.

Remington's Pharmaceutical Sciences (1985) 17th ed., Mack Publishing Co., Philadelphia, Pa.

Rice, C. M. (1996) Flaviviridiae: The viruses and their replication. 3rd ed. In "Fields Virology" (B. N. Fields, Ed.) pp. 931-1034. Lippincott-Raven Publishers, Philadelphia.

Risco, C., J. R. Rodriguez, C. Lopez-Iglesias, J. L. Carrascosa, M. Esteban and D. Rodriguez (2002) Endoplasmic reticulum-Golgi intermediate compartment membranes and vimentin filaments participate in vaccinia virus assembly. J. Virol. 76: 1839-1855.

Rodriguez, J. R., C. Risco, J. L. Carrascosa, M. Esteban and D. Rodriguez (1997) Characterization of early stages in vaccinia virus membrane biogenesis: implications of the 21-kilodalton protein and a newly identified 15-kilodalton envelope protein. J. Virol. 71: 1821-1833.

Sanger, C., E. Muhlberger, H. D. Klenk and S. Becker (2001) Adverse effects of MVA-T7 on the transport of Marburg virus glycoprotein. J. Virol. Methods 91: 29-35.

Selby, M. J., E. Glazer, F. Masiarz and M. Houghton (1994) Complex processing and protein:protein interactions in the E2:NS2 region of HCV. Virology 204: 114-122.

Serafino, A., M. B. Valli, A. Alessandrini, A. Ponzetto, G. Carloni and L. Bertolini. (1997) Ultrastructural observations of viral particles within hepatitis C virus-infected human B lymphoblastoid cell line. Res. Virol. 148: 153-159.

Shimizu, Y. K., S. M. Feinstone, M. Kohara, R. H. Purcell and H. Yoshikura. (1996) Hepatitis C virus: detection of intracellular virus particles by electron microscopy. Hepatology 23: 205-209.

Spaete, R. R., D. Alexander, M. E. Rugroden, Q. L. Choo, K. Berger et al. (1992) Characterization of the hepatitis C virus E2/NS1 gene product expressed in mammalian cells. Virology 188: 819-830.

Szepanski, S., M. Veit, S. Pleschka, H. D. Klenk, M. F. Schmidt and G. Herrler (1994) Post-translational folding of the influenza C virus glycoprotein HEF: defective processing in cells expressing the cloned gene. J. Gen. Virol. 75: 1023-1030.

Takikawa, S., K. Ishii, H. Aizaki, T. Suzuki, H. Asakura, Y. Matsuura and T. Miyamura (2000) Cell fusion activity of hepatitis C virus envelope proteins. J. Virol. 74: 5066-5074.

Wei, G. P. and G. B. Phillips (1998) Solid phase synthesis of benzimidazolones. Tetrahedron Lett. 39: 179-182.

Yanagi, M., R. H. Purcell, S. U. Emerson and J. Bukh (1997) Transcripts from a single full-length cDNA clone of hepatitis C virus are infectious when directly transfected into the liver of a chimpanzee. Proc. Natl. Acad. Sci. USA 94: 8738-8743.

Young, K. K., R. M. Resnik and T. W. Myers (1993) Detection of hepatitis C virus RNA by a combined reverse transcription polymerase chain reaction assay. J. Clin. Microbiol. 31: 882-886.

What is claimed is:

1. A nucleic acid comprising consecutive nucleotides, the sequence of which corresponds to a sequence encoding a hepatitis C virus (HCV) E1 glycoprotein in which (a) at least one nucleotide has been altered to eliminate a RNA splice acceptor site or a RNA splice donor site, wherein the altered nucleotide is (i) an A886C mutation, (ii), a G888T mutation, or (iii) a G675A mutation, or (b) nucleotides 675-887 have been deleted, wherein the positions of the mutation and the deleted nucleotides are numbered by reference to SEQ ID NO:2.

2. The nucleic acid of claim 1, wherein at least one nucleotide has been altered to eliminate a RNA splice acceptor site and the altered nucleotide is an A886C mutation.

3. The nucleic acid of claim 1, wherein at least one nucleotide has been altered to eliminate a RNA splice acceptor site and the altered nucleotide is a G888T mutation.

4. The nucleic acid of claim 1, wherein at least one nucleotide has been altered to eliminate a RNA splice donor site and the altered nucleotide is a G675A mutation.

5. The nucleic acid of claim 1, wherein nucleotides 675-887 have been deleted.

6. The nucleic acid of any of claims 1-5 comprising further consecutive nucleotides, the sequence of which corresponds to a sequence encoding HCV E2 glycoprotein, wherein the sequence encoding HCV E2 glycoprotein has at least one nucleotide that has been altered to eliminate a RNA splice acceptor site, and wherein the altered nucleotide in the sequence encoding HCV E2 glycoprotein is an A2183T mutation, the position of the mutation being numbered by reference to SEQ ID NO:2.

7. An isolated host cell which comprising a vector comprises a nucleic acid comprising consecutive nucleotides, the sequence of which corresponds to a sequence encoding a hepatitis C virus (HCV) E1 glycoprotein in which (a) at least one nucleotide has been altered to eliminate a RNA splice acceptor site or a RNA splice donor site, wherein the altered nucleotide is (i) an A886C mutation, (ii) a G888T mutation, or (iii) a G675A mutation, or (b) nucleotides 675-887 have been deleted, wherein the positions of the mutation and the deleted nucleotides are numbered by reference to SEQ ID NO:2.

8. The isolated host cell of claim 7, wherein the nucleic acid comprises further consecutive nucleotides, the sequence of which corresponds to a sequence encoding HCV E2 glycoprotein, wherein the sequence encoding HCV E2 glycoprotein has at least one nucleotide that has been altered to eliminate a RNA splice acceptor site, and wherein the altered nucleotide in the sequence encoding HCV E2 glycoprotein is an A2183T mutation, the position of the mutation being numbered by reference to SEQ ID NO:2.

9. The isolated host cell of claim 7, wherein the isolated host cell is a cultured cell.

10. The isolated host cell of claim 9, wherein the cultured cell is a mammalian cell.

11. A method for expressing on a cell surface an altered hepatitis C virus (HCV) glycoprotein which comprises transfecting a cell with a vector which comprises a nucleic acid comprising consecutive nucleotides, the sequence of which corresponds to a sequence encoding a hepatitis C virus (HCV) E1 glycoprotein in which (a) at least one nucleotide has been altered to eliminate a RNA splice acceptor site or a RNA splice donor site, wherein the altered nucleotide is (i) an A886C mutation, (ii) a G888T mutation, or (iii) a G675A mutation, or (b) nucleotides 675-887 have been deleted, wherein the positions of the mutation and the deleted nucleotides are numbered by reference to SEQ ID NO:2, under conditions which permit expression of the nucleic acid such that the altered HCV glycoprotein is expressed on the surface of a cell.

12. The method of claim 11, wherein greater than 70% of the altered HCV glycoprotein expressed on the surface of the cell is a full length HCV glycoprotein.

13. The method of claim 11, wherein greater than 90% of the altered HCV glycoprotein expressed on the surface of the cell is a full length HCV glycoprotein.

14. A method for making a pseudovirion expressing on its surface an altered hepatitis C virus (HCV) glycoprotein which comprises:

(a) co-transfecting a cell with (i) at least one packaging vector which expresses a reporter gene, and (ii) a vector which comprises a nucleic acid comprising consecutive nucleotides, the sequence of which corresponds to a sequence encoding a hepatitis C virus (HCV) E1 glycoprotein in which (a) at least one nucleotide has been altered to eliminate a RNA splice acceptor site or a RNA splice donor site, wherein the altered nucleotide is (i) an A886C mutation, (ii) a G888T mutation, or (iii) a G675A mutation, or (b) nucleotides 675-887 have been deleted, wherein the positions of the mutation and the deleted nucleotides are numbered by reference to SEQ ID NO:2, under conditions which permit transcription of the nucleic acid, thereby making a pseudovirion expressing on its surface a altered HCV glycoprotein.

15. The method of claim 14, wherein greater than 70% of the altered HCV glycoprotein expressed on the surface of the pseudovirion is a full length HCV glycoprotein.

16. The method of claim 14, wherein greater than 90% of the altered HCV glycoprotein expressed on the surface of the pseudovirion is a full length HCV glycoprotein.

17. The method of claim 14, wherein the packaging vector expresses a luciferase, a green fluorescent protein or a beta-galactosidase reporter gene.

18. The method of 14, wherein the packaging vector is pNL4.3-Luc+env- and expresses a luciferase.

19. The method of claim 14, where the cell is a 293T cell.

* * * * *